(12) United States Patent
Giuliano et al.

(10) Patent No.: US 11,414,666 B2
(45) Date of Patent: Aug. 16, 2022

(54) VIRAL VECTORS FOR TREATING NEUROGENIC DETRUSOR OVERACTIVITY

(71) Applicants: UNIVERSITE DE VERSAILLES-ST QUENTIN EN YVELINES, Versailles (FR); ASSISTANCE PUBLIQUE—HOPITAUX DE PARIS, Paris (FR)

(72) Inventors: François Giuliano, Paris (FR); Alberto Epstein, Montigny-le-Bretonneux (FR); Olivier Le Coz, Le Mesnil saint denis (FR); Alejandro Aranda, Pamplon (ES)

(73) Assignees: UNIVERSITE DE VERSAILLES-ST QUENTIN EN YVELINES, Versailles (FR); ASSISTANCE PUBLIQUE—HOPITAUX DE PARIS, Paris (FR)

(*) Notice: Subject to any disclaimer, the term of this patent is extended or adjusted under 35 U.S.C. 154(b) by 605 days.

(21) Appl. No.: 16/312,867

(22) PCT Filed: Jun. 23, 2017

(86) PCT No.: PCT/EP2017/065587
§ 371 (c)(1),
(2) Date: Dec. 21, 2018

(87) PCT Pub. No.: WO2017/220800
PCT Pub. Date: Dec. 28, 2017

(65) Prior Publication Data
US 2020/0071703 A1    Mar. 5, 2020

(30) Foreign Application Priority Data

Jun. 23, 2016 (EP) .................. 16305765.6

(51) Int. Cl.
| | |
|---|---|
| *A61K 38/16* | (2006.01) |
| *A61P 13/00* | (2006.01) |
| *A61K 38/48* | (2006.01) |
| *C12N 15/869* | (2006.01) |
| *C12N 15/113* | (2010.01) |
| *A61P 13/06* | (2006.01) |
| *A61K 38/17* | (2006.01) |
| *A61K 38/45* | (2006.01) |
| *A61K 38/51* | (2006.01) |
| *C12N 15/86* | (2006.01) |

(52) U.S. Cl.
CPC ........ *C12N 15/1138* (2013.01); *A61K 38/164* (2013.01); *A61K 38/1793* (2013.01); *A61K 38/45* (2013.01); *A61K 38/4893* (2013.01); *A61K 38/51* (2013.01); *A61P 13/06* (2018.01); *C12N 15/86* (2013.01); *C12Y 304/24069* (2013.01); *C12Y 401/01015* (2013.01); *C12N 2310/11* (2013.01); *C12N 2320/31* (2013.01); *C12N 2320/32* (2013.01); *C12N 2710/16643* (2013.01); *C12N 2830/008* (2013.01); *C12N 2830/40* (2013.01)

(58) Field of Classification Search
CPC ... A61K 38/164; A61K 38/4893; A61P 13/00; C12N 15/8695
See application file for complete search history.

(56) References Cited

U.S. PATENT DOCUMENTS

| | | | |
|---|---|---|---|
| 6,812,339 B1* | 11/2004 | Venter et al. .......... | C07H 21/04 536/24.31 |
| 2015/0297649 A1* | 10/2015 | Goins et al. ......... | A61K 35/763 |

FOREIGN PATENT DOCUMENTS

| | | | | |
|---|---|---|---|---|
| WO | WO 99/03483 A1 | 1/1999 | | |
| WO | WO 2006/050211 A2 | 5/2006 | | |
| WO | WO 2010/022979 A1 | 3/2010 | | |
| WO | WO 2013/180799 A1 | 12/2013 | | |
| WO | WO 2015/009952 A1 | 1/2015 | | |
| WO | WO2015009952 A1 * | 1/2015 | ........... | C12N 15/869 |
| WO | WO2017004514 A1 * | 1/2017 | ............. | A61K 48/00 |

OTHER PUBLICATIONS

Miyazato et al. "Herpes simplex virus vector-mediated gene delivery of glutamic acid decarboxylase reduces detrusor overactivity in spinal cord-injured rats" Gene Therapy (2009) 16, 660-668. (Year: 2009).*
Doyal et al. "319. In Vivo Transcriptional Targeting of HSV Vector Mediated Transgene Expression in Sensory Neuron Subpopulations" Molecular Therapy (2014), vol. 22, Supplement 1, p. S123. (Year: 2014).*
Teng et al. "Adenoviral clostridial light chain gene-based synaptic inhibition through neuronal synaptobrevin elimination" Gene Therapy (2005) 12, 108-119. (Year: 2005).*
Fowler et al. "Systematic review of therapy for neurogenic detrusor overactivity" Can Urol Assoc J (2011), 5(5Suppl2):S146-S148. (Year: 2011).*
Su et al. "Preclinical assessment of potential interactions between botulinum toxin and neuromodulation for bladder micturition reflex" BMC Urol. Jun. 9, 2015, 15:50, 7 pages. (Year: 2015).*
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," Journal of Virology, vol. 80, No. 5, Mar. 2006, pp. 2358-2368.

(Continued)

*Primary Examiner* — James D Schultz
*Assistant Examiner* — James Joseph Graber
(74) *Attorney, Agent, or Firm* — Birch, Stewart, Kolasch & Birch, LLP

(57) ABSTRACT

The present invention provides a method and a pharmaceutical composition for the treatment of the NDO comprising the viral expression vector carrying a transcription cassette that harbors transgene(s) inhibiting/silencing neurotransmission or synaptic transmission of afferent neurons.

9 Claims, 13 Drawing Sheets

Specification includes a Sequence Listing.

(56) References Cited

OTHER PUBLICATIONS

Berthomme et al., "Enhancer and Long-Term Expression Functions of Herpes Simplex Virus Type 1 Latency-Associated Promoter Are both Located in the Same Region," Journal of Virology, vol. 75, No. 9, May 2001, pp. 4386-4393.

Berthomme et al., "Evidence for a Bidirectional Element Located Downstream from the Herpes Simplex Virus Type 1 Latency-Associated Promoter That Increases Its Activity during Latency," Journal of Virology, vol. 74, No. 8, Apr. 2000, pp. 3613-3622.

Brindley et al., "Sacral anterior root simulators for bladder control in paraplegia: the first 50 cases," Journal of Neurology, Neurosurgery, and Psychiatry, vol. 49, 1986, pp. 1104-1114.

Epstein, "HSV-1-derived amplicon vectors: recent technological improvements and remaining difficulties—A Review," Mem Inst Oswaldo Cruz, vol. 104, No. 3, May 2009, pp. 399-410.

Fowler et al., "The neural control of micturition," Nat Rev Neurosci, vol. 9, No. 6, Jun. 2008, pp. 453-466 (28 pages total).

Fowler, "Systematic review of therapy for neurogenic detrusor overactivity," Canadian Urological Association, vol. 5, Oct. 2011, pp. 5146-5148.

Furuta et al., "Latent Herpes Simplex Virus Type 1 in Human Vestibular Ganglia," Acta Oto-Laryngologica, Suppl. 503, 1993 (published online Jul. 8, 2009), pp. 85-89 (6 pages total).

Habermann et al., "Clostridial Neurotoxins: Handling and Action at the Cellular and Molecular Level," Current Topics in Microbiology and Immunology, vol. 129, 1986, pp. 93-179 (88 pages total).

International Search Report for International Application No. PCT/EP2017/065587, dated Sep. 15, 2017.

Lokensgard et al., "The Latency-Associated Promoter of Herpes Simplex Virus Type 1 Requires a Region Downstream of the Transcription Start Site for Long-Term Expression during Latency," Journal of Virology, vol. 71, No. 9, Sep. 1997, pp. 6714-6719.

Marconi et al., "HSV-1-derived helper-independent defective vectors, replicating vectors and amplicon vectors, for the treatment of brain diseases," Current Opinion in Drug Discovery & Development, vol. 13, No. 2, 2010, pp. 169-183.

Martens et al., "Clinical Results of a Brindley Procedure: Sacral Anterior Root Stimulation in Combination with a Rhizotomy of the Dorsal Roots," Advances in Urology, vol. 2011, 2011, pp. 1-7 (8 pages total).

Matak et al., "Botulinum toxin A. brain and pain," Progress in Neurobiology, vol. 119-120, 2014 (published online Jun. 7, 2014), pp. 39-59.

McCart et al., "Development of a Melanoma-Specific Adenovirus," Molecular Therapy, vol. 6, No. 4, Oct. 2002, pp. 471-480.

Miyazato et al., "Herpes simplex virus vector-mediated gene delivery of gutamic acid decarboxylase reduces detrusor overactivity in spinal cord injured rats," Gene Ther., vol. 16, No. 5, May 2009, pp. 660-668 (20 pages total).

Morrison et al., "Neural Control," Incontinence. Plymouth: Health, 2005, pp. 363-422.

Perng et al., "The Spontaneous Reactivation Function of the Herpes Simplex Virus Type 1 LAT Gene Resides Completely within the First 1.5, Kilobases of the 8.3-Kilobase Primary Transcript," Journal of Virology, vol. 70, No. 2, Feb. 1996, pp. 976-984.

Ren et al., "Electrical Nerve Stimulation to Promote Micturition in Spinal Cord Injury Patients: A Review of Current Attempts," Neurology and Urodynamics, vol. 35, Feb. 8, 2015, pp. 365-370.

Stolarsky-Fredman et al., "Rat calcitonin gene related peptide (CGRP) gene, 5' flank," Database EMBL, accession No. M34090, Jun. 22, 1990, 2 pages.

Su et al., "Preclinical assessment of potential interactions between botulinum toxin and neuromodulation for bladder micturition reflex," BMC Urology, published online Jun. 9, 2015, pp. 1-7.

Sugiyama, "Clostridium botulinum Neuorotoxin," Microbiological Reviews, vol. 44, No. 3, Sep. 1980, pp. 419-448.

Tanaka et al., "Construction of an Excisable Bacterial Artificial Chromosome Containing a Full-Length Infectious Clone of Herpes Simplex Virus Type 1: Viruses Reconstituted from the Clone Exhibit Wiid-Type Properties . . . ," Journal of Virology, vol. 77, No. 2, Jan. 2003, pp. 1382-1391.

Warren et al., "Isolation of Latent Herpes Simplex Virus From the Superior Cervical and Vagus Ganglions of Human Beings," The New England Journal of Medicine, vol. 298, No. 19, May 11, 1978, pp. 1068-1069.

Xue et al., "Rattus norvegicus transient receptor potential vanilloid subtype-1 (TRPV1)," Database EMBL, accession No. EMBL:DQ015702, May 2006, 3 pages.

Yokoyama, et al., "Gene Therapy for Bladder Overactivity and Nociception with Herpes Simplex Virus Vectors Expressing Preproenkephalin," Human Gene Therapy, vol. 20, Jan. 2009 (published online Jan. 14, 2009), pp. 63-71.

Yoshikawa et al., "Suppression of Detrusor Overactivity by Herpes Simplex Virus (HSV) Vector-Mediated Delivery of Glial Cell Line-Derived Neurotrophic Factor (GDNF) In Spinal Cord Injured Rats," International Continence Society 2013, Aug. 28, 2013, pp. 71-72.

Zaupa et al., Improved Packaging System for Generation of High-Level Noncytotoxic HSV-1 Amplicon Vectors Using Cre-loxP Site-Specific Recombination to Delete the Packaging Signals of Defective Helper Genomes, Human Gene Therapy, vol. 14, Jul. 20, 2003, pp. 1049-1063.

* cited by examiner

A

![Construct diagram: GFP - IE4/5 - ■ - DRGsp prom - BoNT or GAD67 or SAP - ■]

B

A: GFP - IE4/5 - Prom HCMV - TeNT (LC)
B: GFP - IE4/5 - Prom HCMV - BoNT-A (LC)
C: GFP - IE4/5 - Prom HCMV - BoNT-C (LC)
D: GFP - IE4/5 - Prom HCMV - SNAP25 (AS)
E: GFP - IE4/5 - Prom HCMV - Luciferase
F: GFP - IE4/5 - Prom TRPV1 - Luciferase

Fig. 3

Gli36 cells | BHK cells
Luc  TeNT  BoNTA  BoNTC    Luc  TeNT  BoNTA  BoNTC    recTeNT 50 kDa α-TeNT α-His

Human neural cells infected by HSV-1 defective vectors expressing BoNT-A (LC)

BoNT-A (LC) cleaves SNAP25

A2- Therapeutic gene product

| Family | Promoter | Therapeutic gene |
|---|---|---|
| A2 | CMV | BoNT-X |
| A2 | CMV | TeNT |
| A2 | CMV | BoNT-X-SNARE-Y |
| A2 | CMV | GAD67 |
| A2 | CMV | NTR |
| A2 | CMV | Luc |
| A2 | CMV | AS-SNARE-X |

B.

A5-DRG specific promoters

| Family | DGR-promoter | Reporter gene |
|---|---|---|
| A5 | EF1a | Luciferase |
| A5 | rTRPV1 | Luciferase |
| A5 | rASIC3 | Luciferase |
| A5 | rCGRP | Luciferase |
| A5 | hCGRP | Luciferase |
| A5 | rADVL | Luciferase |
| A5 | hADVL | Luciferase |
| A5 | LAP1 | Luciferase |
| A5 | LAP2 | Luciferase |

C.

A8- Therapeutic cassettes

| Family | DRG-promoter | Therapeutic gene |
|---|---|---|
| A8 | EF1A | BoNT-F |
| A8 | rTRPV1 | BoNT-A-STX |
| A8 | hADVL | TeNT |
| A8 | hCGRP | GAD67 |
| A8 | rCGRP | NTR |
| A8 | hADVL | BoNT-F |
| A8 | rTRPV1 | GAD67 |
| A8 | hADVL | NTR |
| A8 | rCGRP | Luc |
| A8 | hCGRP | BoNT-A-STX |
| A8 | rADVL | GAD67 |
| A8 | hCGRP | BoNT-F |
| A8 | hCGRP | AS-SNARE-X |

A
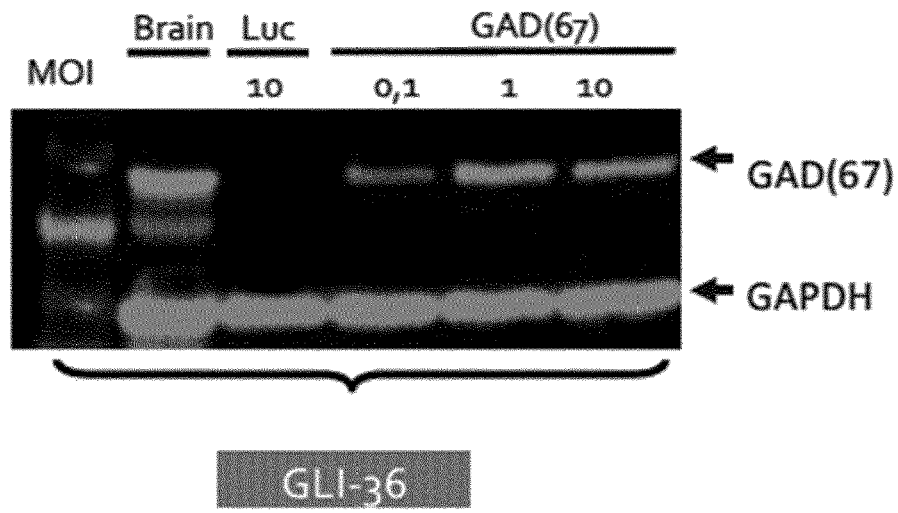
WB of GAD67 24h post infection in GLI-36 cells (n=1)
B
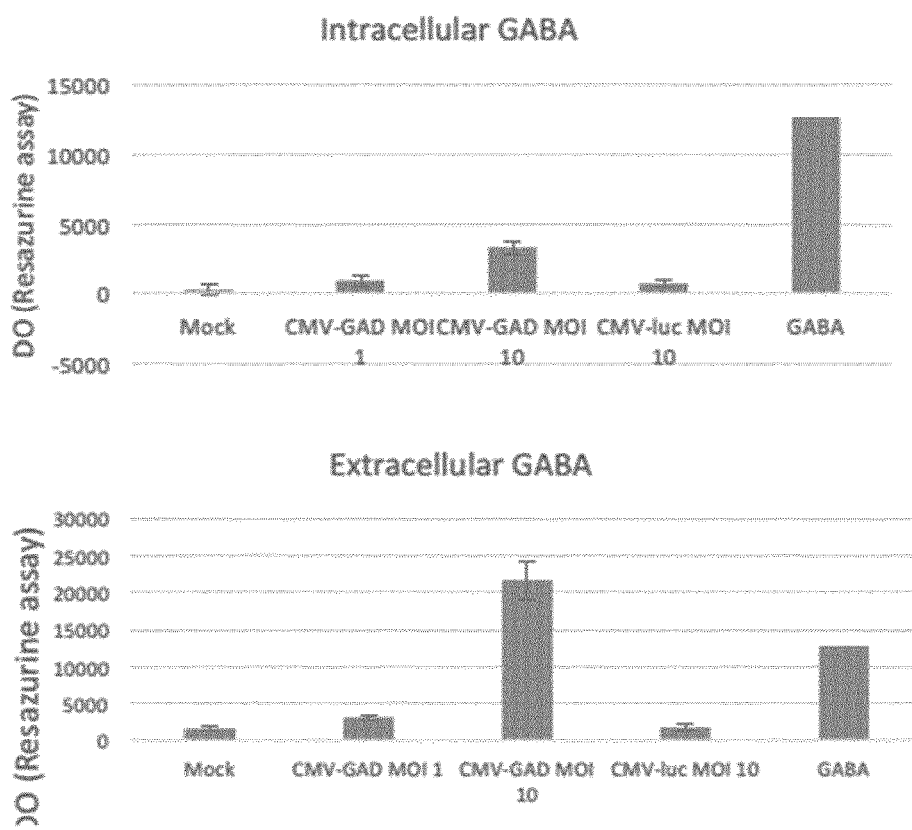
GABA release in primary cultures of embryonic rat DRG neurons (n=6)
Fig. 11

A
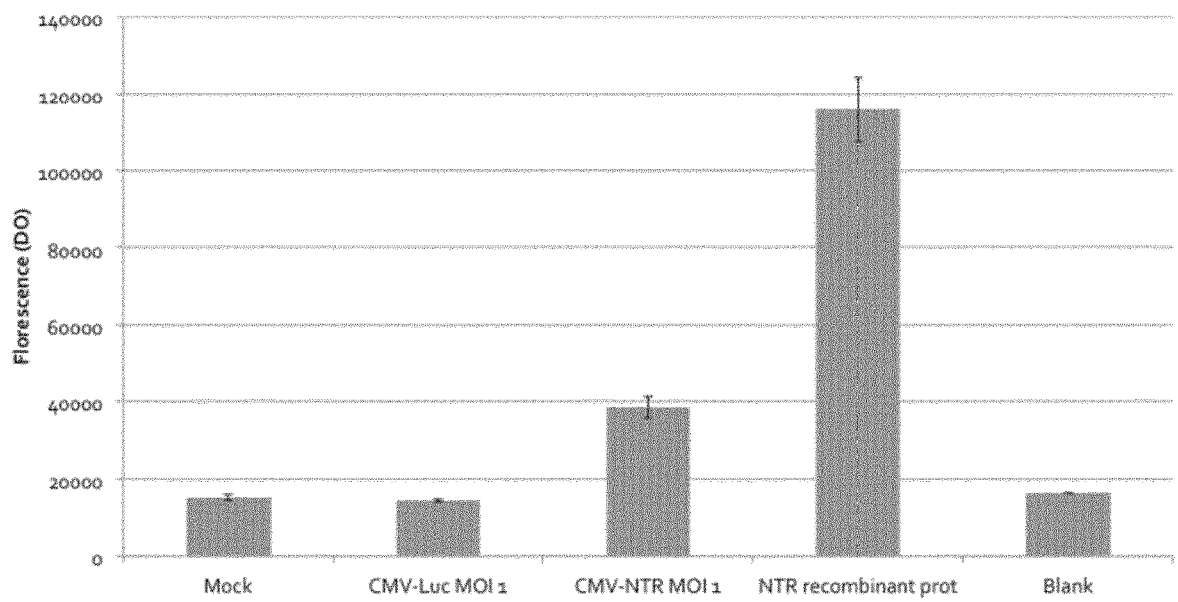
Gli 36 cells – reduction of 7'nitrocoumarin at 48 hs pi.
B
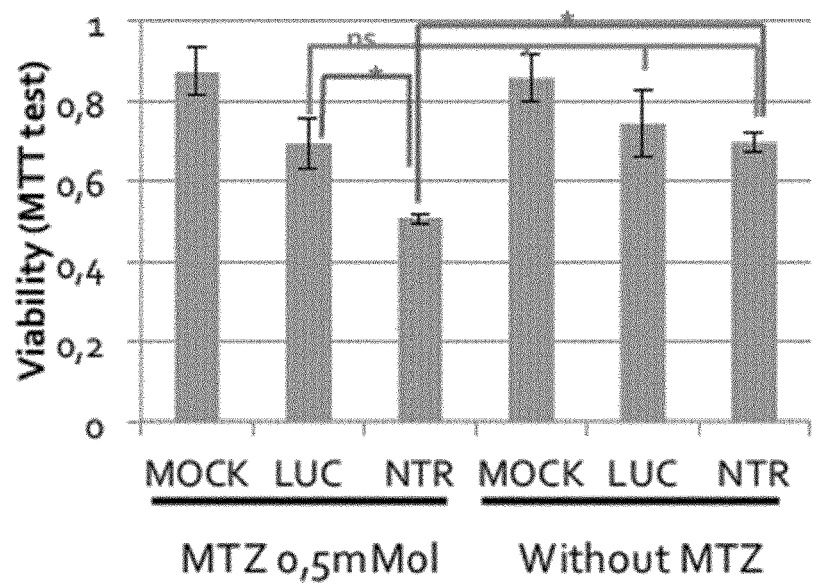
Gli 36 cells – MTT assay at 24 hs pi.
Fig. 12

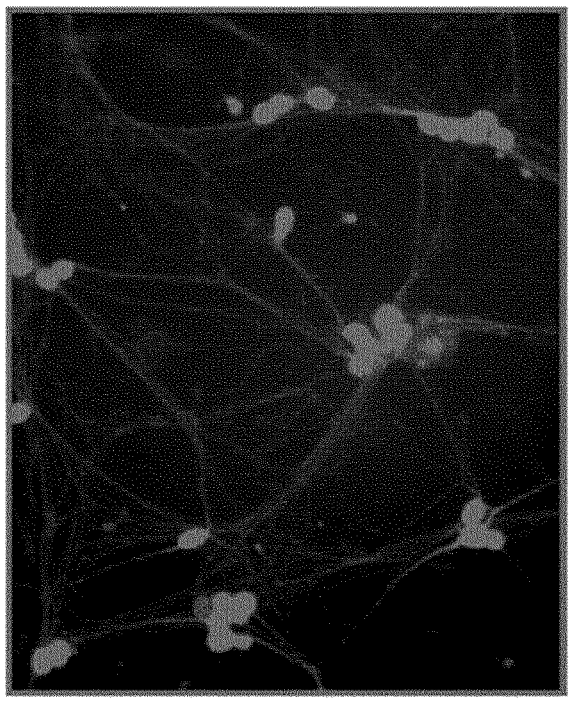
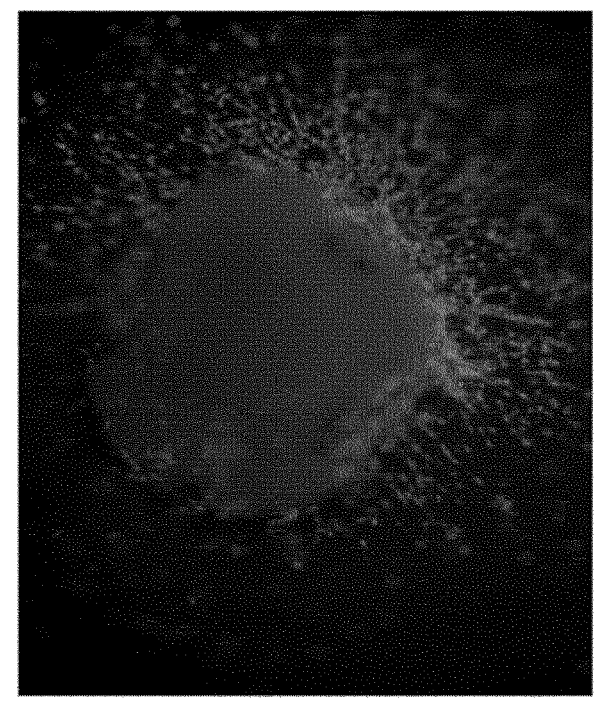
Fig. 14

SEQUENCE LISTING

```
<160> NUMBER OF SEQ ID NOS: 33

<210> SEQ ID NO 1
<211> LENGTH: 1020
<212> TYPE: DNA
<213> ORGANISM: Rattus norvegicus

<400> SEQUENCE: 1
atatggagag gtggggtgag gggtggcaga gagggatcga gagaggagag aggggaacca      60
gatgtagcag ccaggaggcc aaaggtacaa aagggtggg taaccaaaat gtctggatta     120
tataaaaaag agccagaggt caggcccact ttgatatgtt aaataggcac ctcagccatt     180
tatccaggtt tgaaatgtaa tataatttac atcccctgg cttcctagag accgttgttt      240
agacggatga cctctgcaga atgtttgagg gtgcagtctt gcatgtactc cctggtgggc     300
tttcttgggc aggatctggg caggaatggg cttgttctag tcacccactg cgtatgatgg     360
atgaacccgc ttcctagtag ttaggatggc actggggag gcgagaaatt agcacacgta     420
acgtttcttt gtgttctatt gttcactaag ggaccccagt caagcaagac tgggccttgg     480
aagacctaga gaccaccaaa cctaatctct accccgggtc tgagtacaca gggactcaga     540
gtcccaaagg gggcagggcc tccagacagg tggctcagag gtcccagtcc tttggaaaca     600
tggcatcttc aggacactgg gctttgcatc tctggctgtg acagtccttt aagggagcta     660
ctcctcagac ataccaggaga gatggtttgg aaagtccgag atccaaagcc tggttcaggc    720
tggactgggc tgcaggctgc taagtgctcc tctgccctgg catggctggg ggtggggcat     780
tggctgtggt ttctgaaaaa gggcaaaaat gatgggaaaa gctttgggat cctctgggaa     840
```

```
tcggagccgt ggtaacagca gctgctgcca ttgctgcaaa tgtttccttg agtgccagag    900
tatgcccaga gcccatccct gccgtacgcc aggggagggg cgaggaccct cacagaggca    960
gggaggccgg ccactcttac cacacagcag cctggctctc ccacaaagaa cagctatgca   1020
```

<210> SEQ ID NO 2
<211> LENGTH: 975
<212> TYPE: DNA
<213> ORGANISM: Homo sapiens

<400> SEQUENCE: 2

```
gacttaccag gagctagggc atttataagc attgtgccct gaagataagt tcaccccagg     60
cagttctgaa aaggactcgt caaacatgtc ctgctgtaga ataatttcta aaaatgtttt    120
tcagatctta ggagtaatat aaacatgcag aaaagtagaa ggaagaaaat aatgacctga    180
tacaaactaa aggtttgagt gctgtgtgaa cagtctaagg gaggttattg aattggggtg    240
aaaagaatag aaagaagagc gcagataatt gtaaatagtaa caatagctaa tatttattga    300
agctttccca tgctgggcac aggttcaagt gctttacagg ggtcgcctca tttaattatt    360
actcatttct gtgtaggtgt gtagccggtg ggctagttca ggttcttgac tttgggacag    420
aaaataattt gaaagtgagt caaaagcaaa agcaagcaag agagttgact gcaaagccaa    480
agtacactct gcagccggt cagaacgggc cactcaaagg caagacagct ctgtctaata    540
ctgggggatc tcccttatg ggaaatttgc atgattattc atgaagggggt ggtaagggt    600 gttgctatta agcatgttag gagtggtttc ttaggtccac atgtgcagtg gctgtacatg    660
ctagtacatc catcgcatgt cttataagca ttttaaatct ccacctgggg gtgtgttttt    720
tactattata atgagcacag gtcagcccaa ggacactaat cacgggtttc tgtgcttgta    780
caaatgtggg gatttttctc ttctgctcct gccttttgc tgtagggtgt tctaaccacg    840
agctcaggat gcggtctgtg cactgttagg tggtttgttc tcttcatcaa tttgacaagt    900
ttcttgtttc ctgtcaaggg aggctctgac cacctcatct aacctgcctc aggtgcagcc    960
ttattgccat tttac                                                     975
```

<210> SEQ ID NO 3
<211> LENGTH: 1360
<212> TYPE: DNA
<213> ORGANISM: rat

<400> SEQUENCE: 3

```
gagggacttg aaggcaggct tgggacaatt tgagaatgaa cccctaagga tgcttctgtg     60
ggccacagag actgctgagt ggctgtgctt tctggatacg gtaccatttt ggaaagagag    120
gagagtctct gtgccaggag aagtgtgact ggtagtgaat gtgaggttta gtacgggca    180 acatctccac agcgctgtca agcctgcctg cctgctcttc agctctttag ctcggagatc    240
taagggtggg ggtaggaggg gagccaccgg accaaataca actgggacat cttggcaaac    300
agcagcggga agcaaagggg cagctgtgca aatccttagg caggcgggcg ggcgggcagg    360
cgggcgggcg ggcgggcagg cgggcaggcg ggcgggcagg cggccggatg agtagtgatg    420
gatagccagg caggaggtgg agagatctac actggagact ttagaggcat ctggtccttc    480
ctcacactgt ccccactacc ccgtaccct actccctacc ccaagcagga cccagctgaa    540 tacaaccct tctcacacat gtgagtgagt gagttatcca gcacataaga atgccaagct    600
gaagacggat gattcacttt ggggaaggag agattttata gctcaggaaa caccaaggtt    660
```

```
tctgcctact agccaggccc ttcaaaaggg gaccaggata cccactgaaa agtttaatat    720
gttgagcttt cgtgcaggcc tttgggggtt tgggggggg ggaattttga attttttttt    780
tcgttttgtt tttacctgtg gtcacataac cagcacgagg cagctacaag gttcaggtct    840
gacagagccc ctgtgtccag caccaacacc tttggctatc agcctaaacc tgtgccaccc    900
tgccaaagcc agccttgcag accaagagtc caccccctacg gtgcactaaa gtcttccgga    960
ttaggcacgg actagggtcg gggcacgatt agaatcagac atgcagcaag gagtacttga   1020
gatactggac tctactctcc aaggtccaga gattggagtc ggggatgttc aaagtcagga   1080
gggaagaaga gataaaattt accttgacgt caaaaggccc tccaaattcc cgctaatttt   1140
aagggtggtt ctcactgctc cccaccatcc tcccacttcc atcaatgacc tcaatttaaa   1200
ttcaaatggt gtcatcttgc tagatgctcg gagttctgga agcaccgagg tgacgcaatc   1260
tgtctggggc acggggcect tccacctatt ggctgcctgg cgccccggga cccctcccaa   1320
ctaccgcggc gggaataaga gcagctgcag gcgcttggaa                         1360
```

<210> SEQ ID NO 4
<211> LENGTH: 1837
<212> TYPE: DNA
<213> ORGANISM: Homo sapiens

<400> SEQUENCE: 4

```
gatcaattaa gggcatctta gaagttaggc gttcccgctg cctcctttga gcacggaggc     60
caccaacccc ctagggggaa gagatgtagc gcgaggcagg ggtgtcgtgc taagaaattt    120
cgacgcttct ggggactgag gacaaaggtg cggacacgac cccggggtac ctggagttcc    180
gtgactcgcg ccacggacgg cacacctagg ggctaatttc tgctctgcct caaagaacct    240
caagctagag tccttgcctc cgcccacagc cccgggatgc cgctgctgcg ctcaccgcac    300
aggcagcgcc cggaccggct gcagcagatc gcgcgctgcg cgttccaccg ggagatggtg    360
gagacgctga aaagcttctt tcttgccact ctggacgctg tgggcggcaa cgccttagt    420 ccctacctct gctgagctga acgctcaggc acagtggaac tgaaacccgg ttctgcggga    480
tgtgagagct gttgaggtca cgcgtaattg ggtgtgatgg agggcgcctg ttcgtgatgt    540
gtgcaggttt gatgcaagca ggtcatcgtc gtgcgagtgt gtggatgcga ccgcccgaga    600
gactcggagg caggcttggg acacgttga gtgaacacct caggatactc ttctggccag    660
tatctgtttt ttagtgtctg tgattcagag tgggcacatg ttgggagaca gtaatgggtt    720
tgggtgtgtg taaatgagtg tgaccggaag cgagtgtgag cttgatctag cagggacca    780 cacagcactg tcacacctgc ctgctctttta gtagaggact gaagtgcggg ggtgggggta    840
cggggccgga atagaatgtc tctgggacat cttggcaaac agcagccgga agcaaagggg    900
cagctgtgca aacggctcag gcaggtgatg gatggcaggg taggaagggg gaggtccaga    960
ggtctggatg gaggcttccg catctgtacc ttgcaactca cccctcaggc ccagcaggtc   1020
atcggccccc tcctcacaca tgtaatggat ctgaagagta ccccgggaca gtccggggag   1080
atggagattc ggaaagtatc catggagatc ttacagaatc cctatgcgg accaggaaac    1140 tcttgtagat ccctgcctat ctgaggccca ggcgctgggc tgtttctcac aatattcctt   1200
caagatgaga ttgtggtccc catttcaaag atgagtacac tgagcctctg tgaagttact   1260
tgcccatgat cacacaacca ggaattgggc caactgtaat tgaactcctg tctaacaaag   1320
ttcttgctcc cagctccgtc tcttgttttcc cacgagccct ggcctctgt gggtaatacc   1380 agctactgga gtcagatttc ttgggcccag aacccaccct tagggcatt aacctttaaa   1440
```

| | |
|---|---:|
| atctcacttg ggcagggtc tgggatcaga gttggaagag tccctacaat cctggaccct | 1500 |
| ttccgccaaa tcgtgaaacc aggggtggag tggggcgagg gttcaaaacc aggccggact | 1560 |
| gagaggtgaa attcaccatg acgtcaaact gccctcaaat tcccgctcac tttaagggcg | 1620 |
| ttacttgttg gtgccccac catccccac catttccatc aatgacctca atgcaaatac | 1680 |
| aagtgggacg tcctgctgg atcctccagg ttctggaagc atgagggtga cgcaacccag | 1740 |
| gggcaaagga cccctccgcc cattggttgc tgtgcactgg cggaactttc ccgacccaca | 1800 |
| gcggcgggaa taagagcagt cgctggcgct gggaggc | 1837 |

```
<210> SEQ ID NO 5
<211> LENGTH: 1633
<212> TYPE: DNA
<213> ORGANISM: rat

<400> SEQUENCE: 5
```

| | |
|---|---:|
| tggccctgcc ctgccctgtt cagaggcttc ttggcagtgc ggcccatttg tgctgtcctg | 60 |
| catccagtgt atcagcctag ctaagtgtga gccatttcca tttggggcta ctcttcagtt | 120 |
| cctttttaa aatagcttag ccctctccct tacctctacc cctagacagg gtttcatgaa | 180 |
| ttccaagcag gggcctcaac tcacatttag ccaggaatga tcttgaactg acctcctgag | 240 |
| tgctggggtt acaggtgtga tcaccttgct gctttaggag gtgctgggaa caacccaggg | 300 |
| catcgtgtgt gttaagcaca cactcccagc taagctacat ccccagtccc tctttctaga | 360 |
| aaacatcatt agttaaatat attcagggga aagaggtca caggtctggc cagctgcccc | 420 |
| atcctttagt gcagggtcag ctcccagaac tgctctgctc tgctctgcaa gctggtgatt | 480 |
| ctccttacct gtgattactc cagatctgcc tatttccaag atgccatttg aaggggaggg | 540 |
| gtctgcttcc cactgtgact gggctatggg atccttgacc accttgcttc atgatttgat | 600 |
| acatttgttg tattcaaaaa cttgaactgt aggatgccat taagagtctg tttatatttt | 660 |
| tggaatattt gtattacaat tgttttaata aaggccggtt taaaaaccta tgcatgagtg | 720 |
| ggggctgctt tccttccccg ccactggtcc cacacacggt ggacgctgtt ctcccgtat | 780 |
| tcccttttg gtcctaagat tatagcaccc agcagaacaa acactgggtt ctgatcaagg | 840 |
| ttgcaaaggt tggactgcat tagctcttct ctggcccagg ttggaaccaa ctccctctcc | 900 |
| cctgggtact tagcaaacat gtgcttgctg tgctattgac tgctgggtat agactgaagc | 960 |
| ccttggggaa ttggggactc ctgtgcatgc tcttgatact gccaaacagg agccatgaga | 1020 |
| ctcagagccc agcacggttt ccaggcacat agtaggagga cttgtaaaga ctaaacaaaa | 1080 |
| gctttcctat caccacaaat ttgcccagaa tcatctcgcc atcctgaaca tccaggcata | 1140 |
| cagtaggaga gctctagcca gccgcctgtc atcagcataa tacattcata tctacaatat | 1200 |
| ggcaaattca tatcctccct cactgaatta ttgatggact ctgcacttt aaaaaaatca | 1260 |
| atagaccagg ggtggagctg gagttaaaag aagcctttaa aagtctgctc ttcttgtttt | 1320 |
| tgctgttttg aataggagca gataaagctt tccccgctgg tttgaataag tcaagcccag | 1380 |
| ggctaggtcg gctgtgattg gccagagctg ggaaaatgtg gttatgatgc aaacgcaagc | 1440 |
| aaatataacc cagtgtctgt gtgctgtgtg gccattgctg aaacaggctt caggacccga | 1500 |
| ggtcgcctgc ttcgggaccg ctcgtcagta cttcacctgc tgctttgctg ggaaagggag | 1560 |
| aacagagggt caggtaaggt ctactgtgtg tgtccttgtc agctgaaggt gaggggacag | 1620 |
| gggtcacgcc ttc | 1633 |

<210> SEQ ID NO 6
<211> LENGTH: 1460
<212> TYPE: DNA
<213> ORGANISM: Homo sapiens

<400> SEQUENCE: 6

| | | | | | |
|---|---|---|---|---|---|
| gcagcacagg | gtggggcagc | acaagttatc | aaattaaatt | ctcaaacact | ggctgctccg | 60 |
| caccattgcc | ttgctttagt | cctgctacag | cagtagacaa | agcgagtctg | ctttgagctt | 120 |
| tatggttttt | tgccaaagtc | catactagat | ggcgcatgct | ctccaaactt | ggctttgtcc | 180 |
| atcaaggttc | aagaaaacaa | tggtcagaca | tgttcctctt | aacaaacagt | atgtccccaa | 240 |
| acagcaaaaa | tgcatacagt | cctttctggg | tgaattttta | aatcttacat | aaatccatca | 300 |
| accccatcct | tttttccttg | cctcttggga | gaaattaatc | tagctttaca | ttaattatgc | 360 |
| atgttatcag | atttcaagct | ccttgagagc | aggtatttta | attctataaa | gcctctacgt | 420 |
| ggccttggac | atgggtaggt | gcttaattac | ccaagatgct | ccttgaatac | agatggtaca | 480 |
| cgacctacac | agacttagat | ctttaccact | tccccctct | ccccaccctg | acttgctcaa | 540 |
| tcctgaagga | actggagacg | tctaagtgtc | tgaggttcac | gcttccacac | agaagcttgg | 600 |
| gtctgtgtgg | gagggaaaaa | ggaagccatc | tgtccgcagg | ccagaccagg | ccacaccctg | 660 |
| ctagcaccca | gaacccttg | tcccaggccc | agccctgcca | ttttactttc | cttgcatctg | 720 |
| gaaagcacag | gaatatagt | agtgacaaaa | gaaggaaggg | ttgtttgagt | ttaagaatag | 780 |
| tttactctaa | aaaaaaaaa | aaaaaaaaa | aaaggacaaa | agccaaagag | aaggtcaaag | 840 |
| ttgactgtgg | agaaggcctt | gcaagcaggg | aacttgggaa | gaattggaat | gagagtgaga | 900 |
| gaaggcaact | gagtttggaa | atattttttc | tgactagctt | ttctttccaa | atgccactga | 960 |
| acttagattg | gtttaggaag | ggttgtagta | catcaaagtg | gctagaagca | caggtttggg | 1020 |
| gatcagataa | ggatttcatt | ctagagtgtg | atcttgtaca | agttattcag | cctttgcaaa | 1080 |
| cctcagattc | acacaatgta | agatgaagaa | actcaccttc | tgaaaattag | agataacata | 1140 |
| tgcaaagtga | atcaatacag | ggcttaacat | atttatcacc | cctttggtaa | ataaccatga | 1200 |
| cgattaccag | agctcttaag | ggcaatggca | ggtgggaagc | agaactcatg | ggtggtaatc | 1260 |
| cccaggccag | ccaggctcac | catgtgcact | tggacaagtc | cttgccccca | tcattgtgaa | 1320 |
| atggtgcagg | gatgcaccat | gagggtgtgg | caggatggct | gacaacagac | tgggaagcag | 1380 |
| ctcggcagaa | aaactggatt | gatgcccact | atggcaagag | atatcatctc | ccctcttgtt | 1440 |
| ctgtgatgtt | tcagtcctgg | | | | | 1460 |

<210> SEQ ID NO 7
<211> LENGTH: 351
<212> TYPE: DNA
<213> ORGANISM: artificial
<220> FEATURE:
<223> OTHER INFORMATION: VAMP2 Antisense

<400> SEQUENCE: 7

| | | | | | |
|---|---|---|---|---|---|
| ttaagtgctg | aagtaaacta | tgatgatgat | gaggatgatg | gcgcaaatca | ctcccaagat | 60 |
| gatcatcatc | ttgaggtttt | tccaccagta | tttgcgcttg | agcttggctg | cgcttgtttc | 120 |
| aaactgggag | gcccccgcct | ggagtgcatc | tgcacggtcg | tccagctccg | acagcttctg | 180 |
| gtctcgctcc | aggaccttgt | ccacgttcac | cctcatgatg | tccaccacct | catccacctg | 240 |
| ggcctgggtc | tgctgcagtc | tcctgttact | ggtgaggttt | ggaggggtg | caggggacc | 300 |
| accctccca | gccggggcag | cagggggggc | cgtggcagcg | gtagcagaca | t | 351 |

<210> SEQ ID NO 8
<211> LENGTH: 621
<212> TYPE: DNA
<213> ORGANISM: artificial
<220> FEATURE:
<223> OTHER INFORMATION: SNAP25 Antisense

<400> SEQUENCE: 8

| | |
|---|---|
| ttaaccactt cccagcatct ttgttgcacg ttggttggcc tcatcaattc tggttttgtt | 60 |
| ggaatcagcc ttctccatga tcctgtcgat ctggcgattc tgtgtatcga tctcattgcc | 120 |
| catatccagg gccatgtgac ggaggttccc gatgatgccg ctcacctgct ctaggttttc | 180 |
| atccatttca ttttctcggg catcatttgt taccctgcgg atgaagccgc cactgatggc | 240 |
| catctgctcc cgttcgtcca ctacacgagc aggctggctg gccaccactc cgtcctgatt | 300 |
| attgccccag gctttttttgt aagcatcact tgatttaagc ttgttacaag acatatgaa | 360 |
| aaggccacag catttcccta aatcttttaa attttttctca gcctccttca tgtcttggtt | 420 |
| gatatggttc atgccttctt cgacacgatc gagttgttct ccttgttcat ccaacataac | 480 |
| caaagtcctg ataccagcat ctttactctc ttcaaccagt tgcagcatac gacgggtgct | 540 |
| ttccagcgac tcatcagcca actggtcagc ccttcgctgc atctcctcca gctcattgcg | 600 |
| catgtctgcg tcttcggcca t | 621 |

<210> SEQ ID NO 9
<211> LENGTH: 840
<212> TYPE: DNA
<213> ORGANISM: artificial
<220> FEATURE:
<223> OTHER INFORMATION: STX Antisense

<400> SEQUENCE: 9

| | |
|---|---|
| ttaattcagg ccaacggaaa gtccaataat caatgctaaa atgcccagca acacaactac | 60 |
| tagcacaatg ataattatca atttcttccg ggcctgactc tggtatttca cagcttttttt | 120 |
| gctttcatct cgtgccttct ccacgtggtc cactgtgtgc atgacattca actctatgtt | 180 |
| atctaacatc tcaccctgat tctccaccag catggcgatg tccataaaca tgtcgtgaag | 240 |
| ctccttgatg ctgctctcca gcctcacaat gtccttgtgt cgtccctcaa tctcactgag | 300 |
| ggcttgcttg gaaatctgtg agtcaatgat cccagaagtg aagatggccg ggttgccact | 360 |
| ctccaacatc tcctccagct cctcatcggt tgtcttttttg ccagtaattt cgagctgccg | 420 |
| ctggattcgc cctttgctgc gttctcggaa gtccacttga gcttcattgt atttggtcat | 480 |
| cacctccaca aacttccgag aaaggacaga gtgctgggat ttccgaatcc gaaggtctgc | 540 |
| cgatgacctg acctcatctt cttcaatatg cttctccatg ctcttcagtt tgttccggac | 600 |
| gttgttggcc ctttttcttaa tctcagtgct gagctgctct aggtcatcct tggttttttgg | 660 |
| ctctggaatc ggtgcagaga gaatgatact gtagagtttc ttagcctcct ctacatgttc | 720 |
| tgagatcttg tcaatgttaa gccgagtttc ctcaatctca gaaagaact cgtccataaa | 780 |
| agccgtgttg tcgatagcaa tctcaaccgc atcagtatca tcatcctgtg tcagttgcat | 840 |

<210> SEQ ID NO 10
<211> LENGTH: 457
<212> TYPE: PRT
<213> ORGANISM: Artificial Sequence
<220> FEATURE:
<223> OTHER INFORMATION: Light chain of botulinum neurotoxin A

```
<400> SEQUENCE: 10

Met His His His His His Gln Phe Val Asn Lys Gln Phe Asn Tyr
1               5                   10                  15

Lys Asp Pro Val Asn Gly Val Asp Ile Ala Tyr Ile Lys Ile Pro Asn
            20                  25                  30

Val Gly Gln Met Gln Pro Val Lys Ala Phe Lys Ile His Asn Lys Ile
            35                  40                  45

Trp Val Ile Pro Glu Arg Asp Thr Phe Thr Asn Pro Glu Glu Gly Asp
    50                  55                  60

Leu Asn Pro Pro Glu Ala Lys Gln Val Pro Val Ser Tyr Tyr Asp
65                  70                  75                  80

Ser Thr Tyr Leu Ser Thr Asp Asn Glu Lys Asp Asn Tyr Leu Lys Gly
                85                  90                  95

Val Thr Lys Leu Phe Glu Arg Ile Tyr Ser Thr Asp Leu Gly Arg Met
            100                 105                 110

Leu Leu Thr Ser Ile Val Arg Gly Ile Pro Phe Trp Gly Gly Ser Thr
        115                 120                 125

Ile Asp Thr Glu Leu Lys Val Ile Asp Thr Asn Cys Ile Asn Val Ile
130                 135                 140

Gln Pro Asp Gly Ser Tyr Arg Ser Glu Glu Leu Asn Leu Val Ile Ile
145                 150                 155                 160

Gly Pro Ser Ala Asp Ile Ile Gln Phe Glu Cys Lys Ser Phe Gly His
            165                 170                 175

Glu Val Leu Asn Leu Thr Arg Asn Gly Tyr Gly Ser Thr Gln Tyr Ile
        180                 185                 190

Arg Phe Ser Pro Asp Phe Thr Phe Gly Phe Glu Glu Ser Leu Glu Val
    195                 200                 205

Asp Thr Asn Pro Leu Leu Gly Ala Gly Lys Phe Ala Thr Asp Pro Ala
210                 215                 220

Val Thr Leu Ala His Glu Leu Ile His Ala Gly His Arg Leu Tyr Gly
225                 230                 235                 240

Ile Ala Ile Asn Pro Asn Arg Val Phe Lys Val Asn Thr Asn Ala Tyr
            245                 250                 255

Tyr Glu Met Ser Gly Leu Glu Val Ser Phe Glu Glu Leu Arg Thr Phe
        260                 265                 270

Gly Gly His Asp Ala Lys Phe Ile Asp Ser Leu Gln Glu Asn Glu Phe
    275                 280                 285

Arg Leu Tyr Tyr Tyr Asn Lys Phe Lys Asp Ile Ala Ser Thr Leu Asn
290                 295                 300

Lys Ala Lys Ser Ile Val Gly Thr Thr Ala Ser Leu Gln Tyr Met Lys
305                 310                 315                 320

Asn Val Phe Lys Glu Lys Tyr Leu Leu Ser Glu Asp Thr Ser Gly Lys
            325                 330                 335

Phe Ser Val Asp Lys Leu Lys Phe Asp Lys Leu Tyr Lys Met Leu Thr
        340                 345                 350

Glu Ile Tyr Thr Glu Asp Asn Phe Val Lys Phe Phe Lys Val Leu Asn
    355                 360                 365

Arg Lys Thr Tyr Leu Asn Phe Asp Lys Ala Val Phe Lys Ile Asn Ile
370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
            405                 410                 415
```

Met Asn Phe Thr Lys Leu Lys Asn Phe Thr Gly Leu Phe Glu Phe Tyr
            420                 425                 430

Lys Leu Leu Cys Val Arg Gly Ile Ile Thr Ser Lys Thr Lys Ser Leu
            435                 440                 445

Asp Lys Gly Tyr Asn Lys Ala Leu Asn
            450                 455

<210> SEQ ID NO 11
<211> LENGTH: 1374
<212> TYPE: DNA
<213> ORGANISM: Artificial Sequence
<220> FEATURE:
<223> OTHER INFORMATION: Light chain of botulinum neurotoxin A

<400> SEQUENCE: 11

```
atgcaccacc accaccacca ccagttcgtg aacaagcagt tcaactacaa ggaccccgtg      60
aacggcgtgg acatcgccta catcaagatc cccaacgtgg ccagatgca  gcccgtgaag     120
gccttcaaga tccacaacaa gatctgggtg atccccgaga gagacacctt caccaacccc     180
gaggagggcg acctgaaccc cccccccgag gccaagcagg tgcccgtgag ctactacgac     240
agcacctacc tgagcaccga caacgagaag acaactacc  tgaagggcgt gaccaagctg     300
ttcgagagaa tctacagcac cgacctgggc agaatgctgc tgaccagcat cgtgagaggc     360
atccccttct ggggcggcag caccatcgac accgagctga aggtgatcga caccaactgc     420
atcaacgtga tccagcccga cggcagctac agaagcgagg agctgaacct ggtgatcatc     480
ggccccagcg ccgacatcat ccagttcgag tgcaagagct tcggccacga ggtgctgaac     540
ctgaccagaa acggctacgg cagcacccag tacatcagat cagccccga  cttcaccttc     600
ggcttcgagg agagcctgga ggtggacacc aaccccctgc tgggcgccgg caagttcgcc     660
accgaccccg ccgtgaccct ggcccacgag ctgatccacg ccggccacag actgtacggc     720
atcgccatca cccccaacag agtgttcaag gtgaacacca cgcctacta  cgagatgagc     780
ggcctggagg tgagcttcga ggagctgaga accttcggcg gccacgacgc caagttcatc     840
gacagcctgc aggagaacga gttcagactg tactactaca acaagttcaa ggacatcgcc     900
agcaccctga caaggccaa  gagcatcgtg gcaccaccg  ccagcctgca gtacatgaag     960
aacgtgttca ggagaagta  cctgctgagc gaggacacca cgcggcaagtt cagcgtggac    1020
aagctgaagt cgacaagct  gtacaagatg ctgaccgaga tctacaccga ggacaacttc    1080
gtgaagttct tcaaggtgct gaacagaaag acctacctga acttcgacaa ggccgtgttc    1140
aagatcaaca tcgtgcccaa ggtgaactac accatctacg acggcttcaa cctgagaaac    1200
accaacctgg ccgccaactt caacggccag aacaccgaga tcaacaacat gaacttcacc    1260
aagctgaaga acttcaccgg cctgttcgag ttctacaagc tgctgtgcgt gagaggcatc    1320
atcaccagca agaccaagag cctggacaag ggctacaaca aggccctgaa ctga          1374
```

<210> SEQ ID NO 12
<211> LENGTH: 447
<212> TYPE: PRT
<213> ORGANISM: Artificial Sequence
<220> FEATURE:
<223> OTHER INFORMATION: Light chain of botulinum neurotoxin B

<400> SEQUENCE: 12

Met His His His His His His Pro Val Thr Ile Asn Asn Phe Asn Tyr
1               5                   10                  15

-continued

Asn Asp Pro Ile Asp Asn Asn Ile Ile Met Met Glu Pro Pro Phe
            20                  25                  30

Ala Arg Gly Thr Gly Arg Tyr Tyr Lys Ala Phe Lys Ile Thr Asp Arg
        35                  40                  45

Ile Trp Ile Ile Pro Glu Arg Tyr Thr Phe Gly Tyr Lys Pro Glu Asp
    50                  55                  60

Phe Asn Lys Ser Ser Gly Ile Phe Asn Arg Asp Val Cys Glu Tyr Tyr
65                  70                  75                  80

Asp Pro Asp Tyr Leu Asn Thr Asn Asp Lys Lys Asn Ile Phe Leu Gln
                85                  90                  95

Thr Met Ile Lys Leu Phe Asn Arg Ile Lys Ser Lys Pro Leu Gly Glu
            100                 105                 110

Lys Leu Leu Glu Met Ile Ile Asn Gly Ile Pro Tyr Leu Gly Asp Arg
        115                 120                 125

Arg Val Pro Leu Glu Glu Phe Asn Thr Asn Ile Ala Ser Val Thr Val
    130                 135                 140

Asn Lys Leu Ile Ser Asn Pro Gly Glu Val Glu Arg Lys Lys Gly Ile
145                 150                 155                 160

Phe Ala Asn Leu Ile Ile Phe Gly Pro Gly Pro Val Leu Asn Glu Asn
                165                 170                 175

Glu Thr Ile Asp Ile Gly Ile Gln Asn His Phe Ala Ser Arg Glu Gly
            180                 185                 190

Phe Gly Gly Ile Met Gln Met Lys Phe Cys Pro Glu Tyr Val Ser Val
        195                 200                 205

Phe Asn Asn Val Gln Glu Asn Lys Gly Ala Ser Ile Phe Asn Arg Arg
210                 215                 220

Gly Tyr Phe Ser Asp Pro Ala Leu Ile Leu Met His Glu Leu Ile His
225                 230                 235                 240

Val Leu His Gly Leu Tyr Gly Ile Lys Val Asp Asp Leu Pro Ile Val
                245                 250                 255

Pro Asn Glu Lys Lys Phe Phe Met Gln Ser Thr Asp Ala Ile Gln Ala
            260                 265                 270

Glu Glu Leu Tyr Thr Phe Gly Gly Gln Asp Pro Ser Ile Ile Thr Pro
        275                 280                 285

Ser Thr Asp Lys Ser Ile Tyr Asp Lys Val Leu Gln Asn Phe Arg Gly
    290                 295                 300

Ile Val Asp Arg Leu Asn Lys Val Leu Val Cys Ile Ser Asp Pro Asn
305                 310                 315                 320

Ile Asn Ile Asn Ile Tyr Lys Asn Lys Phe Lys Asp Lys Tyr Lys Phe
                325                 330                 335

Val Glu Asp Ser Glu Gly Lys Tyr Ser Ile Asp Val Glu Ser Phe Asp
            340                 345                 350

Lys Leu Tyr Lys Ser Leu Met Phe Gly Phe Thr Glu Thr Asn Ile Ala
        355                 360                 365

Glu Asn Tyr Lys Ile Lys Thr Arg Ala Ser Tyr Phe Ser Asp Ser Leu
    370                 375                 380

Pro Pro Val Lys Ile Lys Asn Leu Leu Asp Asn Glu Ile Tyr Thr Ile
385                 390                 395                 400

Glu Glu Gly Phe Asn Ile Ser Asp Lys Asp Met Glu Lys Glu Tyr Arg
                405                 410                 415

Gly Gln Asn Lys Ala Ile Asn Lys Gln Ala Tyr Glu Glu Ile Ser Lys
            420                 425                 430

Glu His Leu Ala Val Tyr Lys Ile Gln Met Cys Lys Ser Val Lys

<210> SEQ ID NO 13
<211> LENGTH: 1344
<212> TYPE: DNA
<213> ORGANISM: Artificial Sequence
<220> FEATURE:
<223> OTHER INFORMATION: Light chain of botulinum neurotoxin B

<400> SEQUENCE: 13

```
atgcaccacc atcatcacca ccctgttacc atcaataact ttaactataa cgatccaata      60
gacaacaaca acatcatcat gatggagccc ccctttgcta gagggactgg tcggtactac     120
aaagctttta agatcaccga tcggatttgg attatccctg aacggtatac atttggctac     180
aaacccgaag acttcaataa atcttctggt attttcaatc gagacgtgtg tgaatactat     240
gatcccgact acctcaacac taacgataaa agaacatttc tgcagac aatgattaag         300
ctgttcaatc ggatcaagag taaacccttg ggtgaaaaac ttctggagat gattatcaac     360
ggtataccct acctgggcga caggagggtg ccactcgaag agttcaatac aaacatagcc     420
agcgtgaccg tgaataagct gatcagtaac ccaggcgaag ttgagcggaa gaagggaatt     480
ttcgctaacc tcatcatctt cggaccagga cctgtcctta cgagaatgac acaattgat      540
attggaatcc agaaccattt cgcatcacgc gaaggcttcg ggggtatcat gcagatgaag     600
ttctgcccgg agtatgtctc tgtgttcaac aacgtgcagg aaaataaggg agcgagcatt     660
ttcaatcgca gaggctattt ttccgacccc gcgctcatcc ttatgcacga gctgatccat     720
gtcctgcacg gactgtacgg catcaaagtc gacgatttgc caattgtgcc caacgaaaag     780
aagttcttca tgcagtccac cgacgctatc aagcggagg agctctatac ttttggcgga     840
caggacccctt ctatcatcac tccatctaca gataagagta tatacgataa ggttctccag     900
aatttccgcg aatcgtcga ccgccttaac aaggtgctgg tttgtatttc gacccaaac      960
atcaatataa atatctataa gaacaagttc aaagataaat ataagttcgt ggaggacagc    1020
gagggtaagt actctattga tgtggagagc tttgataaac tgtacaagtc tctcatgttc    1080
ggtttcacag agactaatat cgccgagaac tataagataa aaacccgggc aagctatttc    1140
tccgatagcc tgccaccggt taagattaag aacctgctgg acaatgaaat ataccatc       1200
gaggaaggat ttaacatctc cgacaaggac atggagaaaa ataccgggga cagaacaag     1260
gccattaata gcaggcttta cgaggagatt agcaaggagc acctggctgt gtacaaaatc    1320
cagatgtgca agtcagtgaa gtag                                           1344
```

<210> SEQ ID NO 14
<211> LENGTH: 457
<212> TYPE: PRT
<213> ORGANISM: Artificial Sequence
<220> FEATURE:
<223> OTHER INFORMATION: Light chain of botulinum neurotoxin C1

<400> SEQUENCE: 14

```
Met His His His His His His Pro Ile Thr Ile Asn Asn Phe Asn Tyr
  1               5                  10                  15

Ser Asp Pro Val Asp Asn Lys Asn Ile Leu Tyr Leu Asp Thr His Leu
             20                  25                  30

Asn Thr Leu Ala Asn Glu Pro Glu Lys Ala Phe Arg Ile Thr Gly Asn
         35                  40                  45

Ile Trp Val Ile Pro Asp Arg Phe Ser Arg Asn Ser Asn Pro Asn Leu
     50                  55                  60
```

```
Asn Lys Pro Pro Arg Val Thr Ser Pro Lys Ser Gly Tyr Tyr Asp Pro
 65                  70                  75                  80

Asn Tyr Leu Ser Thr Asp Ser Asp Lys Asp Pro Phe Leu Lys Glu Ile
             85                  90                  95

Ile Lys Leu Phe Lys Arg Ile Asn Ser Arg Glu Ile Gly Glu Leu
        100                 105                 110

Ile Tyr Arg Leu Ser Thr Asp Ile Pro Phe Pro Gly Asn Asn Asn Thr
        115                 120                 125

Pro Ile Asn Thr Phe Asp Phe Asp Val Asp Phe Asn Ser Val Asp Val
130                 135                 140

Lys Thr Arg Gln Gly Asn Asn Trp Val Lys Thr Gly Ser Ile Asn Pro
145                 150                 155                 160

Ser Val Ile Ile Thr Gly Pro Arg Glu Asn Ile Ile Asp Pro Glu Thr
                165                 170                 175

Ser Thr Phe Lys Leu Thr Asn Asn Thr Phe Ala Ala Gln Glu Gly Phe
            180                 185                 190

Gly Ala Leu Ser Ile Ile Ser Ile Ser Pro Arg Phe Met Leu Thr Tyr
            195                 200                 205

Ser Asn Ala Thr Asn Asp Val Gly Glu Gly Arg Phe Ser Lys Ser Glu
210                 215                 220

Phe Cys Met Asp Pro Ile Leu Ile Leu Met His Glu Leu Asn His Ala
225                 230                 235                 240

Met His Asn Leu Tyr Gly Ile Ala Ile Pro Asn Asp Gln Thr Ile Ser
                245                 250                 255

Ser Val Thr Ser Asn Ile Phe Tyr Ser Gln Tyr Asn Val Lys Leu Glu
            260                 265                 270

Tyr Ala Glu Ile Tyr Ala Phe Gly Gly Pro Thr Ile Asp Leu Ile Pro
        275                 280                 285

Lys Ser Ala Arg Lys Tyr Phe Glu Glu Lys Ala Leu Asp Tyr Tyr Arg
290                 295                 300

Ser Ile Ala Lys Arg Leu Asn Ser Ile Thr Thr Ala Asn Pro Ser Ser
305                 310                 315                 320

Phe Asn Lys Tyr Ile Gly Glu Tyr Lys Gln Lys Leu Ile Arg Lys Tyr
                325                 330                 335

Arg Phe Val Val Glu Ser Ser Gly Glu Val Thr Val Asn Arg Asn Lys
            340                 345                 350

Phe Val Glu Leu Tyr Asn Glu Leu Thr Gln Ile Phe Thr Glu Phe Asn
        355                 360                 365

Tyr Ala Lys Ile Tyr Asn Val Gln Asn Arg Lys Ile Tyr Leu Ser Asn
        370                 375                 380

Val Tyr Thr Pro Val Thr Ala Asn Ile Leu Asp Asp Asn Val Tyr Asp
385                 390                 395                 400

Ile Gln Asn Gly Phe Asn Ile Pro Lys Ser Asn Leu Asn Val Leu Phe
                405                 410                 415

Met Gly Gln Asn Leu Ser Arg Asn Pro Ala Leu Arg Lys Val Asn Pro
            420                 425                 430

Glu Asn Met Leu Tyr Leu Phe Thr Lys Phe Cys His Lys Ala Ile Asp
            435                 440                 445

Gly Arg Ser Leu Tyr Asn Lys Thr Leu
450                 455

<210> SEQ ID NO 15
<211> LENGTH: 1374
```

<212> TYPE: DNA
<213> ORGANISM: Artificial Sequence
<220> FEATURE:
<223> OTHER INFORMATION: Light chain of botulinum neurotoxin C1

<400> SEQUENCE: 15

```
atgcaccacc accaccacca ccccatcacc atcaacaact tcaactacag cgaccccgtg      60
gacaacaaga acatcctgta cctggacacc cacctgaaca ccctggccaa cgagcccgag     120
aaggccttca gaatcaccgg caacatctgg gtgatcccg acagattcag cagaaacagc     180
aaccccaacc tgaacaagcc ccccagagtg accagcccca gagcggcta ctacgacccc     240
aactacctga gcaccgacag cgacaaggac cccttcctga aggagatcat caagctgttc     300
aagagaatca acagcagaga gatcggcgag gagctgatct acagactgag caccgacatc     360
cccttccccg gcaacaacaa caccccccatc aacaccttcg acttcgacgt ggacttcaac     420
agcgtggacg tgaagaccag acagggcaac aactgggtga gaccggcag catcaacccc     480
agcgtgatca tcaccggccc cagagagaac atcatcgacc ccgagaccag caccttcaag     540
ctgaccaaca cacccttcgc cgcccaggag ggcttcggcg ccctgagcat catcagcatc     600
agccccagat tcatgctgac ctacagcaac gccaccaacg acgtgggcga gggcagattc     660
agcaagagcg agttctgcat ggaccccatc ctgatcctga tgcacgagct gaaccacgcc     720
atgcacaacc tgtacggcat cgccatcccc aacgaccaga ccatcagcag cgtgaccagc     780
aacatcttct acagccagta caacgtgaag ctggagtacg ccgagatcta cgccttcggc     840
ggcccccacca tcgacctgat ccccaagagc gccagaaagt acttcgagga aggccctg     900
gactactaca agcatcgc caagagactg aacagcatca ccaccgccaa ccccagcagc     960
ttcaacaagt acatcggcga gtacaagcag aagctgatca gaaagtacag attcgtggtg    1020
gagagcagcg gcgaggtgac cgtgaacaga acaagttcg tggagctgta caacgagctg    1080
acccagatct tcaccgagtt caactacgcc aagatctaca cgtgcagaa cagaaagatc    1140
tacctgagca acgtgtacac ccccgtgacc gccaacatcc tggacgacaa cgtgtacgac    1200
atccagaacg gcttcaacat ccccaagagc aacctgaacg tgctgttcat gggccagaac    1260
ctgagcagaa accccgccct gagaaaggtg aaccccgaga catgctgta cctgttcacc    1320
aagttctgcc acaaggccat cgacggcaga agcctgtaca caagaccct gtga          1374
```

<210> SEQ ID NO 16
<211> LENGTH: 429
<212> TYPE: PRT
<213> ORGANISM: Artificial Sequence
<220> FEATURE:
<223> OTHER INFORMATION: Light chain of botulinum neurotoxin E3

<400> SEQUENCE: 16

Met His His His His His His Pro Lys Ile Asn Ser Phe Asn Tyr Asn
1               5                   10                  15

Asp Pro Val Asn Asp Arg Thr Ile Leu Tyr Ile Lys Pro Gly Gly Cys
            20                  25                  30

Gln Glu Phe Tyr Lys Ser Phe Asn Ile Met Lys Asn Ile Trp Ile Ile
        35                  40                  45

Pro Glu Arg Asn Val Ile Gly Thr Thr Pro Gln Asp Phe His Pro Pro
    50                  55                  60

Thr Ser Leu Lys Asn Gly Asp Ser Ser Tyr Tyr Asp Pro Asn Tyr Leu
65                  70                  75                  80

Gln Ser Asp Glu Glu Lys Asp Arg Phe Leu Lys Ile Val Thr Lys Ile 85                  90                  95
Phe Asn Arg Ile Asn Asn Leu Ser Gly Gly Ile Leu Leu Glu Glu
            100                 105                 110

Leu Ser Lys Ala Asn Pro Tyr Leu Gly Asn Asp Asn Thr Pro Asp Asn
            115                 120                 125

Gln Phe His Ile Gly Asp Ala Ser Ala Val Glu Ile Lys Phe Ser Asn
        130                 135                 140

Gly Ser Gln His Ile Leu Leu Pro Asn Val Ile Met Gly Ala Glu
145                 150                 155                 160

Pro Asp Leu Phe Glu Thr Asn Ser Ser Asn Ile Ser Leu Arg Asn Asn
                165                 170                 175

Tyr Met Pro Ser Asn His Gly Phe Gly Ser Ile Ala Ile Val Thr Phe
            180                 185                 190

Ser Pro Glu Tyr Ser Phe Arg Phe Asn Asp Asn Ser Ile Asn Glu Phe
        195                 200                 205

Ile Gln Asp Pro Ala Leu Thr Leu Met His Glu Leu Ile His Ser Leu
    210                 215                 220

His Gly Leu Tyr Gly Ala Lys Gly Ile Thr Thr Thr Cys Ile Ile Thr
225                 230                 235                 240

Gln Gln Gln Asn Pro Leu Ile Thr Asn Arg Lys Gly Ile Asn Ile Glu
                245                 250                 255

Glu Phe Leu Thr Phe Gly Gly Asn Asp Leu Asn Ile Ile Thr Val Ala
            260                 265                 270

Gln Tyr Asn Asp Ile Tyr Thr Asn Leu Leu Asn Asp Tyr Arg Lys Ile
        275                 280                 285

Ala Ser Lys Leu Ser Lys Val Gln Val Ser Asn Pro Gln Leu Asn Pro
    290                 295                 300

Tyr Lys Asp Ile Phe Gln Glu Lys Tyr Gly Leu Asp Lys Asp Ala Ser
305                 310                 315                 320

Gly Ile Tyr Ser Val Asn Ile Asn Lys Phe Asp Asp Ile Leu Lys Lys
                325                 330                 335

Leu Tyr Ser Phe Thr Glu Phe Asp Leu Ala Thr Lys Phe Gln Val Lys
            340                 345                 350

Cys Arg Glu Thr Tyr Ile Gly Gln Tyr Lys Tyr Phe Lys Leu Ser Asn
        355                 360                 365

Leu Leu Asn Asp Ser Ile Tyr Asn Ile Ser Glu Gly Tyr Asn Ile Asn
    370                 375                 380

Asn Leu Lys Val Asn Phe Arg Gly Gln Asn Ala Asn Leu Asn Pro Arg
385                 390                 395                 400

Ile Ile Lys Pro Ile Thr Gly Arg Gly Leu Val Lys Lys Ile Ile Arg
                405                 410                 415

Phe Cys Lys Asn Ile Val Ser Val Lys Gly Ile Arg Lys
            420                 425

<210> SEQ ID NO 17
<211> LENGTH: 1290
<212> TYPE: DNA
<213> ORGANISM: Artificial Sequence
<220> FEATURE:
<223> OTHER INFORMATION: Light chain of botulinum neurotoxin E3

<400> SEQUENCE: 17
atgcaccatc accatcacca tcccaagatt aattctttca actataatga tccagtcaac    60
gacaggacca ttctctacat caagccgggc ggctgtcagg aattctacaa atcatttaac   120

```
atcatgaaga atatttggat catacctgaa agaaatgtga ttggaaccac accccaggat    180
ttccaccccc caacaagctt gaaaaacgga gacagttcct actatgaccc taattatctt    240
cagagcgatg aggagaaaga cagattcctg aagatcgtga ccaaaatctt caaccggatc    300
aacaataatc tctccggggg tattttgctg gaggagctgt caaaggcgaa tccttacctt    360
ggcaatgata acacaccgga caatcagttc cacataggag atgcttcagc tgtcgagatt    420
aaattcagca acggttccca gcatattctg cttccgaatg tcattattat gggagccgag    480
ccagacctgt tcgagaccaa ttcttccaac ataagcttga ggaataatta catgccatct    540
aaccacggtt tgggtcaat cgcaattgtc acttttagtc cggagtacag cttccgcttt    600
aatgacaaca gcatcaatga attcatacag gatcccgctc tgacactcat gcatgagctg    660
atccactctc tgcatggcct gtatggtgct aagggggatca ccaccacatg tattatcacg    720
cagcagcaaa atccactgat tacaaacagg aaaggcataa atattgaaga gttcctgaca    780
ttcggcggca atgaccttaa cattatcact gtggctcagt ataacgatat ttatactaat    840
ctgctgaacg actataggaa aatcgcttca aaactgagca aggtgcaggt ctcaaaccca    900
cagttgaatc catataagga tatctttcag gaaaagtatg ggttggacaa ggatgcttca    960
ggcatctaca gtgtcaatat caacaaattc gacgacatct tgaagaaact gtatagcttt   1020
acggagttcg atctggcgac taagttccaa gtgaaatgcc gggagacata catcggtcaa   1080
tataaatatt ttaaactgtc caaccttctc aatgatagca tctacaatat cagtgaagga   1140
tataacatta taaacctgaa agtgaatttc cgaggccaga acgccaattt gaaccccgg    1200 attatcaagc ccattacagg acgggggctg gtgaagaaaa ttattcgctt ttgtaagaat    1260
atcgtgtcag tgaagggaat aagaaagtag                                    1290
```

<210> SEQ ID NO 18
<211> LENGTH: 442
<212> TYPE: PRT
<213> ORGANISM: Artificial Sequence
<220> FEATURE:
<223> OTHER INFORMATION: Light chain of botulinum neurotoxin F1

<400> SEQUENCE: 18

```
Met His His His His His Pro Val Val Ile Asn Ser Phe Asn Tyr
1               5                   10                  15

Asn Asp Pro Val Asn Asp Asp Thr Ile Leu Tyr Met Gln Ile Pro Tyr
            20                  25                  30

Glu Glu Lys Ser Lys Lys Tyr Tyr Lys Ala Phe Glu Ile Met Arg Asn
        35                  40                  45

Val Trp Ile Ile Pro Glu Arg Asn Thr Ile Gly Thr Asp Pro Ser Asp
    50                  55                  60

Phe Asp Pro Pro Ala Ser Leu Glu Asn Gly Ser Ser Ala Tyr Tyr Asp
65                  70                  75                  80

Pro Asn Tyr Leu Thr Thr Asp Ala Glu Lys Asp Arg Tyr Leu Lys Thr
                85                  90                  95

Thr Ile Lys Leu Phe Lys Arg Ile Asn Ser Asn Pro Ala Gly Glu Val
            100                 105                 110

Leu Leu Gln Glu Ile Ser Tyr Ala Lys Pro Tyr Leu Gly Asn Glu His
        115                 120                 125

Thr Pro Ile Asn Glu Phe His Pro Val Thr Arg Thr Thr Ser Val Asn
    130                 135                 140

Ile Lys Ser Ser Thr Asn Val Lys Ser Ser Ile Ile Leu Asn Leu Leu
145                 150                 155                 160
```

Val Leu Gly Ala Gly Pro Asp Ile Phe Glu Asn Ser Ser Tyr Pro Val
            165                 170                 175

Arg Lys Leu Met Asp Ser Gly Val Tyr Asp Pro Ser Asn Asp Gly
        180                 185                 190

Phe Gly Ser Ile Asn Ile Val Thr Phe Ser Pro Glu Tyr Glu Tyr Thr
            195                 200                 205

Phe Asn Asp Ile Ser Gly Gly Tyr Asn Ser Ser Thr Glu Ser Phe Ile
            210                 215                 220

Ala Asp Pro Ala Ile Ser Leu Ala His Glu Leu Ile His Ala Leu His
225                 230                 235                 240

Gly Leu Tyr Gly Ala Arg Gly Val Thr Tyr Lys Glu Thr Ile Lys Val
            245                 250                 255

Lys Gln Ala Pro Leu Met Ile Ala Glu Lys Pro Ile Arg Leu Glu Glu
            260                 265                 270

Phe Leu Thr Phe Gly Gly Gln Asp Leu Asn Ile Ile Thr Ser Ala Met
            275                 280                 285

Lys Glu Lys Ile Tyr Asn Asn Leu Leu Ala Asn Tyr Glu Lys Ile Ala
            290                 295                 300

Thr Arg Leu Ser Arg Val Asn Ser Ala Pro Pro Glu Tyr Asp Ile Asn
305                 310                 315                 320

Glu Tyr Lys Asp Tyr Phe Gln Trp Lys Tyr Gly Leu Asp Lys Asn Ala
            325                 330                 335

Asp Gly Ser Tyr Thr Val Asn Glu Asn Lys Phe Asn Glu Ile Tyr Lys
            340                 345                 350

Lys Leu Tyr Ser Phe Thr Glu Ile Asp Leu Ala Asn Lys Phe Lys Val
            355                 360                 365

Lys Cys Arg Asn Thr Tyr Phe Ile Lys Tyr Gly Phe Leu Lys Val Pro
            370                 375                 380

Asn Leu Leu Asp Asp Asp Ile Tyr Thr Val Ser Glu Gly Phe Asn Ile
385                 390                 395                 400

Gly Asn Leu Ala Val Asn Asn Arg Gly Gln Asn Ile Lys Leu Asn Pro
            405                 410                 415

Lys Ile Ile Asp Ser Ile Pro Asp Lys Gly Leu Val Glu Lys Ile Val
            420                 425                 430

Lys Phe Cys Lys Ser Val Ile Pro Arg Lys
            435                 440

<210> SEQ ID NO 19
<211> LENGTH: 1329
<212> TYPE: DNA
<213> ORGANISM: Artificial Sequence
<220> FEATURE:
<223> OTHER INFORMATION: Light chain of botulinum neurotoxin F1

<400> SEQUENCE: 19
atgcaccatc atcatcacca tcccgtggtt atcaatagct ttaattataa cgatcccgtg      60
aatgatgata caattctcta catgcagatt ccatacgagg aaaagagcaa gaagtattat     120
aaagcattcg aaataatgcg gaacgtttgg attattcccg agagaaacac aatcggaacc     180
gacccgtccg attttgatcc accgcctcca ttggaaaacg gcagtagcgc ctactacgat     240
cccaattatc tcaccacaga tgctgagaag gaccgctatc tgaaaccaca atcaagctc     300 tttaagagaa tcaactctaa tccagctggc gaagtcctgc tgcaggaaat tagctacgca     360
aagccatatc tcggcaacga gcatacacct attaatgagt ccatcccgt cactcggacg      420

| | |
|---|---|
| acctctgtga acataaaaag ctctacaaac gtgaagagct ctataatact gaacctgctc | 480 |
| gtgctgggtg ctggcccaga cattttcgag aatagttcct atccagttcg aaagttgatg | 540 |
| gattctgggg gcgtgtacga tcctagcaat gacggatttg ggagtattaa tatagtcaca | 600 |
| ttcagtcccg agtatgaata caccttcaac gacatcagcg gtggctacaa ttcatcaact | 660 |
| gagagcttca ttgccgaccc agccatcagt ctggcccatg agttgatcca tgccctgcac | 720 |
| ggcctctatg gggctagagg ggttacctac aaggaaacaa ttaaagtcaa gcaggctcca | 780 |
| ctcatgatcg ctgaaaagcc cattcggctc gaggagtttc tgacattcgg cggccaggat | 840 |
| ctcaacataa tcaccagtgc tatgaaagag aagatctaca ataaccttct tgcaaattac | 900 |
| gaaaaaatcg caacacggct gtcacgggtg aatagcgctc ccctgagta cgacattaac | 960 |
| gagtataaag attacttcca gtggaaatac gggctggaca aaaatgccga cgggagctac | 1020 |
| acagtgaacg agaacaagtt taacgagatc tacaagaaac tgtactcatt taccgagatt | 1080 |
| gacctggcta ataagtttaa ggtcaagtgc agaaatactt atttcatcaa gtacggattt | 1140 |
| ttgaaagtcc ctaatctgct ggacgacgat atttatactg tgtctgaagg ttttaatatc | 1200 |
| ggaaaccttg ccgtgaataa ccgcgggcag aatataaagc ttaatcctaa gatcatcgat | 1260 |
| tcaattcctg acaaaggcct cgtcgagaaa atagtgaaat tctgcaaaag tgtgattcct | 1320 |
| agaaagtga | 1329 |

<210> SEQ ID NO 20
<211> LENGTH: 457
<212> TYPE: PRT
<213> ORGANISM: Artificial Sequence
<220> FEATURE:
<223> OTHER INFORMATION: Light chain of tetanic neurotoxin

<400> SEQUENCE: 20

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn

```
                195                 200                 205
Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala
    450                 455

<210> SEQ ID NO 21
<211> LENGTH: 1373
<212> TYPE: DNA
<213> ORGANISM: Artificial Sequence
<220> FEATURE:
<223> OTHER INFORMATION: Light chain of tetanic neurotoxin

<400> SEQUENCE: 21
atgcccatca ccatcaacaa cttccggtac agcgaccccg tgaacaacga caccatcatc      60
atgatggagc cccctactg caagggcctg gacatctact acaaggcctt caagatcacc     120
gaccggatct ggatcgtgcc cgagcggtac gagttcggca ccaagcccga ggacttcaac     180
ccccccagca gcctgatcga gggcgccagc gagtactacg accccaacta cctgcggacc     240
gacagcgaca aggaccggtt cctgcagacc atggtgaagc tgttcaaccg gatcaagaac     300
aacgtggccg cgaggcccct gctggacaag atcatcaacg ccatcccta cctgggcaac     360 agctacagcc tgctggacaa gttcgacacc aacagcaaca gcgtgagctt caacctgctg     420
gagcaggacc ccagcggcgc caccaccaag agcgccatgc tgaccaacct gatcatcttc     480
ggccccggcc ccgtgctgaa caagaacgag gtgcggggca tcgtgctgcg ggtgacaac     540 aagaactact tcccctgccg ggacggcttc ggcagcatca tgcagatggc cttctgcccc     600
```

-continued

```
gagtacgtgc ccaccttcga caacgtgatc gagaacatca ccagcctgac catcggcaag      660
agcaagtact tccaggaccc cgccctgctg ctgatgcacg agctgatcca cgtgctgcac      720
ggcctgtacg gcatgcaggt gagcagccac gagatcatcc ccagcaagca ggagatctac      780
atgcagcaca cctaccccat cagcgccgag gagctgttca ccttcggcgg ccaggacgcc      840
aacctgatca gcatcgacat caagaacgac ctgtacgaga gaccctgaa cgactacaag       900 gccatcgcca caagctgag ccaggtgacc agctgcaacg accccaacat cgacatcgac       960
agctacaagc agatctacca gcagaagtac cagttcgaca aggacagcaa cggccagtac     1020
atcgtgaacg aggacaagtt ccagatcctg tacaacagca tcatgtacgg cttcaccgag     1080
atcgagctgg gcaagaagtt caacatcaag acccggctga gctacttcag catgaaccac     1140
gaccccgtga gatccccaa cctgctggac gacaccatct acaacgacac cgagggcttc      1200
aacatcgaga gcaaggacct gaagagcgag tacaagggcc agaacatgcg ggtgaacacc     1260
aacgccttcc ggaacgtgga cggcagcggc ctggtgagca agctgatcgg cctgtgcaag     1320
aagatcatcc ccccaccaa catccgggag aacctgtaca ccggaccgc ctg              1373
```

<210> SEQ ID NO 22
<211> LENGTH: 594
<212> TYPE: PRT
<213> ORGANISM: Homo sapiens

<400> SEQUENCE: 22

```
Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
            35                  40                  45

Gly Phe Leu Gln Arg Thr Asn Ser Leu Glu Glu Lys Ser Arg Leu Val
        50                  55                  60

Ser Ala Phe Arg Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240
```

-continued

Ser Lys Asp Gly Asp Gly Ile Phe Ser Pro Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
    290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
    370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Ile Glu Arg Leu Gly Gln
            580                 585                 590

Asp Leu

<210> SEQ ID NO 23
<211> LENGTH: 1785
<212> TYPE: DNA
<213> ORGANISM: Homo sapiens

<400> SEQUENCE: 23
atggcgtctt cgaccccatc ttcgtccgca acctcctcga acgcgggagc ggaccccaat    60

-continued

| | |
|---|---|
| accactaacc tgcgccccac aacgtacgat acctggtgcg gcgtggccca tggatgcacc | 120 |
| agaaaactgg ggctcaagat ctgcggcttc ttgcaaagga ccaacagcct ggaagagaag | 180 |
| agtcgccttg tgagtgcctt cagggagagg caatcctcca agaacctgct ttcctgtgaa | 240 |
| aacagcgacc gggatgcccg cttccggcgc acagagactg acttctctaa tctgtttgct | 300 |
| agagatctgc ttccggctaa gaacggtgag gagcaaaccg tgcaattcct cctggaagtg | 360 |
| gtggacatac tcctcaacta tgtccgcaag acatttgatc gctccaccaa ggtgctggac | 420 |
| tttcatcacc cacaccagtt gctggaaggc atggagggct caacttgga gctctctgac | 480 |
| caccccgagt ccctggagca gatcctggtt gactgcagag acaccttgaa gtatgggggtt | 540 |
| cgcacaggtc atcctcgatt tttcaaccag ctctccactg gattggatat tattggccta | 600 |
| gctggagaat ggctgacatc aacggccaat accaacatgt ttacatatga aattgcacca | 660 |
| gtgtttgtcc tcatggaaca aataacactt aagaagatga gagagatagt tggatggtca | 720 |
| agtaaagatg gtgatgggat attttctcct gggggcgcca tatccaacat gtacagcatc | 780 |
| atggctgctc gctacaagta cttcccggaa gttaagacaa agggcatggc ggctgtgcct | 840 |
| aaactggtcc tcttcacctc agaacagagt cactattcca taagaaagc tggggctgca | 900 |
| cttggctttg gaactgacaa tgtgattttg ataaagtgca atgaagggg gaaataatt | 960 |
| ccagctgatt ttgaggcaaa aattcttgaa gccaaacaga agggatatgt tccctttat | 1020 |
| gtcaatgcaa ctgctggcac gactgtttat ggagcttttg atccgataca agagattgca | 1080 |
| gatatatgtg agaaatataa cctttggttg catgtcgatg ctgcctgggg aggtgggctg | 1140 |
| ctcatgtcca ggaagcaccg ccataaactc aacggcatag aaagggccaa ctcagtcacc | 1200 |
| tggaaccctc acaagatgat gggcgtgctg ttgcagtgct ctgccattct cgtcaaggaa | 1260 |
| aagggtatac tccaaggatg caaccagatg tgtgcaggat atctcttcca gccagacaag | 1320 |
| cagtatgatg tctcctacga caccggggac aaggcaattc agtgtggccg ccacgtggat | 1380 |
| atcttcaagt tctggctgat gtggaaagca aagggcacag tgggatttga aaaccagatc | 1440 |
| aacaaatgcc tggaactggc tgaataccct tatgccaaga ttaaaaacag agaagaattt | 1500 |
| gagatggttt tcaatggcga gcctgagcac acaaacgtct gttttggta tattccacaa | 1560 |
| agcctcaggg gtgtgccaga cagccctcaa cgacgggaaa agctacacaa ggtggctcca | 1620 |
| aaaatcaaag ccctgatgat ggagtcaggt acgaccatgg ttggctacca gccccaaggg | 1680 |
| gacaaggcca acttcttccg gatggtcatc tccaacccag ccgctaccca gtctgacatt | 1740 |
| gacttcctca ttgaggagat agaaagactg ggccaggatc tgtaa | 1785 |

<210> SEQ ID NO 24
<211> LENGTH: 254
<212> TYPE: PRT
<213> ORGANISM: Unknown
<220> FEATURE:
<223> OTHER INFORMATION: Saporin S6 protein

<400> SEQUENCE: 24

Met Val Thr Ser Ile Thr Leu Asp Leu Val Asn Pro Thr Ala Gly Gln
1               5                   10                  15

Tyr Ser Ser Phe Val Asp Lys Ile Arg Asn Asn Val Lys Asp Pro Asn
            20                  25                  30

Leu Lys Tyr Gly Gly Thr Asp Ile Ala Val Ile Gly Pro Pro Ser Lys
        35                  40                  45

Glu Lys Phe Leu Arg Ile Asn Phe Gln Ser Ser Arg Gly Thr Val Ser
    50                  55                  60

Leu Gly Leu Lys Arg Asp Asn Leu Tyr Val Val Ala Tyr Leu Ala Met
 65                  70                  75                  80

Asp Asn Thr Asn Val Asn Arg Ala Tyr Tyr Phe Arg Ser Glu Ile Thr
             85                  90                  95

Ser Ala Glu Ser Thr Ala Leu Phe Pro Glu Ala Thr Thr Ala Asn Gln
        100                 105                 110

Lys Ala Leu Glu Tyr Thr Glu Asp Tyr Gln Ser Ile Glu Lys Asn Ala
    115                 120                 125

Gln Ile Thr Gln Gly Asp Gln Ser Arg Lys Glu Leu Gly Leu Gly Ile
130                 135                 140

Asp Leu Leu Ser Thr Ser Met Glu Ala Val Asn Lys Lys Ala Arg Val
145                 150                 155                 160

Val Lys Asp Glu Ala Arg Phe Leu Leu Ile Ala Ile Gln Met Thr Ala
                165                 170                 175

Glu Ala Ala Arg Phe Arg Tyr Ile Gln Asn Leu Val Ile Lys Asn Phe
            180                 185                 190

Pro Asn Lys Phe Asn Ser Glu Asn Lys Val Ile Gln Phe Glu Val Asn
        195                 200                 205

Trp Lys Lys Ile Ser Thr Ala Ile Tyr Gly Asp Ala Lys Asn Gly Val
    210                 215                 220

Phe Asn Lys Asp Tyr Asp Phe Gly Phe Gly Lys Val Arg Gln Val Lys
225                 230                 235                 240

Asp Leu Gln Met Gly Leu Leu Met Tyr Leu Gly Lys Pro Lys
                245                 250

<210> SEQ ID NO 25
<211> LENGTH: 765
<212> TYPE: DNA
<213> ORGANISM: Unknown
<220> FEATURE:
<223> OTHER INFORMATION: Saporin S6 gene

<400> SEQUENCE: 25
atggtaacat caattaccct cgaccttgtc aaccctaccg ctggacaata ctcatccttc      60
gtagataaaa taaggaacaa tgtcaaagac cctaatctca agtacggtgg tacagatatc     120
gctgtcatcg gccctccctc aaaagaaaaa ttcctcagga taaactttca atcttccagg     180
ggaacggtct cacttggact taagagggat aatctgtatg tggtggctta tttggcaatg     240
gataatacta acgtgaatcg cgcatattac tttcggagtg aaataacaag tgcagagagc     300
accgcattgt tccccgaagc gacaactgcg aaccagaaag ccttggaata cacagaggac     360
tatcagtcca tcgaaaagaa cgcgcagata actcaaggag accagagtag aaagaactc      420 ggcctcggca tcgatctctt gagtaccagc atggaggccg tgaacaaaaa ggctagggta     480
gttaaagatg aagccaggtt cctcctgata gctatacaga tgaccgctga ggccgccagg     540
tttaggtata tccaaaacct tgtgatcaag aatttcccca acaaattcaa cagcgagaat     600
aaggtgatac agtttgaggt aaactggaaa aaaatcagca ccgctattta tggggacgcg     660
aaaaacggag tattcaataa agactacgat ttcggcttcg ggaaagttcg ccaagttaaa     720
gacttgcaaa tgggactgtt gatgtatctc ggcaaaccga gtga                      765

<210> SEQ ID NO 26
<211> LENGTH: 217
<212> TYPE: PRT
<213> ORGANISM: Unknown
<220> FEATURE:

<223> OTHER INFORMATION: Nitroreductase nfnB protein

<400> SEQUENCE: 26

```
Met Asp Ile Ile Ser Val Ala Leu Lys Arg His Ser Thr Lys Ala Phe
1               5                   10                  15
Asp Ala Ser Lys Lys Leu Thr Pro Glu Gln Ala Glu Gln Ile Lys Thr
            20                  25                  30
Leu Leu Gln Tyr Ser Pro Ser Ser Thr Asn Ser Gln Pro Trp His Phe
        35                  40                  45
Ile Val Ala Ser Thr Glu Glu Gly Lys Ala Arg Val Ala Lys Ser Ala
    50                  55                  60
Ala Gly Asn Tyr Val Phe Asn Glu Arg Lys Met Leu Asp Ala Ser His
65                  70                  75                  80
Val Val Val Phe Cys Ala Lys Thr Ala Met Asp Asp Val Trp Leu Lys
                85                  90                  95
Leu Val Val Asp Gln Glu Asp Ala Asp Gly Arg Phe Ala Thr Pro Glu
            100                 105                 110
Ala Lys Ala Ala Asn Asp Lys Gly Arg Lys Phe Phe Ala Asp Met His
        115                 120                 125
Arg Lys Asp Leu His Asp Asp Ala Glu Trp Met Ala Lys Gln Val Tyr
    130                 135                 140
Leu Asn Val Gly Asn Phe Leu Leu Gly Val Ala Ala Leu Gly Leu Asp
145                 150                 155                 160
Ala Val Pro Ile Glu Gly Phe Asp Ala Ala Ile Leu Asp Ala Glu Phe
                165                 170                 175
Gly Leu Lys Glu Lys Gly Tyr Thr Ser Leu Val Val Pro Val Gly
            180                 185                 190
His His Ser Val Glu Asp Phe Asn Ala Thr Leu Pro Lys Ser Arg Leu
        195                 200                 205
Pro Gln Asn Ile Thr Leu Thr Glu Val
    210                 215
```

<210> SEQ ID NO 27
<211> LENGTH: 654
<212> TYPE: DNA
<213> ORGANISM: Unknown
<220> FEATURE:
<223> OTHER INFORMATION: Nitroreductase nfnB gene

<400> SEQUENCE: 27

```
atggacataa ttccgtcgc tctcaagcga cattcaacaa aggcgtttga cgcttcaaaa      60
aagttgacac ctgaacaggc ggaacagatc aagacgttgc tccagtattc cccgtcttct    120
actaacagcc agccctggca ctttatcgtg gcttccacag aggagggcaa agctcgagta    180
gctaaaagcg cggcaggcaa ctatgtattc aatgagcgaa agatgcttga tgcgtcccat    240
gtcgtggtat tttgtgcgaa gacagctatg gacgatgtgt ggcttaagct ggtggtagat    300
caagaggatg ccgacggcag gttcgccacc ccagaagcca aggctgctaa tgacaagggt    360
cgcaaatttt ttgcggatat gcacaggaaa gatctccacg acgatgccga atggatggca    420
aaacaggtct acctcaacgt aggtaacttt ttgcttggtg tggctgcttt gggtctggat    480
gcggtgccga tcgagggctt tgatgcggct atacttgatg ctgagttcgg cttgaaggaa    540
aaaggatata cttcccttgt cgtagtgccc gttgggcatc atagtgtcga ggactttaac    600
gctaccctgc cgaaatctag gctcccgcaa aacataacac tcacggaggt ctga          654
```

```
<210> SEQ ID NO 28
<211> LENGTH: 465
<212> TYPE: PRT
<213> ORGANISM: Artificial Sequence
<220> FEATURE:
<223> OTHER INFORMATION: C. botulinum neurotoxin of type A linked to the
      signal peptide of syntaxin 1a

<400> SEQUENCE: 28

Met His His His His His Gln Phe Val Asn Lys Gln Phe Asn Tyr
1               5                   10                  15

Lys Asp Pro Val Asn Gly Val Asp Ile Ala Tyr Ile Lys Ile Pro Asn
            20                  25                  30

Val Gly Gln Met Gln Pro Val Lys Ala Phe Lys Ile His Asn Lys Ile
        35                  40                  45

Trp Val Ile Pro Glu Arg Asp Thr Phe Thr Asn Pro Glu Glu Gly Asp
    50                  55                  60

Leu Asn Pro Pro Glu Ala Lys Gln Val Pro Val Ser Tyr Tyr Asp
65              70                  75                  80

Ser Thr Tyr Leu Ser Thr Asp Asn Glu Lys Asp Asn Tyr Leu Lys Gly
                85                  90                  95

Val Thr Lys Leu Phe Glu Arg Ile Tyr Ser Thr Asp Leu Gly Arg Met
            100                 105                 110

Leu Leu Thr Ser Ile Val Arg Gly Ile Pro Phe Trp Gly Gly Ser Thr
        115                 120                 125

Ile Asp Thr Glu Leu Lys Val Ile Asp Thr Asn Cys Ile Asn Val Ile
    130                 135                 140

Gln Pro Asp Gly Ser Tyr Arg Ser Glu Glu Leu Asn Leu Val Ile Ile
145             150                 155                 160

Gly Pro Ser Ala Asp Ile Ile Gln Phe Glu Cys Lys Ser Phe Gly His
                165                 170                 175

Glu Val Leu Asn Leu Thr Arg Asn Gly Tyr Gly Ser Thr Gln Tyr Ile
            180                 185                 190

Arg Phe Ser Pro Asp Phe Thr Phe Gly Phe Glu Glu Ser Leu Glu Val
        195                 200                 205

Asp Thr Asn Pro Leu Leu Gly Ala Gly Lys Phe Ala Thr Asp Pro Ala
    210                 215                 220

Val Thr Leu Ala His Glu Leu Ile His Ala Gly His Arg Leu Tyr Gly
225             230                 235                 240

Ile Ala Ile Asn Pro Asn Arg Val Phe Lys Val Asn Thr Asn Ala Tyr
                245                 250                 255

Tyr Glu Met Ser Gly Leu Glu Val Ser Phe Glu Glu Leu Arg Thr Phe
            260                 265                 270

Gly Gly His Asp Ala Lys Phe Ile Asp Ser Leu Gln Glu Asn Glu Phe
        275                 280                 285

Arg Leu Tyr Tyr Tyr Asn Lys Phe Lys Asp Ile Ala Ser Thr Leu Asn
    290                 295                 300

Lys Ala Lys Ser Ile Val Gly Thr Thr Ala Ser Leu Gln Tyr Met Lys
305             310                 315                 320

Asn Val Phe Lys Glu Lys Tyr Leu Leu Ser Glu Asp Thr Ser Gly Lys
                325                 330                 335

Phe Ser Val Asp Lys Leu Lys Phe Asp Lys Leu Tyr Lys Met Leu Thr
            340                 345                 350

Glu Ile Tyr Thr Glu Asp Asn Phe Val Lys Phe Phe Lys Val Leu Asn
        355                 360                 365
```

```
Arg Lys Thr Tyr Leu Asn Phe Asp Lys Ala Val Phe Lys Ile Asn Ile
    370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
                405                 410                 415

Met Asn Phe Thr Lys Leu Lys Asn Phe Thr Gly Leu Phe Glu Phe Tyr
            420                 425                 430

Lys Leu Leu Cys Val Arg Gly Ile Ile Thr Ser Ile Met Ile Ile Ile
                435                 440                 445

Cys Cys Val Ile Leu Gly Ile Val Ile Ala Ser Thr Val Gly Gly Ile
    450                 455                 460

Phe
465

<210> SEQ ID NO 29
<211> LENGTH: 1401
<212> TYPE: DNA
<213> ORGANISM: Artificial Sequence
<220> FEATURE:
<223> OTHER INFORMATION: C. botulinum neurotoxin of type A linked to the
      signal peptide of syntaxin 1a

<400> SEQUENCE: 29
atgcaccacc accaccacca ccagttcgtg aataaacaat tcaattataa agacccagtg      60
aatggtgttg acatagcata catcaaaatc ccgaacgtgg acagatgca accggtgaaa     120 gccttcaaga ttcataacaa gatctgggtt attcctgaac gggacactt taccaaccct     180 gaagaaggtg acctgaaccc tcctccagag gctaagcagg ttcctgtttc ctactacgat     240
tcaacttatc tgagcactga taacgaaaag gataattacc ttaagggagt taccaaactg     300
ttcgagcgca tttatagcac agacctcggc agaatgctgc tgaccagcat agtgcgggga     360
attccatttt ggggggggcag cacaatcgac acggagttga aggtcatcga tacgaattgc     420
atcaacgtga taaccagat ggctcttac agatccgagg aactgaacct ggtgatcatc     480
ggcccctctg ctgatataat ccaattcgaa tgcaaaagct cggtcacga ggtgctgaat     540 cttacccgga acggatacgg tccacccag tacatacgct tagtcccga ctttacattc     600 ggcttcgagg aaagtcttga agtggacacg aatccactgc tgggagctgg caagttcgcc     660
actgatcctg ccgttacact tgctcatgaa ctgattcatg ctggacaccg gctttatggg     720
atagctataa atccgaatag agtctttaag gttaacacaa atgcctacta cgaaatgtct     780
ggccttgagg tttcattcga ggagcttagg accttggag gccacgacgc taaattcatc     840
gactctctgc aggagaatga gtttcggctg tactactaca caagtttaa ggacattgcc     900 agtactctga caaggctaa gagcatcgtc gggaccacag ccagcctcca atatatgaaa     960
aacgtgttca ggaaaagta ccttctgtca gaagacacat caggaaaatt ctcagtcgac    1020
aaactgaaat ttgacaagct gtacaagatg ctgactgaaa tatacacaga ggacaacttc    1080
gtgaagtttt taaagtcct gaacagaaag acttacttga acttcgacaa agccgtcttt    1140
aaaatcaata tcgtcccaaa ggttaattac actatctatg acggattcaa tctcagaaac    1200
acgaacttgg ctgccaactt caatggacag aacacagaga tcaacaacat gaatttact    1260 aagcttaaaa atttcacagg cctgttcgag ttctataagc ttctttgcgt ccgaggcatc    1320
attacatcca tcatgatcat aatctgctgt gtgatattgg catagtgat tgcatccacc    1380 gtgggggca ttttttgccta g                                              1401
```

-continued

```
<210> SEQ ID NO 30
<211> LENGTH: 469
<212> TYPE: PRT
<213> ORGANISM: Artificial Sequence
<220> FEATURE:
<223> OTHER INFORMATION: C. botulinum neurotoxin of type B linked to the
      signal peptide of syntaxin 1a

<400> SEQUENCE: 30
```

```
Met His His His His His Pro Val Thr Ile Asn Asn Phe Asn Tyr
1               5                   10                  15

Asn Asp Pro Ile Asp Asn Asn Asn Ile Ile Met Met Glu Pro Pro Phe
            20                  25                  30

Ala Arg Gly Thr Gly Arg Tyr Tyr Lys Ala Phe Lys Ile Thr Asp Arg
        35                  40                  45

Ile Trp Ile Ile Pro Glu Arg Tyr Thr Phe Gly Tyr Lys Pro Glu Asp
    50                  55                  60

Phe Asn Lys Ser Ser Gly Ile Phe Asn Arg Asp Val Cys Glu Tyr Tyr
65                  70                  75                  80

Asp Pro Asp Tyr Leu Asn Thr Asn Asp Lys Lys Asn Ile Phe Leu Gln
                85                  90                  95

Thr Met Ile Lys Leu Phe Asn Arg Ile Lys Ser Lys Pro Leu Gly Glu
            100                 105                 110

Lys Leu Leu Glu Met Ile Ile Asn Gly Ile Pro Tyr Leu Gly Asp Arg
        115                 120                 125

Arg Val Pro Leu Glu Glu Phe Asn Thr Asn Ile Ala Ser Val Thr Val
    130                 135                 140

Asn Lys Leu Ile Ser Asn Pro Gly Glu Val Glu Arg Lys Lys Gly Ile
145                 150                 155                 160

Phe Ala Asn Leu Ile Ile Phe Gly Pro Gly Pro Val Leu Asn Glu Asn
                165                 170                 175

Glu Thr Ile Asp Ile Gly Ile Gln Asn His Phe Ala Ser Arg Glu Gly
            180                 185                 190

Phe Gly Gly Ile Met Gln Met Lys Phe Cys Pro Glu Tyr Val Ser Val
        195                 200                 205

Phe Asn Asn Val Gln Glu Asn Lys Gly Ala Ser Ile Phe Asn Arg Arg
    210                 215                 220

Gly Tyr Phe Ser Asp Pro Ala Leu Ile Leu Met His Glu Leu Ile His
225                 230                 235                 240

Val Leu His Gly Leu Tyr Gly Ile Lys Val Asp Asp Leu Pro Ile Val
                245                 250                 255

Pro Asn Glu Lys Lys Phe Phe Met Gln Ser Thr Asp Ala Ile Gln Ala
            260                 265                 270

Glu Glu Leu Tyr Thr Phe Gly Gly Gln Asp Pro Ser Ile Ile Thr Pro
        275                 280                 285

Ser Thr Asp Lys Ser Ile Tyr Asp Lys Val Leu Gln Asn Phe Arg Gly
    290                 295                 300

Ile Val Asp Arg Leu Asn Lys Val Leu Val Cys Ile Ser Asp Pro Asn
305                 310                 315                 320

Ile Asn Ile Asn Ile Tyr Lys Asn Lys Phe Lys Asp Lys Tyr Lys Phe
                325                 330                 335

Val Glu Asp Ser Glu Gly Lys Tyr Ser Ile Asp Val Glu Ser Phe Asp
            340                 345                 350

Lys Leu Tyr Lys Ser Leu Met Phe Gly Phe Thr Glu Thr Asn Ile Ala
```

```
                355                 360                 365
Glu Asn Tyr Lys Ile Lys Thr Arg Ala Ser Tyr Phe Ser Asp Ser Leu
    370                 375                 380

Pro Pro Val Lys Ile Lys Asn Leu Leu Asp Asn Glu Ile Tyr Thr Ile
385                 390                 395                 400

Glu Glu Gly Phe Asn Ile Ser Asp Lys Asp Met Glu Lys Glu Tyr Arg
                405                 410                 415

Gly Gln Asn Lys Ala Ile Asn Lys Gln Ala Tyr Glu Glu Ile Ser Lys
            420                 425                 430

Glu His Leu Ala Val Tyr Lys Ile Gln Met Cys Lys Ser Val Ile Met
        435                 440                 445

Ile Ile Ile Cys Cys Val Ile Leu Gly Ile Val Ile Ala Ser Thr Val
    450                 455                 460

Gly Gly Ile Phe Ala
465

<210> SEQ ID NO 31
<211> LENGTH: 1410
<212> TYPE: DNA
<213> ORGANISM: Artificial Sequence
<220> FEATURE:
<223> OTHER INFORMATION: C. botulinum neurotoxin type B linked to the
      signal peptide of syntaxin 1a

<400> SEQUENCE: 31
atgcaccacc accatcatca tcccgtgacc atcaacaatt tcaactataa tgaccctatc      60
gataacaaca acatcattat gatggagccc ccttctcgccc gcggcaccgg gagatactac    120
aaggccttca aaataaccga taggatctgg atcatcccag agaggtacac cttcgggtac    180
aagcctgagg actttaataa atcaagcggt atctttaata gggatgtgtg tgaatactac    240
gaccctgact atctcaatac caacgacaaa agaatatct tccttcagac tatgatcaag    300
cttttcaatc gaattaagag taagccgctt ggtgagaaac tgctggagat gatcataaac    360
ggcatcccct acctcggaga tcgccgcgtt ccgctggaag agtttaacac taatatcgca    420
agcgtcactg taaataaact catcagcaac cggggggaag tggaaaggaa gaagggaatc    480
tttgctaacc tgattatctt tggaccaggc ccagtgttga atgaaaacga gaccatcgac    540
atcgggatcc agaaccactt tgcatcacga gaggggtttg ggggggattat gcagatgaag    600 ttctgccccg agtacgtgtc agtgttcaat aacgtgcagg aaaacaaagg agcatccatc    660
ttcaatcgcc gaggctactt ctctgatcct gctctcatcc tcatgcacga gctcattcac    720
gtgctgcacg gactttatgg catcaaggtg gacgacctgc ctattgtgcc gaatgaaaag    780
aagttcttca tgcagagtac tgatgccatc caggctgagg aactgtacac tttcggggggc    840 caggacccat ccattatcac cccaagtact gataagtcaa tctatgacaa agttctgcag    900
aacttccgcg aatcgtggga taggctcaac aaagtgctgg tgtgtattag cgaccccaac    960
attaacatca atatttacaa gaacaaattc aaggacaaat ataaattcgt ggaggactct   1020
gagggcaagt attcaattga cgtggagagc ttcgacaaac tgtacaaaag cctgatgttc   1080
ggtttcacag agaccaacat agcagagaac tataagatta aaactcgcgc gagctacttt   1140
tcagattcac tgcctccggt gaaaatcaag aacctcctgg ataatgagat ctataccata   1200
gaagaaggat ttaacatttc gacaaggac atggaaaagg agtaccgggg acagaacaag   1260
gccatcaaca acaggcctta tgaagaaatc agcaaggagc cctcgccgt ctacaaaatt   1320 caaatgtgca aaagcgtcat aatgattatt atctgctgcg taatcctggg gatagtgatc   1380
```
gcttccaccg taggcggcat cttcgcctga              1410

<210> SEQ ID NO 32
<211> LENGTH: 476
<212> TYPE: PRT
<213> ORGANISM: Artificial Sequence
<220> FEATURE:
<223> OTHER INFORMATION: C. botulinum neurotoxin of serotype C linked to
      the signal peptide of VAMP2

<400> SEQUENCE: 32

Met His His His His His Pro Ile Thr Ile Asn Asn Phe Asn Tyr
1               5                   10                  15

Ser Asp Pro Val Asp Asn Lys Asn Ile Leu Tyr Leu Asp Thr His Leu
                20                  25                  30

Asn Thr Leu Ala Asn Glu Pro Glu Lys Ala Phe Arg Ile Thr Gly Asn
            35                  40                  45

Ile Trp Val Ile Pro Asp Arg Phe Ser Arg Asn Ser Asn Pro Asn Leu
        50                  55                  60

Asn Lys Pro Pro Arg Val Thr Ser Pro Lys Ser Gly Tyr Tyr Asp Pro
65                  70                  75                  80

Asn Tyr Leu Ser Thr Asp Ser Asp Lys Asp Pro Phe Leu Lys Glu Ile
                85                  90                  95

Ile Lys Leu Phe Lys Arg Ile Asn Ser Arg Glu Ile Gly Glu Glu Leu
            100                 105                 110

Ile Tyr Arg Leu Ser Thr Asp Ile Pro Phe Pro Gly Asn Asn Asn Thr
        115                 120                 125

Pro Ile Asn Thr Phe Asp Phe Asp Val Asp Phe Asn Ser Val Asp Val
130                 135                 140

Lys Thr Arg Gln Gly Asn Asn Trp Val Lys Thr Gly Ser Ile Asn Pro
145                 150                 155                 160

Ser Val Ile Ile Thr Gly Pro Arg Glu Asn Ile Ile Asp Pro Glu Thr
                165                 170                 175

Ser Thr Phe Lys Leu Thr Asn Asn Thr Phe Ala Ala Gln Glu Gly Phe
            180                 185                 190

Gly Ala Leu Ser Ile Ile Ser Ile Ser Pro Arg Phe Met Leu Thr Tyr
        195                 200                 205

Ser Asn Ala Thr Asn Asp Val Gly Glu Gly Arg Phe Ser Lys Ser Glu
210                 215                 220

Phe Cys Met Asp Pro Ile Leu Ile Leu Met His Glu Leu Asn His Ala
225                 230                 235                 240

Met His Asn Leu Tyr Gly Ile Ala Ile Pro Asn Asp Gln Thr Ile Ser
                245                 250                 255

Ser Val Thr Ser Asn Ile Phe Tyr Ser Gln Tyr Asn Val Lys Leu Glu
            260                 265                 270

Tyr Ala Glu Ile Tyr Ala Phe Gly Gly Pro Thr Ile Asp Leu Ile Pro
        275                 280                 285

Lys Ser Ala Arg Lys Tyr Phe Glu Glu Lys Ala Leu Asp Tyr Tyr Arg
290                 295                 300

Ser Ile Ala Lys Arg Leu Asn Ser Ile Thr Thr Ala Asn Pro Ser Ser
305                 310                 315                 320

Phe Asn Lys Tyr Ile Gly Glu Tyr Lys Gln Lys Leu Ile Arg Lys Tyr
                325                 330                 335

Arg Phe Val Val Glu Ser Ser Gly Glu Val Thr Val Asn Arg Asn Lys
            340                 345                 350

```
Phe Val Glu Leu Tyr Asn Glu Leu Thr Gln Ile Phe Thr Glu Phe Asn
        355                 360                 365

Tyr Ala Lys Ile Tyr Asn Val Gln Asn Arg Lys Ile Tyr Leu Ser Asn
        370                 375                 380

Val Tyr Thr Pro Val Thr Ala Asn Ile Leu Asp Asp Asn Val Tyr Asp
385                 390                 395                 400

Ile Gln Asn Gly Phe Asn Ile Pro Lys Ser Asn Leu Asn Val Leu Phe
                405                 410                 415

Met Gly Gln Asn Leu Ser Arg Asn Pro Ala Leu Arg Lys Val Asn Pro
                420                 425                 430

Glu Asn Met Leu Tyr Leu Phe Thr Lys Phe Cys His Lys Ala Ile Asp
            435                 440                 445

Gly Arg Ser Leu Tyr Asn Met Met Ile Ile Leu Gly Val Ile Cys Ala
        450                 455                 460

Ile Ile Leu Ile Ile Ile Ile Val Tyr Phe Ser Thr
465                 470                 475

<210> SEQ ID NO 33
<211> LENGTH: 1431
<212> TYPE: DNA
<213> ORGANISM: Artificial Sequence
<220> FEATURE:
<223> OTHER INFORMATION: C. botulinum neurotoxin of serotype C linked to
      the signal peptide of VAMP2

<400> SEQUENCE: 33
atgcaccacc atcatcatca tcctattaca atcaacaatt ttaattattc tgacccagtg      60
gacaacaaaa acatactttta ccttgatacc cacctcaata ctctggcgaa cgagccagag    120
aaagcgttcc gcataacagg aaacatatgg gtgattcctg acagattcag tcgaaatagt    180
aacccaaacc tgaacaagcc tccgagggtt acatcccta agtccggtta ttacgacccc    240
aattacctgt ctacagatag cgataaagat ccttttcctga agagatcat taaactgttc    300 aaacgaataa actcccgcga atcggggag gaactcattt atcgattgtc cacggacatc    360 ccttccctg gtaataacaa caccccgatt aataccttg acttcgacgt cgactttaac      420
tctgtggatg tgaagactcg gcagggtaac aactgggtta aaactgggtc aatcaaccg    480 tctgtcataa ttacaggccc tagggagaat ataattgatc cggagaccag caccttaaa    540 ttgactaata atactttcgc cgcacaggag gggttcggcg ccctgtctat catatcaatc    600
agtccccgat ttatgctgac ctactctaat gcaactaacg acgtcgggga aggtcggttt    660
agcaaaagtg agttctgcat ggacccgatc ctcatactga tgcacgagtt gaaccatgca    720
atgcataatc tgtatggaat cgctattccc aacgatcaga caatatcttc cgtcacgtca    780
aacattttct attctcagta taatgtgaaa ctggaatatg ctgagatcta cgcctttggt    840
ggccccacaa ttgacctgat tccaaagagc gccaggaagt acttcgagga aaaggcactt    900
gattattata ggagcatcgc aaagcgcctg aacagcatca aacggccaa cccaagctct    960 ttcaacaaat atataggcga atacaagcaa aaactcatta gaaatacag gtttgtggtg   1020 gaaagcagcg gagaggtaac cgtaaaccgc aacaaattcg tggagctgta caacgaactg   1080
actcagatct ttacggaatt caattacgct aagatctaca atgtgcagaa ccggaagatt   1140
tacctgtcca tgtttacac acctgtcact gctaatattc tcgatgacaa tgtgtacgac   1200
attcagaatg gcttcaacat ccccaagtct aacctgaacg tgctgttcat gggcagaac   1260 cttagccgca atcctgcgct cgcaaagtc aaccctgaga atatgctgta tcttcttcacg   1320
```

```
aagttctgtc acaaggccat agacggtaga agtctttata atatgatgat tatactgggg      1380
gtgatctgcg cgattatcct tattattatc attgtatact tctctacatg a               1431
```

VIRAL VECTORS FOR TREATING NEUROGENIC DETRUSOR OVERACTIVITY

REFERENCE TO SEQUENCE LISTING SUBMITTED VIA EFS-WEB

This application includes an electronically submitted sequence listing in .txt format. The .txt file contains a sequence listing entitled "Sep. 18, 2019 3493-0679PUS1 ST25.txt" created on Sep. 13, 2019 and is 82,155 bytes in size. The sequence listing contained in this .txt file is part of the specification and is hereby incorporated by reference herein in its entirety.

The present invention is directed to a viral expression vector and a pharmaceutical composition thereof that selectively modulates or silences the afferent nerves of the bladder, as a gene therapy strategy for the treatment of neurogenic detrusor overactivity (NDO).

In particular, the present invention is related to the field of control of urine storage and bladder emptying or micturition, which is dependent upon the activity of two functional units in the lower urinary tract: (1) a reservoir (the urinary bladder) and (2) an outlet consisting of the bladder neck, urethra, and striated muscles of the external urethral sphincter (EUS) (Fowler et al. 2008; Morrison et al. 2005). These structures are controlled by three sets of efferent peripheral nerves: sacral parasympathetic (pelvic nerves), thoracolumbar sympathetic (hypogastric nerves and lumbo-sacral sympathetic chain), and somatic nerves (pudendal nerves) distributed bilaterally (de Groat 1986; Morrison et al. 2005). These nerves consist of efferent axons originating at thoracolumbar and sacral spinal levels. Parasympathetic efferent nerves contract the bladder and relax the urethra. Sympathetic efferent nerves relax the bladder and contract the urethra. Somatic efferent nerves contract the EUS. These nerves also contain afferent neurons that transmit information from the lower urinary tract to the lumbosacral spinal cord. The cellular bodies of the afferent neurons of the human lower urinary tract are located in the S2-S4 and T11-L2 dorsal root ganglia (DRG). Sensations of bladder fullness are conveyed to the spinal cord by the pelvic and hypogastric nerves, whereas sensory input from the bladder neck and the urethra is carried in the pudendal and hypogastric nerves.

A similar segmental organization occurs in nonhuman primates, cats and dogs. In rats, cellular bodies of the afferent neurons of pelvic, pudendal and hypogastric nerves are located in the L6-S1 and T11-L2 DRG respectively. The neural pathways that control lower urinary tract function are organized as simple on-off switching circuits that maintain a reciprocal relationship between the urinary bladder and the urethral outlet. Storage reflexes are activated during bladder filling and are organized primarily in the spinal cord, whereas voiding is mediated by reflex mechanisms that are organized in the brain (Fowler et al. 2008). Throughout bladder filling, the parasympathetic innervation of the detrusor is inhibited and the smooth and striated parts of the urethral sphincter are activated, preventing involuntary bladder emptying. This process is organized by urethral reflexes known collectively as the 'guarding reflex'. They are activated by bladder afferent activity that is conveyed through the pelvic nerves, and are organized by interneuronal circuitry in the spinal cord (Fowler et al. 2008).

NDO refers to a condition in which abnormal bladder function is observed in patients with neurological diseases, such as cerebrovascular disease or cerebral infarction, brain or spinal cord injury due to trauma, multiple sclerosis, Parkinson's disease, congenital malformation e.g. spina bifida, or disease e.g. hereditary spastic paraplegia of the central nervous system, peripheral neuropathy, and various spinal lesions, that is, spinal cord compression and injury due to vertebra(e) fracture, cervical and lumbar spondylosis, spondylosis deformans, spondylolisthesis, spinal stenosis, vertebral disk hernia and the like.

NDO is characterized by involuntary detrusor (bladder) contractions during the filling phase, which may be spontaneous or provoked due to a relevant neurological condition. It is often associated to bladder-sphincter dyssynergia.

NDO due to spinal cord injury (SCI) is the most severe form of NDO. Immediately after SCI there is a period of spinal shock lasting for 2-12 weeks during which the bladder is areflexic, accountable for complete urinary retention. Then, a spinal micturition reflex progressively develops that is responsible for NDO. For SCI patients, these impairments lead to urinary incontinence and increase in bladder pressure, which, if untreated, can damage upper urinary tract and precipitate renal failure. Urinary incontinence is associated with a significant burden and severely impairs quality of life. In SCI patients, recurrent urinary tract infections due to incomplete bladder emptying and renal failure remain the first cause of rehospitalization and second cause of mortality respectively. SCI disrupts voluntary control of voiding as well as the normal reflex pathways that coordinate bladder and sphincter functions. In suprasacral spinal lesion, NDO results of the unmasking of a segmental reflex at the level of the sacral cord, mediated by bladder afferent nociceptive C-fibers (de Groat and Yoshimura, 2006). These silent C-fibers become mechano-sensitive and initiate automatic micturition reflex after SCI. This reflex is facilitated after elimination of supraspinal control. Plasticity occurs in bladder afferents and is associated with changes in the properties of ion channels and electrical excitability of afferent neurons, and appears to be mediated in part by neurotrophic factors released in the spinal cord and the peripheral target organs. Overall, the neurobiological substrate for NDO comprises functional alterations in bladder urothelium and sub-urothelium as well as increased afferent sensory messages to the spinal cord, originating in the bladder. Exacerbated afferent bladder stimuli, resulting from hypertrophy and hyperactivity of non-myelinated type-C bladder afferent neurons, are the main mechanisms causing NDO in SCI subjects.

Standard of care for the treatment of NDO consists in inhibiting efferent neurotransmission at the detrusor level. Accordingly, NDO patients are currently treated with anti-muscarinics, which block the activity of the muscarinic acetylcholine receptors thereby inhibiting detrusor contractions, and/or repeated intradetrusor injection of *Clostridium botulinum* neurotoxin A (BoNT-A), again to block detrusor contractions by acting on bladder efferents. Both treatments must be combined with intermittent bladder catheterization (5-6 times/day).

BoNT-A injections suppress the formation of SNARE complex, blocking the fusion of neurotransmitter-filled vesicles with the plasma membrane of efferent neurons and their release during exocytosis. Accordingly, injection of BoNT-A is used as medication for treating patients with overactive bladder from neurogenic origin or not. For example, PCT patent applications WO 99/03483 and WO 2010/022979 disclose the use of BoNT-A injection to prevent a nerve from stimulating its target tissue, e.g. a muscle, a gland, or another nerve, for the treatment of various urinary disorders.

WO2013/180799 discloses the use of a viral vector encoding a modified botulinum neurotoxin, thereby producing a protein that has improved binding properties to its human receptors. Following production in cell lines, once recovered and purified from the supernatants, this neurotoxin can be locally applied to treat a condition associated with unwanted neuronal activity such as NDO. However, these vectors are not conceived for a gene therapy approach.

Nevertheless, injection of botulinum neurotoxins presents the inconvenient of toxin diffusion, which is largely due to diffusion of toxins to other regions of the body. The adverse effects range from transient non-serious events such as ptosis and diplopia to life-threatening events even death. In addition, for NDO these injections must be repeated in average every 6 months because of decreased efficacy overtime.

Because NDO, with or without bladder-sphincter dyssynergia, caused by supra sacral spinal lesions is due to the emergence of an abnormal reflex mediated by bladder afferences (aδ and c fibers), an alternative approach for the treatment of NDO has been developed by Brindley (Brindley et al 1986). This approach combines posterior sacral rhizotomies and sacral anterior roots stimulation (SARS). This treatment appeared to be one of the most effective therapeutic methods for NDO caused by complete suprasacral spinal lesions: sacral rhizotomies permanently increases the compliance of the bladder and eliminates hyperactivity of the detrusor—and detrusor-sphincteric dyssynergia—which are the main causes of renal failure and urinary incontinence, while implantation of a stimulator of the anterior spinal roots enables the patient to elicit and to control micturition.

Deafferentation by posterior sacral rhizotomies, as proposed by Brindley (1986), consists of the complete surgical transsection of all afferent neural fibers to the spinal S2-S4 segments, including those providing sensory input from the detrusor muscle. In this way, the sensory stimuli from the detrusor muscle cannot reach anymore the central nervous system, and consequently, reflex activities generated by the central nervous system causing uncontrolled bladder contractions can be inhibited. The procedure is necessary to prevent exacerbated reflex activities of detrusor and allows larger amount of urine to be stored at low bladder pressure. However, bladder deafferentation obtained from extensive, non-selective, irreversible pelvi-perineal deafferentation by posterior sacral rhizotomies (S2-S4) has many pitfalls and drawbacks, as it is responsible for loss of remaining pelviperineal sensation if present, impairing orgasm if present, reflex erection and ejaculation if present, and reflex micturition and defecation if present, and possibly facilitating bedsore because of loss of skin sensory innervation. In addition, the magnitude of neurosurgical procedure makes it expensive and can be responsible for cerebrospinal fluid fistulas and in the long-term for Charcot spinal arthropathy.

Consequently, there is a need for a new strategy to treat NDO in case of supraspinal lesion, targeting specifically its pathophysiology i.e. the abnormal spinal reflex mediated by bladder afferences, but without affecting other afferent neurons conveyed in the same nerves, while sparing the bladder efferent neurons. The strategy we propose is a gene therapy approach resulting in selective molecular bladder deafferentation, to restore continence and micturition in NDO patients when combined with sacral anterior roots stimulation. This has been achieved by a new strategy requiring a viral expression vector able to deliver therapeutic transgene(s) presenting:

capacity to inhibit/silence neurotransmission or synaptic transmission of afferent neurons;
high selectivity, notably for the afferent neurons of the bladder;
high efficiency;
stability of expression over time; and
absence of off-target denervation.

In the context of the present invention, the inventors surprisingly found that, following injection of the viral expression vector in the bladder wall, it is possible to obtain selective and stable transgenes expression in the afferent neurons of the bladder, using a viral expression vector that stably expresses over time proteins and/or transcripts to treat NDO, by specifically inhibiting/silencing neurotransmission or synaptic transmission of bladder afferent neurons at the spinal cord level.

The present invention provides a method and a pharmaceutical composition for the treatment of the NDO comprising the viral expression vector carrying a transcription cassette that harbors transgene(s) inhibiting/silencing neurotransmission or synaptic transmission of afferent neurons. Preferably, the method and a pharmaceutical composition according to the invention comprise a viral expression vector carrying a transcription cassette that harbors transgene(s) disrupting SNARE complex, and/or ribosomal complex, and/or activating GABA(A) receptors, and/or inducing conditionally targeted neuron ablation, when transcribed, that inhibit/silence neurotransmission or synaptic transmission of bladder afferent neurons.

The term "transcription cassette" as used herein refers to any nucleic acid sequence containing a promoter and a downstream coding sequence or transgene, which expression is driven by said promoter, which is followed by a polyadenylation signal. The term "transgene" refers to a particular nucleic acid sequence encoding for a RNA and/or a polypeptide or a portion of a polypeptide to be expressed in a cell into which the nucleic acid sequence is introduced. The term "transgene" includes (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By "mutant form" is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell, or the transgene may include both a leader peptide or signal sequence plus a membrane anchor peptide or even be a fusion protein between two naturally occurring proteins or part of them, such that the transgene will remain anchored to cell membranes.

As used herein, the term "ribosomal complex" refers to a complex which is essentially composed of the subunits of ribosomes, such as 80S and 70S subunits that catalyzes the synthesis of proteins, referred as translation.

In a first aspect, the present invention thus provides a viral expression vector comprising at least:
a) one promoter selectively active in afferent neurons of the bladder,
b) one transcription cassette comprising a nucleotide sequence operably linked to said promoter, wherein said nucleotide sequence silences or inhibits the transduction of the neurotransmitter signal in postsynaptic cell when transcribed, and
c) one sequence conferring long-term expression, such as that known as LTE (Lokensgard et al, 1997) and/or containing DNA insulators (Amelio et al, 2006) from the HSV-1 genome, operably linked to said transcription cassette.

In preferred embodiment, the nucleotide sequence of viral expression vector according to the invention silences or inhibits neurotransmission or synaptic transmission when transcribed or translated by disrupting the SNARE complex, and/or the ribosomes complex, and/or by activating GABA (A) receptors, and/or by inducing conditionally targeted neuron ablation.

In a preferred embodiment, the nucleotide sequence of viral expression vector according to the invention, when transcribed, disrupts at least one of the proteins selected from VAMP, SNAP-25 or syntaxin 1a, which are part of the SNARE complex, or codes for the protein GAD67 or for an active fragment thereof, or codes for a protein disrupting the ribosomes complex or for an active fragment thereof, or codes for a protein inducing conditionally targeted neuron ablation, or for an active fragment thereof.

In a particular embodiment, the said protein disrupting the ribosomes complex according to the invention is a wild-type or a modified ribosome inactivating protein (RIP) or an active fragment thereof, preferentially said RIP are selected from RIP of type 1 or type 2, preferentially RIP of type 1 are selected from saporin, gelonin, dianthin, trichosanthin; and RIP of type 2 are selected from ricin, volkensin and abrin, more preferentially said RIP of type 1 is saporin S6 or an active fragment thereof.

The term "protein inducing conditionally targeted neuron ablation" relates to a protein which converts innocuous prodrug substrates, such as metronidazole (MTZ), into cytotoxic DNA crosslinking agents—providing cell-specific ablation of the targeted cell type i.e. afferent neuron of the bladder. Example of such protein inducing conditionally targeted neuron ablation are nitroreductases (NTR).

The protein inducing conditionally targeted neuron ablation according to the invention is therefore selected from the group consisting of a wild-type or a modified NTR or an active fragment thereof. Preferentially, said NTR is selected from the group consisting of a wild-type or a modified oxygen-insensitive NAD(P)H nitroreductases or an active fragment thereof, more preferably said NTR is selected from the group consisting of a wild-type or a modified *E. coli* nitroreductases, even more preferentially said NTR is a wild-type or a modified *E. coli* nfnB or an active fragment thereof.

The term "viral vector" or "viral expression vector" as used herein refers to a nucleic acid vector that includes at least one element of a virus genome and may be packaged into a viral particle. In the context of the present invention, the term "viral vector" has to be understood broadly as including nucleic acid vector (e.g. DNA viral vector) as well as viral particles generated thereof. According to the present invention the viral expression vector is an adeno-associated virus (AAV) vector or a herpes simplex virus (HSV) vector, preferably a HSV-1 vector or a HSV-2 vector, even more preferably a defective viral vector derived from HSV-1. As used herein the term "defective viral vector" shall refer to viral vectors that are missing genes or parts of genes necessary to complete successfully the viral life cycle.

According to the present invention, the term "AAV" refers to the Adeno-Associated Virus itself or to derivatives thereof including recombinant AAV vector particles. Furthermore, as used herein, the term "AAV" includes many different serotypes, which have been isolated from both human and non-human primate samples. Preferred AAV serotypes are the human serotypes, more preferably human AAV of serotypes 2, 5 and 9, most preferably human AAV of serotype 5, which is the serotype displaying the highest level of neurotropism.

According to the present invention, the term "defective viral vector derived from HSV" refers both to defective recombinant HSV vectors and amplicon HSV vectors. The terms "defective recombinant HSV", as used herein, describes a helper-independent vector, the genome of which comprises at least complete deletions of the genes coding for two essential proteins, known as ICP4 and ICP27. The ICP4 gene is present in two copies, located in the inverted repeated sequences known as c and c' of the virus genome, and both copies of this gene are deleted. The gene encoding ICP27 is located in the unique long (UL) sequence of the virus genome. Preferentially, helper-independent vectors according to the invention carry the therapeutic transcription cassette(s) embedded into the LAT (Latency Associated Transcripts) locus (Berthomme et al. 2000 and Berthomme et al. 2001), which is a repeated locus that is contained in the inverted repeated sequences known as b and b' of the virus genome. More preferentially, the transcription cassette is placed either between the Latency Associated Promoter (LAP) and the Long-Term Expression (LTE) region (site 1), or between the LTE region and the DNA insulator (INS) sequence present downstream of the LTE (site 2) (as shown in FIG. 1). Defective recombinant HSV-1 vectors according to the present invention carry transcription cassette(s) expressing the different transgenes above described in order to inhibit/silence neurotransmission, i.e. expressing wild type or modified light chain botulinum toxins, and/or antisense RNA (AS-RNA) targeting SNARE proteins, and/or GAD67, and/or RIPs, and or NTRs, all of them driven by long-term DRG-specific promoters as described in the present invention. The b and b' sequences of the virus genome are also known as TRL (Terminal Repeat L) and IRL (Internal Repeat L) respectively, while the c' and c sequences are also known as IRS (Internal Repeat S) and TRS (Terminal Repeat S), where L and S refer respectively to the unique long (L) and unique short (S) sequences of the HSV-1 genome.

Moreover, helper-independent vectors according to the invention can comprise additional deletions in genes encoding non-essential proteins such as ICP34.5, UL55, UL56, and UL41 proteins. These defective HSV vectors are multiplied in cell lines expressing simultaneously the proteins ICP4 and ICP27 (Marconi et al, 2010).

WO 2006/050211 discloses the use of a defective HSV-1 vector for gene therapy of pain. However, the vectors according to the invention differ from the vector described in WO 2006/050211 in several significant respects, which are important in regard to the usefulness and efficacy of the vectors according to the invention. Most important, transgenic transcription cassettes according to the invention are introduced into the LAT locus, as this region contains both the LTE and the DNA insulator sequences (INS) that confer long-term expression to the DRG-specific promoters driving transgene expression in transcription cassettes according to the invention, whereas the vector described in WO 2006/050211 was conceived and proved for short-term action and, therefore, their transcription cassettes are driven by ubiquitous promoters and were not introduced into the LAT regions.

By "Amplicon or amplicon vector" it is meant a helper-dependent vector, the genome of which lacks most or all HSV genes coding for virus proteins. The genome of amplicon vectors is a concatemeric DNA composed of multiple copies in tandem of a plasmid—known as the amplicon plasmid—that carries one origin of DNA replication and one packaging signal from HSV-1 genome, in addition to transgenic DNA (i.e. transcription cassettes) of interest. Amplicon plasmids according to the present invention carry transcription cassettes expressing the different transgenes above described in order to inhibit/silence neurotransmission, i.e., expressing wild type or modified light chain botulinum toxins, and/or interfering RNA (RNAi) targeting SNARE proteins, and/or GAD67, and/or RIPs, and/or NTRs, all of them driven by long-term promoters, preferentially a long-term DRG-specific promoters as described in the present invention (see FIG. 2).

In a preferred embodiment, the vector according to the invention is a defective recombinant vector lacking at least the genes coding for the essential proteins ICP4 and ICP27, preferentially a vector lacking both ICP4 and ICP27. This vector can lack other genes, coding for non-essential proteins, such as ICP34.5, UL55, UL56 and/or UL41 gene proteins, and carries the DRG-specific transcription cassette(s), described in FIG. 7, embedded into the LAT regions of the vector genome.

In another embodiment, the vector according to the invention is an amplicon vector carrying the above described transcription cassettes driven by long-term DRG-specific promoters, as described in other parts of this document.

In a preferred embodiment, the transcription cassette according to the invention is introduced into the LAT locus.

The expression "Recombinant DNA" as used herein describes a nucleic acid molecule, i.e., a polynucleotide of genomic, cDNA, viral, semisynthetic, and/or synthetic origin, which, by virtue of its origin or manipulation, is not associated with all or a portion of the polynucleotide with which it is associated in nature. The term "recombinant" as used with respect to virus means a virus carrying a recombinant genome or a genome that has been manipulated to introduce mutations, deletions or one or more heterologous polynucleotides, including genes. The term "recombinant" as used with respect to a protein or polypeptide, means a polypeptide produced by expression of a recombinant nuclei acid. The term "recombinant" as used with respect to a host cell means a recombinant vector that carries recombinant DNA within the host cell or a cell that contains recombinant DNA inserted in its genome. The term "infection" refers to the ability of a viral vector to enter into a host cell or subject.

Defective vectors derived from HSV allow to infect neighbouring sensory neurons and establish latent infections in the nucleus of these neurons, located in the trigeminal or the dorsal root ganglia (DRG), depending on the site of infection. In particular, HSV-1 naturally infects sensory neurons and establishes lifelong latent infections in the nucleus of these neurons. It could thus be hypothesized that following injection in the bladder wall, the vectors, such as vector derived from HSV-1, will reach the sensory DRG innervating the bladder from where they will stably express the therapeutic transgene, provided that adequate bladder afferent neuron-specific promoters drive their expression.

However, HSV-1 can also infect and establish latent infections in autonomic neurons (Furuta et al., 1993; Warren et al. 1978), and preliminary results demonstrate that this is actually the case when the vector is inoculated into the bladder. Therefore, it is mandatory that expression from the vectors be utterly controlled by afferent-specific promoters, also called selective promoters or selective afferent neuron-specific promoters, in order to obtain significant transgene expression only in these neurons (i.e. afferent neuron), thus avoiding expression in autonomic, also called efferent, neurons. Selective molecular or biochemical (as opposite to surgical) deafferentation of bladder afferent neurons is the most critical aspect of the present invention as it is important to preserve remaining pelvi-perineal sensation if present, orgasm if present, reflex erection and ejaculation if present, and reflex micturition and defecation if present, all of which are conveyed by sensory nerves of the pelvis that do not originate in the bladder. Further, selective bladder deafferentation would also allow to preserve bladder efferent neurons, which could be later stimulated by electrical stimulation for example via electrodes. Some studies describe the use of HSV-1-based vectors in which the transcription cassettes comprise either transient (Miyazato et al., 2009) or long-term (Puskovic et al., 2004; Miyagawa et al., 2015; WO 2015/009952A1) promoters. However, the promoters used in the studies of Puscovic (LAP2), Miyazato (HCMV promoter) and Miyagawa (artificial CAG promoter) are non-selective, leading to expression of their transgenes in many cell types, including autonomic neurons, brain neurons, and non-neuronal cells. In contrast, by combining viral regulatory sequences and afferent neuron-specific cellular promoters, some of the vectors according to the present invention enable a significantly higher afferent neuron-specific expression of the transgenes of interest (see FIG. 13).

The vectors used in the practice of the invention include at least one promoter selectively active in afferent neurons that is operationally linked to nucleotides (usually DNA) encoding an RNA molecule. By "operationally linked" it is meant herein that, in the vector, the promoter is associated with the nucleotides encoding the RNA in a manner that allows the promoter to drive transcription (i.e. expression) of the RNA from the nucleotides. Transcription of RNA from, e.g. a DNA template is well-understood.

A "promoter," as used herein, is a DNA regulatory region capable of binding RNA polymerase in a mammalian cell and initiating transcription of an operably linked downstream (3' direction) sequence. For purposes of the present invention, a promoter sequence includes at least the minimum number of bases or elements necessary to initiate transcription of a gene of interest at levels detectable above background. Within the promoter sequence is a transcription initiation site, as well as RNA polymerase binding domains. Eukaryotic promoters will often, but not always, contain "TATA" boxes and other DNA motifs, such as "CAT" or "SP1" boxes. The promoter according to the invention comprises DNA sequence starting at least 2 kb, preferably 3 kb, more preferably 4 kb upstream to the initiation site of the messenger codifying for specific, relevant gene products. These sequences preferably contain known promoters' sequences elements, such as specific transcription binding sites, and distal sequences upstream of the gene, containing additional regulatory elements.

By "active selectively in afferent neurons" it is meant herein that the promoter is active mainly or only in the afferent neurons, preferably in afferent neurons of the bladder and drives transcription (i.e. expression) of the RNA.

Also, those of skill in the art will recognize that many such mammalian afferent neuron specific promoters are known, and additional afferent neuron specific promoters are continually being discovered. All such afferent neuron specific promoters are encompassed by the present invention. However, many cell-specific promoter candidates have been shown to display selectivity only when they express from their endogenous location in the cellular chromosomes (McCart et al., 2002; Vassaux et al., 1996). There is no way to predict how these promoters will behave when introduced into the genome of a non-integrative expression vector, such as HSV vectors. Notably, it cannot be anticipated whether afferent neuron-specific promoters will retain the same afferent neuron-specific activity. This is both because (a) the nucleosomes bound to the promoter could differ in several respects (for example they can be in a repressive or a permissive configuration) according to the location of the promoter (in the chromosomes versus in the extra-chromosomal vector genome, or even between different positions in cellular chromosomes) and also (b) because the accessibility of positive or negative transcription factors could also differ. This means that every promoter candidate should be thoroughly studied in each specific setting (i.e. episomal vector vs. chromosomal location) to establish whether it retains or not its afferent neuron-specific activity when placed into the vector genome, as we experimentally did (see results in Example 11 and FIG. 13).

In a preferred embodiment, the promoter according to the invention is selected from promoters of genes coding for sensory neuroreceptors, such as Transient Receptor Potential Vanilloid 1 (TRPV1) or Transient Receptor Potential cation channel subfamily M member 8 (TRPM8), or from promoters of genes coding for sensory neuromodulators or sensory neurotransmitters, such as the promoters of Substance P, PACAP, Calcitonin Gene Related Peptide (CGRP) of SEQ ID NO: 3 or SEQ ID NO: 4. Preferentially, promoter of genes coding for sensory neuroreceptors according to the invention is a promoter of the TRP gene family, more preferentially the promoter TRPV1 of SEQ ID NO: 1 or TRPM8 of SEQ ID NO: 2. Preferentially, promoters of genes coding for sensory neuromodulators or sensory neurotransmitters according to the invention is the CGRP of SEQ ID NO: 3 or SEQ ID NO: 4, or the promoter of genes involved in neurite outgrowth and stress response in sensory neurons, preferably the promoter of the gene encoding advillin (ADVL) of SEQ ID NO: 5 or SEQ ID NO: 6.

The viral expression vector of the invention is directed more particularly to vertebrate, preferably to mammals, more preferably primates and humans. Therefore, those skilled in the art will recognize that such promoters are specific to species and would be able to select homologous sequences of a particular species of interest. In particular, the promoters according to the invention are human homolog of rat TRPV1 of SEQ ID NO: 1 or human TRPM8 of SEQ ID NO: 2, or rat CGRP of SEQ ID NO: 3, or human CGRP of SEQ ID NO: 4, or rat advillin of SEQ ID NO: 5 or human advillin of SEQ ID NO: 6, amongst others.

By "long-term expression sequence" or "long-term expression element (LTE)" it is meant a nucleotide sequence operably linked to the transcription cassette included in the sequence of the viral expression vector, allowing to sustain the expression of a gene product for more than 15 to 45 days or 30 to 45 days, preferably 45 to 90 days, more preferably 90 to 365 days, even more preferably 365 days to several years or even more preferably during the life of the patient.

Long-term expression (LTE) sequences were identified in HSV-1 as a region of the latency-associated transcripts (LAT), which originate from the LAT-associated promoter (LAP). This LTE is located downstream of the LAT transcription start site. Indeed, viruses harboring a DNA fragment 3' of the LAT promoter maintained detectable promoter expression throughout latency (Lokensgard et al, 1997, Berthomme et al., 2000, 2001). Preferably, the LTE is comprised between about 1.5 kb to about 3 kb downstream of the LAT transcription start site (Perng et al., 1996). More recently, additional sequences, known as DNA insulators, have also been described both upstream and downstream the LTE region (Amelia et al., 2006). These sequences also contribute to provide long-term expression to a given transcription cassette probably by inhibiting epigenetic silencing, and also will be incorporated in the present invention as part of the LTE elements, to confer long-term expression to the transcription cassette. Interestingly, sequences conferring long-term expression to the transcription cassette (both the LTE and the DNA insulator sequences) can be placed either upstream and/or downstream the transcription cassette.

Those of skill in the art will recognize that other LTE-like sequences, as well as other DNA insulator sequences, have been described and are continually being discovered. All such LTE-like sequences and DNA insulator sequences are encompassed by the present invention.

In preferred embodiment, the viral expression vector of the invention comprises at least one nucleotide sequence that is transcribed into a non-coding nucleotides sequence inhibiting the synthesis of at least one protein selected from VAMP, SNAP-25 and syntaxin, which are part of the SNARE complex.

The SNARE complex (soluble N-ethylmaleimide-sensitive factor attachment protein receptor) is one of the two key components of the membrane fusion machinery with the SM (Sec1/Munc18) proteins. The SNARE complex comprises the vesicle-associated "v-SNAREs" (Vesicle Associated Membrane Proteins, VAMPs, particularly VAMP1, 2 and 3) and the target membrane-associated "t-SNAREs" Syntaxins (Syn-1, 2, 3, and 4) and Synaptosome-Associated Protein of 25 kDa (SNAP-25) that assemble into complexes to mediate different fusion events.

Therefore, one embodiment of the present invention is directed to methods able to silence a specific gene and/or to disrupt the corresponding encoded protein (a "gene of interest" or "targeted gene" or "selected gene"). By "silencing" a gene, we mean that expression of the gene product is reduced or eliminated, in comparison to a corresponding control gene that is not being silenced. Those of skill in the art are familiar with the concept of comparing results obtained with control vs. experimental results. Without being bound by theory, it is believed that silencing is characterized by specific mRNA degradation or mRNA block in translation after the expression of a non-coding complementary sequence such as antisense RNA (asRNA), a small hairpin RNA (shRNA), a microRNA (miRNA), or any other form of interfering RNA (iRNA) into cells.

As herein used, the term "antisense" relates to unmodified or chemically modified single-stranded nucleic acid molecules which are relatively short in general and which are able to hybridize to a unique sequence in the total pool of targets present in cells, the sequence of said nucleic acid molecule being complementary by virtue of Watson-Crick bp hybridization, to a specific mRNA and is able to inhibit said mRNA expression and then induce a blockade in the transfer of genetic information from DNA to protein.

In the context of the invention, "RNA interference" (hereinafter referred to as RNAi) is interpreted as a process by which a double stranded RNA (dsRNA) with a given sense nucleic sequence leads to the breakdown of all messenger RNA (mRNA) comprising said nucleic sequence, in a manner specific to said nucleic sequence. Although the RNAi process was originally demonstrated in *Caenorhabditis elegans*, it is now clear that the RNAi process is a very general phenomenon, and inhibition of human genes by RNAi has been achieved.

The process of RNAi can be achieved using small interfering RNA (or siRNA). These siRNAs are dsRNA of less than 30 nucleotides long, comprising in their sense sequence a sequence that is highly complementary to a fragment of the target mRNA. When a siRNA crosses the plasma membrane, the reaction of the cell is to destroy the siRNA and all the sequences comprising a highly complementary sequence. Thus, an mRNA with a fragment that is highly complementary to the siRNA sequence will be destroyed, the expression of this gene being thus inhibited.

shRNA may be also used as inhibitor according to the present invention. As used herein, an "shRNA molecule" includes a conventional stem-loop shRNA, which forms a precursor miRNA (pre-miRNA). "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, a conventional shRNA forms a primary miRNA (pri-miRNA) or a structure very similar to a natural pri-miRNA. The pri-miRNA is subsequently processed by Drosha and its cofactors into pre-miRNA. Therefore, the term "shRNA" includes pri-miRNA (shRNA-mir) molecules and pre-miRNA molecules.

In general, "reduced or eliminated" refers to a reduction or elimination of detectable amounts of the gene product by an amount in the range of at least about 10% to about 100%, or preferably of at least about 25% to 100%, or more preferably about 50% to about 100%, and most preferably from about 75% to about 100%. If desired, a reduction or elimination may be determined by any of several methods that are well known to those of skill in the art, and may vary from case to case, depending on the gene that is being silenced. For example, such a reduction or elimination of the expression of the gene product may be determined by quantification of the gene product (e.g. by determining the quantity of a protein, polypeptide or peptide that is made) or quantification of an activity of the gene product (e.g. an activity such as signaling or transport activity, activity as a structural component of the cell, activity such as enzymatic activity, etc.), or by observation and quantification of a phenotypic characteristic of the targeted cell in comparison to a control cell (e.g the presence or absence of a protein using specific antibodies). Any suitable means to determine whether or not a targeted gene has been silenced may be used.

In one embodiment, the non-coding nucleotides sequence according to the invention is selected from antisense RNA (asRNA), a small hairpin RNA (shRNA), a micro RNA (miRNA), or any other interfering RNA (iRNA), which inhibits the synthesis of at least one protein selected from VAMP, SNAP-25 and syntaxin.

In one embodiment, the viral expression vector comprises at least one nucleotide sequence that is transcribed into an asRNA inhibiting the synthesis of VAMP, SNAP-25 and/or syntaxin. In particular, the sequences of the asRNA used in the context of the present invention are VAMP2 antisense of SEQ ID NO: 7, SNAP25 antisense of SEQ ID NO: 8 and syntaxin antisense of SEQ ID NO: 9.

In a particular embodiment, the viral expression vector comprises at least one nucleotide sequence that is transcribed into an shRNA inhibiting the synthesis of VAMP, SNAP-25 and/or syntaxin.

In another embodiment, the viral expression vector comprises at least one nucleotide sequence that is transcribed into an miRNA inhibiting the synthesis of VAMP, SNAP-25 and/or syntaxin.

The RNA molecule that is encoded by the construct of the present invention ultimately forms a double-strand RNA molecule within the cell in which it is transcribed. In general, one strand of the double-strand RNA structure will be in the range of from about 10 to about 30 ribonucleotides in length, and preferably from about 19 to about 25 ribonucleotides in length.

In the case of asRNA, one of the double-strand RNA structure will be in the range of from about 100 to several hundreds of ribonucleotides in length. It could actually be as long as the target mRNA. Those of skill in the art will recognize that several viable strategies exist for forming such double-strand RNA.

Moreover, provision of multiple viral vectors with the same afferent neuron-specific promoter but which encode different silencing RNAs may be used within the practice of the invention.

Further, it should be possible to express more than one silencing RNA in a single viral vector, driven by a single afferent neuron-specific promoter, or by more than one promoter arranged in tandem (e.g. two or more promoters). Thus, the invention contemplates using a single viral vector for silencing more than one gene.

In another embodiment, the viral expression vector according to the invention comprises at least one nucleotide sequence coding for a wild-type or a modified toxin disrupting the SNARE complex or the ribosome complex or for an active fragment thereof.

Advantageously, the active fragment of the toxin is a bacterial neurotoxin, preferentially said bacterial neurotoxin is the light chain of said bacterial neurotoxin. In particular, the sequences of the toxins light chains used in the context of the present invention are the protein sequence light chain of the botulinum neurotoxin A (BoNT-A) of SEQ ID NO: 10 (coding nucleotides sequence SEQ ID: 11), the protein sequence light chain of the botulinum neurotoxin B (BoNT-B) of SEQ ID NO: 12 (coding nucleotides sequence SEQ ID: 13), the protein sequence light chain of the botulinum neurotoxin C1 (BoNT-C1) of SEQ ID NO: 14 (coding nucleotides sequence SEQ ID: 15), the protein sequence light chain of the botulinum neurotoxin E3 (BoNT-E3) of SEQ ID NO: 16 (coding nucleotides sequence SEQ ID: 17), the protein sequence light chain of the botulinum neurotoxin F1 (BoNT-F1) of SEQ ID NO: 18 (coding nucleotides sequence SEQ ID: 19) and the protein sequence light chain of the tetanic neurotoxin (TeNT) of SEQ ID NO: 20 (coding nucleotides sequence SEQ ID: 21).

In preferred embodiment, the viral expression vector according to the invention comprises at least one nucleotide sequence coding for a wild-type or a modified GAD67 protein or for an active fragment thereof, preferentially nucleotide sequence coding for a wild-type GAD67 protein of SEQ ID NO: 22 (coding nucleotides sequence SEQ ID: 23) or an active fragment thereof.

In preferred embodiment, the viral expression vector according to the invention comprises at least one nucleotide sequence coding for a wild-type or a modified RIP or for an active fragment thereof, preferentially said RIP is Saporin S6 protein of SEQ ID NO: 24 (coding nucleotides sequence SEQ ID: 25) or an active fragment thereof.

In preferred embodiment, the viral expression vector according to the invention comprises at least one nucleotide sequence coding for a wild-type or a modified NTR or an active fragment thereof, preferentially said NTR is nitroreductase nfnB protein of SEQ ID NO: 26 (coding nucleotides sequence SEQ ID: 27) or an active fragment thereof.

As used herein, the term "coding sequence" refers to a ribonucleic acid (e.g., RNA) sequence that, when it is translated, produces the polypeptide of interest. The polypeptide can be encoded by a full-length coding sequence or by any portion of the coding sequence so long as the desired activity or functional properties (e.g., enzymatic activity, ligand binding, signal transduction, etc.) of the full-length or fragment is retained.

In one embodiment, the invention relates to a viral expression vector that comprises at least one nucleotide sequence coding for a wild-type or a modified botulinum neurotoxin of *Clostridium botulinum* of any serotype or for an active fragment thereof, preferably the light chain of *Clostridium botulinum* neurotoxin of any serotype.

In another embodiment, the invention is directed to a viral expression vector that comprises at least one nucleotide sequence coding for a wild-type or a modified tetanus neurotoxin of *Clostridium tetani* or for an active fragment thereof, preferably the light chain of *Clostridium tetani* neurotoxin.

Clostridial neurotoxins are produced by various species of the genus *Clostridium*, for example several strains of *C. botulinum* and *C. tetani*. When Clostridium toxin molecules enter into the neuron, the light chain disrupts the proteins that form the SNARE complex located at the presynaptic nerve terminal. This prevents the neurotransmitter filled synaptic vesicles from attaching to the presynaptic membrane, therefore inhibiting exocytosis of the neurotransmitter from the presynaptic nerve terminal. At present, there are eight different classes of the neurotoxins known: tetanus toxin and botulinum neurotoxin in its serotypes A, B, C, D, E, F and G, all of which share homology and similar molecular structures. Within said serotypes, sub-types are also well documented, such as subtypes $A_1$-$A_3$, $B_1$-$B_3$, etc.

Botulinum neurotoxin serotypes A, C, and E cleaves the SNAP-25 protein located on the plasma membrane of the presynaptic nerve terminals. Because SNAP-25 is necessary for the fusion of neurotransmitter-filled vesicles with the plasma membrane and their release during exocytosis, its cleavage causes a highly specific blockade of vesicular neurotransmitter release at somatic and autonomic presynaptic nerve terminals. Botulinum neurotoxin serotypes B, D, F, and G cleave the synaptobrevin (VAMP) protein, so that the vesicles cannot fuse to the cell membranes. Each botulinum neurotoxin or its light chain fragment cleaves one of the SNARE proteins except for botulinum neurotoxin C, or its light chain fragment, which cleaves both SNAP25 and syntaxin 1a. Preferably, according to the invention the serotypes of botulinum neurotoxin are A, B, C, E and F.

The structure of Clostridial neurotoxins has been well-documented (Habermann et al, 1986; Sugiyama et al 1980); each of these documents is hereby incorporated in its entirety by reference thereto]. In this regard, Clostridial neurotoxins comprise two polypeptide chains, the heavy chain (H-chain), which has a molecular mass of approximately 100 kDa, and the light chain (L-chain), which has a molecular mass of approximately 50 kDa, joined together by a disulphide bond.

The different serotypes of botulinum toxin vary in the animal species that they affect and in the severity and duration of the paralysis they evoke. For example, it has been determined that botulinum toxin type A is 500 times more potent, as measured by the $LD_{50}$ in mice, than botulinum toxin type B. Additionally, botulinum toxin type B has been determined to be non-toxic in primates at a dose of 480 U/kg which is about 12 times the primate $LD_{50}$ for botulinum toxin type A. Naturally, botulinum toxin binds with high affinity to neurons, is translocated into the neuron and blocks the release of neurotransmitters.

In a particular embodiment, the invention is directed to a viral expression vector that comprises at least one nucleotide sequence coding for a wild-type or a modified tetanus neurotoxin of *Clostridium tetani* or for an active fragment thereof to cleave the protein VAMP-2.

In a particular embodiment, the invention is directed to a viral expression vector that comprises at least one nucleotide sequence coding for a wild-type or a modified botulinum neurotoxin of *Clostridium botulinum* of serotype B, D, F, and G or for an active fragment thereof to cleave the protein VAMP-2.

In a particular embodiment, the invention is directed to a viral expression vector that comprises at least one nucleotide sequence coding for a wild-type or a modified botulinum neurotoxin of *Clostridium botulinum* of serotype A and E or for an active fragment thereof to cleave the protein SNAP-25.

In a preferred embodiment, the invention is directed to a viral expression vector that comprises at least one nucleotide sequence coding for a wild-type or a modified botulinum neurotoxin of *Clostridium botulinum* of serotype C or for an active fragment thereof to cleave the proteins SNAP25 and syntaxin 1a.

In a preferred embodiment, the nucleotide sequence of transgene according to the invention codes for a wild-type or a modified protein silencing or inhibiting the transduction of the neurotransmitter signal in postsynaptic cell which is fused to a signal peptide domain. The signal peptide according to the invention is selected according to the intracellular compartment where transcript or protein targeted to silence or inhibit the transduction of the neurotransmitter signal in postsynaptic cell is located. Therefore, those skilled in the art will recognize that such signal peptides are specific to intracellular compartment and would be able to select the appropriate corresponding nucleotide sequences to be fused to the nucleotide sequence coding for the protein silencing or inhibiting neurotransmission or synaptic transmission according to the invention. In particular, the signal peptides according to the invention comprise at least the luminal, transmembrane or cytoplasmic domains of proteins selected from VAMP2 or Syntaxin 1a In a particular embodiment, fusion protein according to the invention comprises a signal peptide domain selected from luminal, transmembrane or cytoplasmic signal peptide domains, preferentially the luminal, transmembrane or cytoplasmic signal peptide domains of the SNARE proteins, the substance P or CGRP sequences. Such signal peptide domains include notably the signal peptide of syntaxin 1a (BoNTB-STX) of SEQ ID NO: 30 (coding nucleotides sequence SEQ ID: 31) and the signal peptide of VAMP2 (BoNTC-VAMP) of SEQ ID NO: 32 (coding nucleotides sequence SEQ ID: 33). Thus, according to a particular embodiment of the invention, the fusion protein comprises a modified bacterial neurotoxin, such as e.g., a modified botulinum neurotoxin, and a signal peptide such as e.g., the signal peptide of syntaxin 1a (BoNTA-STX) of SEQ ID NO:

28 or (BoNTB-STX) of SEQ ID NO: 30 (coding nucleotides sequence SEQ ID: 31) and the signal peptide of VAMP2 (BoNTC-VAMP) of SEQ ID NO: 32 (coding nucleotides sequence SEQ ID: 33).

In one specific embodiment, the fusion protein according to the invention comprises the wild-type or modified *Clostridium botulinum* neurotoxin of serotype A, B, C, E or F linked to the signal peptide of syntaxin 1a, preferentially the fusion protein comprises the wild-type or modified *Clostridium botulinum* neurotoxin of serotype A linked to the signal peptide of syntaxin 1a (BoNTA-STX) of SEQ ID NO: 28 (coding nucleotides sequence SEQ ID: 29) or the fusion protein comprises the wild-type or modified *Clostridium botulinum* neurotoxin of serotype B linked to the signal peptide of syntaxin 1a (BoNTB-STX) of SEQ ID NO: 30 (coding nucleotides sequence SEQ ID: 31).

In one specific embodiment, the fusion protein according to the invention comprises the wild-type or modified *Clostridium botulinum* neurotoxin of serotype A, C and E linked to the signal peptide of VAMP2, preferentially the fusion protein comprises the wild-type or modified *Clostridium botulinum* neurotoxin of serotype C linked to the signal peptide of VAMP2 (BoNTC-VAMP) of SEQ ID NO: 32 (coding nucleotides sequence SEQ ID: 33).

In one specific embodiment, the fusion protein according to the invention comprises the wild-type or modified *Clostridium botulinum* neurotoxin of any serotype linked to the signal peptide of Substance P.

In one specific embodiment, the fusion protein according to the invention comprises the wild-type or modified *Clostridium botulinum* neurotoxin of any serotype linked to the signal peptide of CGRP sequence.

The present invention is also directed to a viral expression vector according to the invention, comprising at least:
a) one nucleotide sequence coding for a wild type or modified neurotoxin of *Clostridium tetani* or *botulinum* or for an active fragment thereof; and/or
b) one nucleotide sequence whose transcripts inhibit the synthesis of the protein VAMP, SNAP-25 and/or syntaxin; and/or
c) one nucleotide sequence coding for a wild type or modified GAD67 protein or for an active fragment thereof; and/or
d) one nucleotide sequence coding for a wild type or modified RIP or for an active fragment thereof; and/or
e) one nucleotide sequence coding for a wild type or modified NTR or for an active fragment thereof.

In a preferred embodiment, the viral expression vector according to the invention comprises:
i. one said long-term expression sequence operably linked to two transcription cassettes according to the invention; or
ii. two long-term expression sequences both operably linked to one said transcription cassette according to the invention; and wherein:
 a) one transcription cassette according to the invention harbors a coding sequence according to the invention, and the second transcription cassette according to the invention harbors a sequence that is transcribed into a non-coding nucleotide according to the invention; or
 b) both transcription cassettes according to the invention harbor a nucleotide sequence coding for a non-coding nucleotides sequence according to the invention; or
 c) both transcription cassettes according to the invention harbor a nucleotide sequence coding for a wild type or modified neurotoxin of *Clostridium tetani* and/or *botulinum* or for an active fragment thereof; or for a wild type or modified GAD67 protein or for an active fragment thereof; or for a wild type or modified RIP or for an active fragment thereof; or for a wild type or modified NTR or for an active fragment thereof.

In a particular embodiment, the invention relates to a viral expression vector, wherein
i. one said long-term expression (LTE) sequence is operably linked to two transgenic transcription cassettes according to the invention; or
ii. two separated long-term expression (LTE) sequences are each operably linked to one said transcription cassette according to the invention;
and wherein:
a) one transcription cassette according to the invention harbors a sequence coding for a bacterial neurotoxin, a GAD67, a RIP, or a NTR according to the invention, and the second transgenic transcription cassette according to the invention harbors a sequence that is transcribed into a non-coding nucleotides sequence according to the invention that inhibit the synthesis of the protein VAMP, SNAP-25 and/or syntaxin; or
b) both transcription cassettes according to the invention harbor a nucleotide sequence coding for a non-coding nucleotides sequence according to the invention that inhibit the synthesis of at least one protein selected from VAMP, SNAP-25 and/or syntaxin; or
c) both transgenic transcription cassettes according to the invention harbor a promoter and a nucleotide sequence coding for a wild type or modified neurotoxin of *Clostridium tetani* and/or *botulinum* or for an active fragment thereof; or a wild type or modified GAD67 protein or for an active fragment thereof; or a wild type or modified RIP or for an active fragment thereof; or a wild type or modified NTR or for an active fragment thereof.

In a preferred embodiment, the invention relates to a viral expression vector, wherein at least one of said transgenic transcription cassettes according to the invention harbors a promoter and a sequence coding for the wild-type protein GAD67 or for an active fragment thereof.

In a more preferred embodiment, the invention relates to a viral expression vector, wherein one of the said transgenic transcription cassettes according to the invention harbors a promoter and a sequence coding for the wild-type protein GAD67 or for an active fragment thereof; and one of the said transgenic transcription cassettes according to the invention harbors a promoter and a sequence coding for a wild type or modified neurotoxin of *Clostridium tetani* and/or *botulinum* or for an active fragment thereof.

In a preferred embodiment, the invention relates to a viral expression vector, wherein at least one of said transgenic transcription cassettes according to the invention harbors a promoter and a sequence coding for the wild-type RIP or for an active fragment thereof.

In a more preferred embodiment, the invention relates to a viral expression vector, wherein one of the said transgenic transcription cassettes according to the invention harbors a promoter and a sequence coding for the wild-type RIP or for an active fragment thereof; and one of the said transgenic transcription cassettes according to the invention harbors a promoter and a sequence coding for a wild type or modified neurotoxin of *Clostridium tetani* and/or *botulinum* or for an active fragment thereof; and/or a sequence coding for the wild-type protein GAD67 or for an active fragment thereof, and/or a sequence coding for the wild-type NTR of for an active fragment thereof.

In a preferred embodiment, the invention relates to a viral expression vector, wherein at least one of the transgenic transcription cassettes according to the invention comprises a promoter and a sequence coding for the wild-type NTR or for an active fragment thereof.

In a more preferred embodiment, the invention relates to a viral expression vector, wherein said viral expression vector comprises at least 2 transgenic transcription cassettes, wherein:
- at least one of the said transgenic transcription cassettes according to the invention comprises a promoter and a sequence coding for the wild-type NTR or for an active fragment thereof; and
- At least one of the said transgenic transcription cassettes according to the invention comprises a promoter and a sequence coding for a wild type or modified neurotoxin of *Clostridium tetani* and/or *botulinum* or for an active fragment thereof; and/or a sequence coding for the wild-type protein GAD67 or for an active fragment thereof; and/or a sequence coding for the wild type RIP or for an active fragment thereof.

In a second aspect, the invention relates to a composition comprising the viral expression vector of the present invention for use as a medicament.

In a third aspect, the invention is directed to a pharmaceutical composition comprising at least one viral expression vector according to the invention.

Advantageously, the pharmaceutical composition according to the invention is used for the treatment of the NDO.

The invention also relates to a pharmaceutical composition comprising:
a) at least one viral expression vector comprising at least one nucleotide sequence transcribed into a non-coding nucleotides sequence, preferably selected from anti-sense RNA (asRNA), a small hairpin RNA (shRNA) or a microRNA (miRNA), more preferably antisense RNA (asRNA), to inhibit the synthesis of at least one protein selected from VAMP, SNAP-25 and syntaxin; and/or
b) at least one viral expression vector comprising at least one nucleotide sequence coding for a wild-type or a modified bacterial neurotoxin disrupting the SNARE complex or for an active fragment thereof, preferably the light chain of a bacterial neurotoxin, and wherein the said bacterial neurotoxin is advantageously the neurotoxin of *Clostridium tetani* and/or *Clostridium botulinum* of any serotype, preferably serotypes A, B, C, E and F; and/or
c) at least one viral expression vector comprising at least:
    one nucleotide sequence coding for a wild type or modified neurotoxin of *Clostridium tetani* or *botulinum* or for an active fragment thereof, and
    one nucleotide sequence whose transcripts inhibit the synthesis of the protein VAMP, SNAP-25 and/or syntaxin; and/or
d) at least one viral expression vector according to the invention, wherein
    i. one said long-term expression (LTE) sequence is operably linked to two transgenic transcription cassettes according to the invention; or
    ii. two long-term expression (LTE) sequences are each operably linked to one said transgenic transcription cassette according to the invention; and wherein:
        one transgenic transcription cassette according to the invention harbors a promoter and sequence coding for said neurotoxin, and the second transgenic transcription cassette according to the invention harbors a promoter and a sequence nucleotide inhibiting the synthesis of the protein VAMP, SNAP-25 and/or syntaxin; or
        both transgenic transcription cassettes according to the invention harbor a promoter and a nucleotide sequence coding for a non-coding nucleotides sequence inhibiting the synthesis of at least one protein selected from VAMP, SNAP-25 and/or syntaxin; or
        both transgenic transcription cassettes according to the invention harbor a nucleotide sequence coding for a wild type or modified neurotoxin of *Clostridium tetani* and/or *botulinum* or for an active fragment thereof for simultaneous, separated or staggered use for treating NDO.

In a particular embodiment, the pharmaceutical composition according to the invention, further comprises at least one viral expression vector comprising at least one nucleotide sequence coding for the wild-type protein GAD67 and/or RIP and/or NTR, or for an active fragment thereof.

In a particular embodiment, the pharmaceutical composition according to the invention, comprises at least one viral expression vector comprising at least one nucleotide sequence coding for the wild-type protein GAD67 or for an active fragment thereof; and/or at least one nucleotide sequence coding for a wild type or modified neurotoxin of *Clostridium tetani* and/or *botulinum* or for an active fragment thereof; and/or for the wild-type RIP or for an active fragment thereof; and/or for the wild-type NTR or for an active fragment thereof.

In a fourth aspect, the present invention relates to a kit comprising at least one viral expression vector or the pharmaceutical composition according to the invention, or the pharmaceutical composition according to the invention, and an electrical stimulation system comprising electrodes to be implanted on the sacral anterior roots, such as S2-S3-S4, to apply intermittent stimulation pulse trains in order to achieve a sustained detrusor muscle contraction with intervals of urethral sphincter relaxation allowing urine to flow.

By "electrical stimulation" it is meant herein that an electrical stimulation is applied, via electrodes, in bursts of a few seconds, separated by longer gaps, to sustain pressure in the bladder, while allowing the external urethral sphincter to relax rapidly between bursts, causing urine to flow during these gaps. The preferred electrical stimulation system is the Finetech-Brindley stimulator (ref 6 à 19 in Ren et al, 2015).

The invention further relates to a method for the treatment of patient suffering from NDO comprising the steps of:
a) preparing at least one viral expression vector according to the invention;
b) injecting the viral expression vector of step a) in the bladder wall (detrusor muscle);
c) implanting electrical stimulation system via electrodes implanted on the sacral anterior roots, such as S2-S4 or S3-S4, to elicit by stimulation in bursts of a few seconds, separated by longer gaps, a sustained pressure in the bladder, while allowing the external urethral sphincter to relax rapidly between bursts, causing urine to flow.

The following examples merely intend to illustrate the present invention.

DESCRIPTION OF THE FIGURES

FIG. 3. A. This figure represents the region of the genome of amplicon vectors used in this invention that carries the two eukaryotic transcription cassettes. One of them expresses the reporter GFP (or the fusion GFP-rLuc) gene under the control of the IE4/5 immediate-early promoter of HSV-1. The second transcription cassette expresses any of the therapeutic functions that inhibit or silence neurotransmission, as described in this invention. A DRG-specific promoter drives expression of the transcription cassettes, whereas the whole cassette is surrounded by sequences conferring long-term expression (black squares). B. This figure shows some of the transcription cassettes used in this study to demonstrate the efficacy and selectivity of the genetic constructs. These are: vector A: HCMV-TeNT light chain, (LC); vector B: HCMV-BoNT-A (LC); vector C: HCMV-BoNT-C (LC); vector D: SNAP25 antisense RNA; vector E: HCMV-Luciferase; vector F: TRPV1-Luciferase. BoNT-A (LC) and BoNT-C (LC) are fusion proteins that express a C-terminal HIS-tag, as no efficient anti-BoNT antibodies are available. HCMV is a strong and ubiquitous viral promoter, whereas TRPV1 is a DRG-selective promoter. Others vectors, expressing other botulinum toxins, or fusion SNARE/light chain toxins, or antisense RNA addressed to other SNARE proteins, or the human GAD67 protein, or a RIP protein such as Saporin S6, are not shown in this Figure.

FIG. 4 shows the expression of BoNT-A (LC), BoNT-C (LC) and TeNT (LC) in Gli36 (a cell line derived from a human glioblastoma) and BHK21 (hamster fibroblast cells) cell lines. Gli36 and BHK21 cells were infected with the amplicon vectors HCMV-Luc, HCMV-BoNT-A (LC), HCMV-BoNT-C (LC), or HCMV-TeNT (LC) (shown in FIG. 2B). Infected cells were then fixed and expression of the toxins was demonstrated using specific antibody in a Western assay. Anti-TeNT antibodies were used to reveal TeNT (LC); anti-HIS antibodies were used to reveal both BoNT-A (LC) and BoNT-C (LC).

FIG. 5 shows that the toxin TeNT (LC) expressed in Gli36 cells and present in cell extracts possesses proteolytic activity with respect to VAMP2. Gli36 cells were infected with the amplicon vector expressing HCMV-TeNT (LC) at a multiplicity of infection (MOI) of 1. The infection was terminated 2 days later and protein extracts were prepared. These extracts were incubated in a suitable buffer (50 mM Hepes, 400 mM NaCl, 5 mM dithiothreitol and 2 µM ZnSO4) containing the target protein of TeNT, i.e VAMP2. After incubation for 24 h at 37° C. with 2.5, 5, and 10 µL of cell extracts, westerns blots were performed using anti-VAMP2 antibody to reveal the proteolytic activity of TeNT (LC) expression.

FIG. 6A shows that at 48 hours post-infection (hpi) of human neuroblastoma SH-S5Y5 cells with amplicon vectors expressing HCMV-BoNT-A (LC) (see FIG. 3B), there is a significant decrease in cellulo of SNAP25 protein levels relative to the control cells infected with a vector expressing luciferase (HCMV-Luc) or not infected (Mock). Protein levels were detected by Western blot assay using anti-SNAP25 antibodies. Note that BoNT-A (LC) cleaves SNAP25 into two fragments. The antibodies used in these experiments recognize both the native SNAP25 protein (upper band) and the large fragment of the cleaved protein (lower band). B shows that at 48 hours post-infection (hpi) of human neuroblastoma SH-S5Y5 cells with amplicon vectors expressing HCMV-BoNT-C (LC) (see FIG. 3B), there is a significant decrease in cellulo of both SNAP25 and Syntaxin (STX) protein levels relative to the control cells infected with a vector expressing luciferase (HCMV-Luc) or not infected (Mock). Protein levels were detected by Western blot assay using anti-SNAP25 and anti-STX antibodies. Note that BoNT-C (LC) cleaves SNAP25 into two fragments. The antibodies used in these experiments recognize both the native SNAP25 protein (upper band) and the large fragment of the cleaved protein (lower band).

FIG. 7. Transcription cassettes carried by recombinant and amplicon vector genomes.

Figure 2:
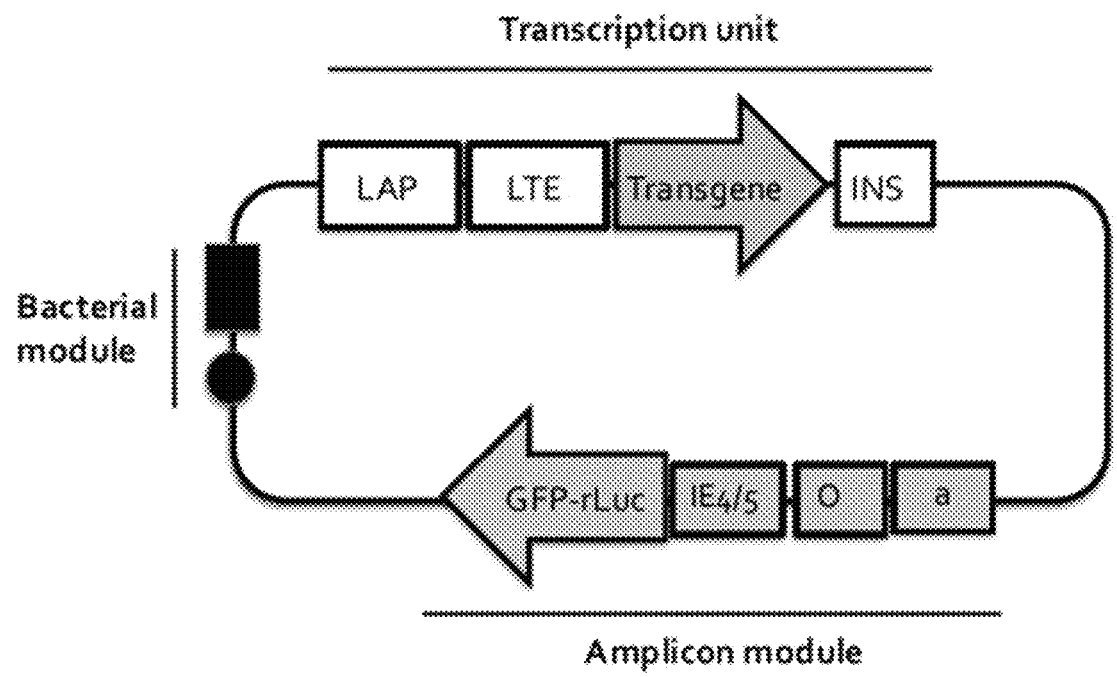
FIG. 2. Genome of amplicon vectors (the amplicon plasmid).
Amplicon plasmids are standard *E. coli* plasmids generally carrying three modules: (1) The bacterial module, which contains the Col E1 sequence for plasmid replication in bacteria, and a gene conferring resistance to an antibiotic, generally ampicillin (in black). (2) The amplicon module, which contains an HSV-1 origin of DNA replication, generally OriS(O), and a packaging signal (a) allowing amplification and packaging of a concatemeric form of the amplicon plasmid; in addition, this module generally express a reporter protein (in our case, either a GFP protein, or a fusion GFP/*renilla* luciferase (rLuc) protein) driven by the HSV-1 immediate early promoter 1E4/5. (3) The third module (in white) is the transcription unit, containing the DRG-specific transcription cassette (grey arrow labeled Transgene) placed between the LTE and INS sequenced, designed to inhibit or silence neurotransmission stably and selectively in sensory neurons, as described in this invention. The different transcription cassettes that are introduced into the amplicon plasmid to generate the amplicon vectors are shown in FIG. 3.

This figure shows some of the transcription cassettes that are carried and expressed by the recombinant and amplicon HSV-1 vectors. These transcription cassettes are classified into three families. Members of the A2 family are transcription cassettes expressing different therapeutic gene products (proteins or antisense RNA or miRNA), driven by the strong and ubiquitous HCMV promoter. Vectors carrying the A2 transcription cassettes are used to study the impact of these gene products on neurotransmission (cleavage of SNARE proteins and inhibition of neurotransmitter release), thus allowing to select the most efficient transgenes in the context of this invention. Members of the A5 family are transcription cassettes expressing the reporter gene firefly luciferase (fLuc) driven by different DRG-selective candidate promoters. These vectors are used to study the intensity, selectivity, and duration of expression in cultured neurons and in explanted peripheral ganglia, thus allowing identifying the most selective vectors in the context of this invention. Finally, members of the A8 family of vectors express therapeutic transcription cassettes (therapeutic gene products driven by DRG-selective promoters), thus allowing selecting vectors with high therapeutic potential in vivo, in the context of this invention. It should be noted that, as shown in FIG. 2, amplicon vectors also express a GFP/rLuc transgene driven by the HSV-1 IE4/5 promoter.

Abbreviations:
Gene products:
TeNT: light chain of Tetanus neurotoxin
BoNT-X: light chains of Botulinum neurotoxins BoNT-A, -B, -C, -D, -E, or F
BoNT-X-SNARE-Y: fusion proteins in which the light chain of botulinum neurotoxins are fused to the signal and transmembrane peptides of SNARE proteins. More precisely, these transgenes express BoNT-A-syntaxin, BoNT-B-syntaxin or BoNT-C-Vamp2.
GAD67: glutamic acid decarboxylase of 67 kD
NTR: nitroreductase.
Luc: firefly luciferase (fLuc).
Antisense-SNARE: antisense RNA to the SNARE proteins SNAP25, VAMP2 or Syntaxin.
Promoters:
Human elongation factor 1 promoter (EF1A), rat Transient Receptor Potential Vanilloide 1 (rTRPV1), human and rat Calcitonin Gene-Related Peptide (hCGRP and rCGRP), rat Acid-Sensing Ion Channel 3 (rASIC3), and human and rat Advillin (hADVL and rADVL) promoters.

Figures 8, 9:
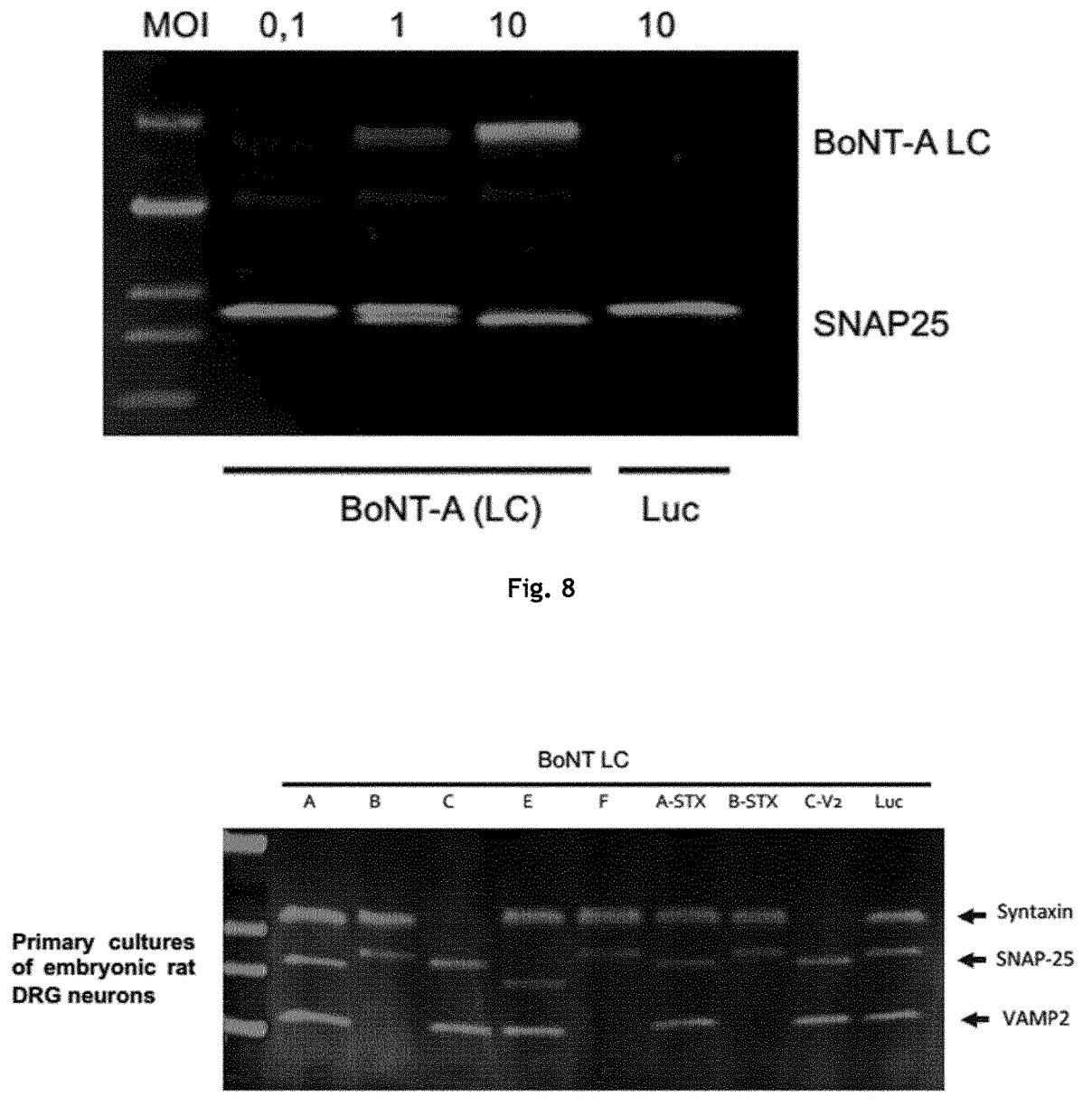

FIG. 8. BoNT-A expressed from amplicon vectors cleave the SNARE protein SNAP25 in SH-SY5Y cells.

Human neuroblastoma cells (SH-S5Y5) are infected at an MOI of 01, 1.0, and 10.0 pfu/cell with amplicon vectors expressing transcription units A2-CMV-BoNT-A (LC) or A2-CMV-Luc, driven in both cases by HCMV promoter. The following day, infections were stopped, and cell proteins are analysed by Western blots using antibodies specific for BoNT-A LC and SNAP25. The higher part of the Western blot shows that increasing amounts of BoNT-A LC correspond to increasing MOI, demonstrating that the vectors used do express this protein in the infected cells. The lower part of the blots shows cleavage of SNAP25, the protein from the SNARE complex that is the natural target of BoNT-A, thus producing two fragments. At the lower MOI, mainly the native (not cleaved) form of SNAP25 is observed. At intermediate MOI, both the native and the cleaved form (the slightly lower band) can be seen, while at the higher MOI most of the SNAP25 protein is cleaved, since only the lower fragment of the doublet can be observed. This demonstrates that BoNT-A LC synthesized in SH-S5Y5 cells is able to cleave SNAP25. In contrast, in SH-S5Y5 cells infected with the vector expressing Luc, no cleavage of SNAP25 is observed.

FIG. 9. Light chains of botulin neurotoxins cleave SNARE proteins in infected neurons. Primary cultures of rat embryonic dorsal root ganglia (DRG) neurons are infected at an MOI of 10 pfu/cell with amplicon vectors expressing transcription units A2-CMV-BoNT-A, A2-CMV-BoNT-B, A2-CMV-BoNT-C, A2-CMV-BoNT-E, and A2-CMV-BoNT-F. Neurons were also infected with amplicon vectors expressing A2-CMV-BoNT-A-syntaxin (STX), A2-CMV-BoNT-B-syntaxin (STX), and A2-CMV-BoNT-C-VAMP2 (V2). Vector expressing A2-CMV-Luc was used as negative control. In all cases, HCMV promoter drove expression of the transcription cassettes. The following day, infections were stopped and cell proteins were analyzed by Westerns blots. As shown in the figure, each BoNT LC synthesized in the neurons cleaved the expected SNARE protein: thus, the light chains of BoNT-A, -C and -E, cleaved SNP25, as evidenced by the decrease in size of this protein, whereas the light chains of BoNT-B, and -F, cleaved VAMP2, which is no more detectable in the blots. In addition, BoNT-C also cleaved Syntaxin (STX), also no more visible in the blots. BoNT-C is the only botulin toxin described to cleave two different SNARE proteins (SNAP25 and STX). The light chains of botulinum toxins fused to the signal and transmembrane peptides of SNARE proteins cleaved the corresponding SNARE proteins exactly as the parental non-fused toxins did. The lane Luc shows the positions of native, non-cleaved, SNARE proteins (arrows). This figure therefore demonstrates that the light chains of botulin toxins (fused or not with fragments of the SNARE proteins) synthesized in sensory neurons upon vector infection, are able to cleave their corresponding target proteins.

Figure 10:
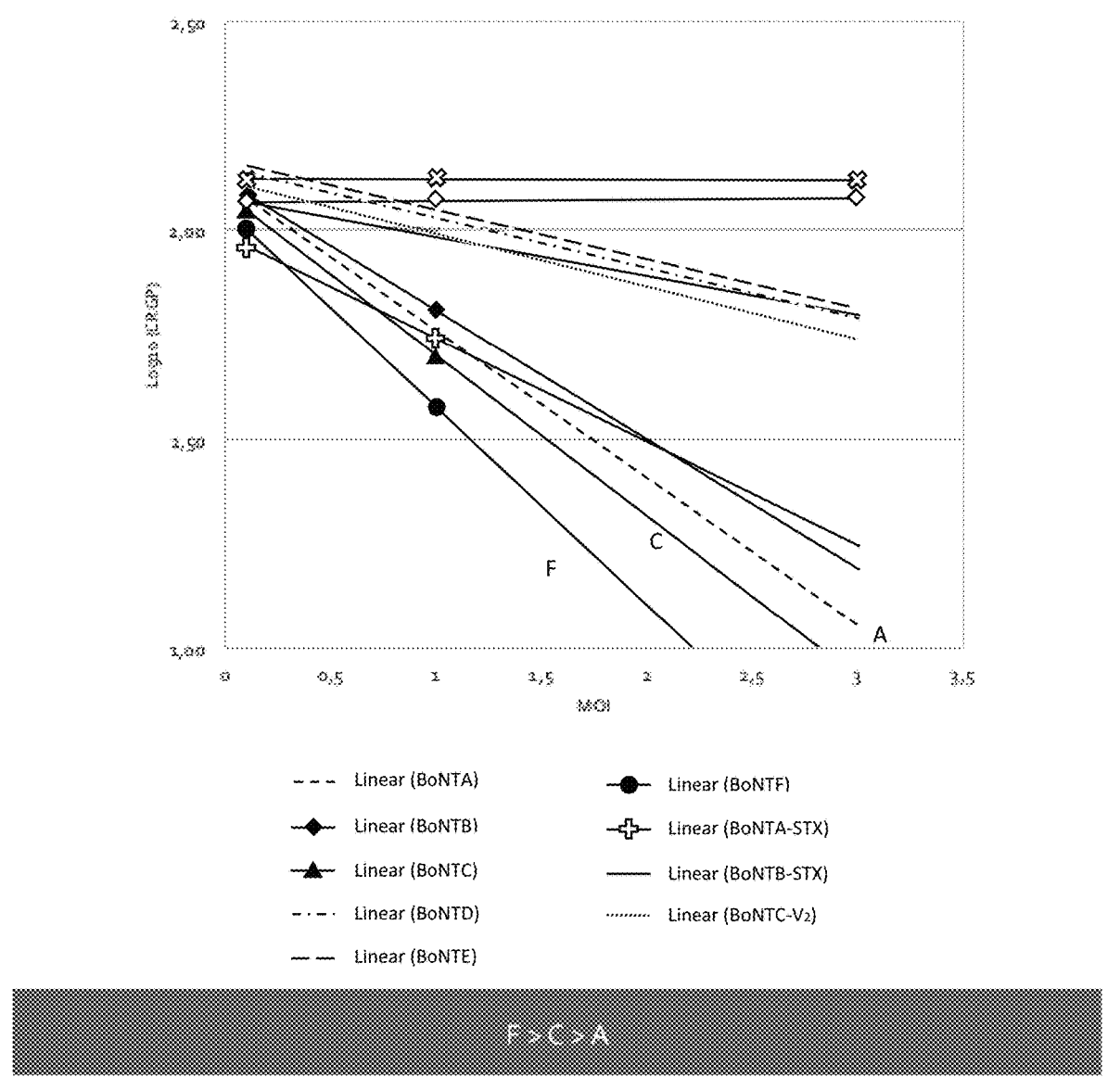

FIG. 10. Light chains of botulin toxins inhibit release of neuropeptides in sensory neurons.

Primary cultures of rat embryonic DRG neurons are infected at increasing MOI (from 0.5 to 3 pfu/cell) with amplicon vectors expressing A2-CMV-BoNT-A, A2-CMV-BoNT-B, A2-CMV-BoNT-C, A2-CMV-BoNT-D, A2-CMV-BoNT-E, and A2-CMV-BoNT-F.

Neurons were also infected with amplicons expressing A2-CMV-BoNT-A-syntaxin, A2-CMV-BoNT-B-syntaxin, and A2-CMV-BoNT-C-VAMP2. Vector expressing A2-CMV-Luc was used as negative control. Neurons were also infected with vehicle only (mock). The following day, the infected neurons were treated with 75 mM KCl to stimulate release of CGRP, a neuropeptide normally synthesized in DRG neurons. Thirty minutes before and thirty minutes after KCl treatment, 100 microliters aliquots were taken from the culture media and assessed for the presence of CGRP by ELISA (using the CGRP ELISA kit from Spi Bio, ref N° A05482). Results, expressed as linear regression profiles after logarithm conversion, show that all toxins inhibited CGRP release but that they do it with different intensities, with BoNT-F, BoNT-C and BoNT-A being the most effective in this respect. In mock-infected neurons, as well as in neurons infected with the vector expressing Luc, no inhibition of CGRP release was observed. These results clearly indicate that cleavage of SNARE proteins by BoNT LC results in inhibition of neuropeptide release, and that BoNT-F is the most efficient in this respect.

FIG. 11. GAD67 expressed from amplicon vectors induces synthesis and extracellular release of GABA (gamma amino-butyric acid).

7A) Glioblastoma cells (Gli36) were infected at MOI 0.1, 1.0 and 10 pfu/cell with amplicon vectors expressing A2-CMV-GAD67 or A2-CMV-Luc. The following day, infections were stopped and cell proteins were analyzed by Western blots, using antibodies specific for GAD67 and GAPDH (a housekeeping gene used as internal control). Extracts from rat brain were used as positive controls to identify endogenous GAD67. FIG. 11A shows that expression of GAD67 increases with the MOI, demonstrating that vector A2-CMV-GAD67 does express this protein.

7B) Primary cultures of rat embryonic DRG neurons were infected at MOI 0.1, 1.0 and 10 pfu/cell with vectors expressing A2-CMV-GAD67 or A2-CMV Luc. The following day infections were stopped and both, intracellular and extracellular, concentrations of GABA were evaluated using Resazurine assay, which is a fluorescence-coupled assay for GABA (the assay is performed as indicated in Ippolito et al., 2014). The upper panel shows that the amount of intracellular GABA increases with the MOI, while the lower panel shows the increase of extracellular GABA. The channel labeled GABA is a positive control for the Resazurine assay. This result clearly shows that expression of GAD67 from the A2-CMV-GAD67 vector increases synthesis of intracellular GABA and its release to the extracellular medium.

FIG. 12. Nitroreductase (NTR) activates the nitro compound 7'nitrocoumarin and induces cell death in the presence of mitronidazole (MTZ).

8A) Human glioblastoma (Gli36) cells were infected with amplicon vectors expressing A2-CMV-NTR or A2-CMV-Luc at an MOI of 1.0 pfu/cell. Two days later, infections were stopped and protein extracts were prepared and used to assess the activation of 7'nitrocoumarin, using a fluorescence-coupled assay (assay performed as in Muller et al. 2015). FIG. 12A shows that only the proteins extracted from cells infected with vector A2-CMV-NTR induced significant activation of 7'nitrocoumarin, demonstrating that functional NTR was expressed in Gli36 cells infected with A2-CMV-NTR.

8B). To assess whether expression of NTR induced cell death in the presence of metronidazole (MTZ), Gli36 cells were infected with amplicon vectors A2-CMV-NTR or A2-CMV-Luc at an MOI of 1.0 pfu/cell. The following day cells were incubated with or without MTZ (0.5. mM) for 24 hours. Infections were then stopped and cell viability was assessed using the MTT assay (as indicated by Carmichael et al., 1987). The figure shows that MTZ significantly increased cell death of infected cells. Mock: non-infected cells.

FIG. 13. Analysis of the selectivity of expression of DRG-selective promoter candidates in autonomic and sensory ganglia from adult rats.

Rat adult sensory ganglia (DRG), autonomic sympathetic ganglia (superior cervical ganglia, SCG), and autonomic parasympathetic ganglia (paracervical ganglia, GPC) were explanted and kept as organotypic cultures. After 3 days, the ganglia were individually infected with vectors expressing A5-TRPV1-Luc, A5-rCGRP-Luc, A5-ASIC3-Luc, or A5-EF1A-Luc, all of them expressing firefly luciferase (fLuc), but driven respectively by the following promoters: rat TRPV1 (rTRPV1), rat CGRP (rCGRP), rat ASIC3 (rASIC3), and EF1a, a non-selective promoter serving as general control. Each ganglion was infected with $10^6$ vector particles. The vectors also express renilla luciferase (rLuc) driven by a viral promoter (HSV-1 IE4/5). The following day infections were stopped and cells extracts were prepared for luciferase tests using Dual-luciferase reporter assay system from Promega. Results are expressed as ratio of fLuc/rLuc and were normalized as percentage of expression of the EF1a promoter in each of DRG (left), SCG (center) and GPC (right). FIG. 13 shows that some candidate promoters, such as rTRPV1 and rCGRP promoters, express significantly higher levels of fLuc in DRG than in autonomic ganglia, while other promoters, such as rASIC3, do not display preferential activity in DRG. According to these results the rTRPV1 and the rCGRP promoters appear to display selective activity for DRG while rASIC3 does not display such selectivity when expressed from the virus genome.

FIG. 14 shows that an amplicon vector expressing the reporter protein GFP can infect primary cultures of embryonic rat DRG neurons and adult rat DRG explants, and express the transgene GFP within these neurons.

FIG. 15 Intradetrusor inoculation of defective HSV-1 vectors reach dorsal root ganglia (DRG) and express transgenes in sensory neurons innervating the bladder.

Viral vector expressing IE4/5-GFP and HCMV-Luciferase (shown in FIG. 3B) is capable to penetrate and express both transgenic proteins in the bladder afferent neurons following their inoculation into the bladder wall of spinal cord-injured (SCI) rats. DRG neurons expressing both GFP and Luciferase (Luc) are shown in DRG ganglion L6, from which neurons that innervate the bladder extend. However, in the DRG ganglion T13, which does not innervate the bladder, the results are negative. One week post-infection, the animals were sacrificed and transgenic proteins were revealed by IHC using specific antibodies for GFP and Luciferase. These results indicate that following inoculation into the bladder wall, the vectors enter the afferent neurons innervating the bladder and are retrogradely transported through the axons to the cell bodies of the neurons to the L6 ganglia, which lie in the dorsal root ganglia (DRG), from where the viral genome express both transgenic proteins. Vectors are not able to reach or to express in neurons not innervating the bladder (T13).

Figure 16:
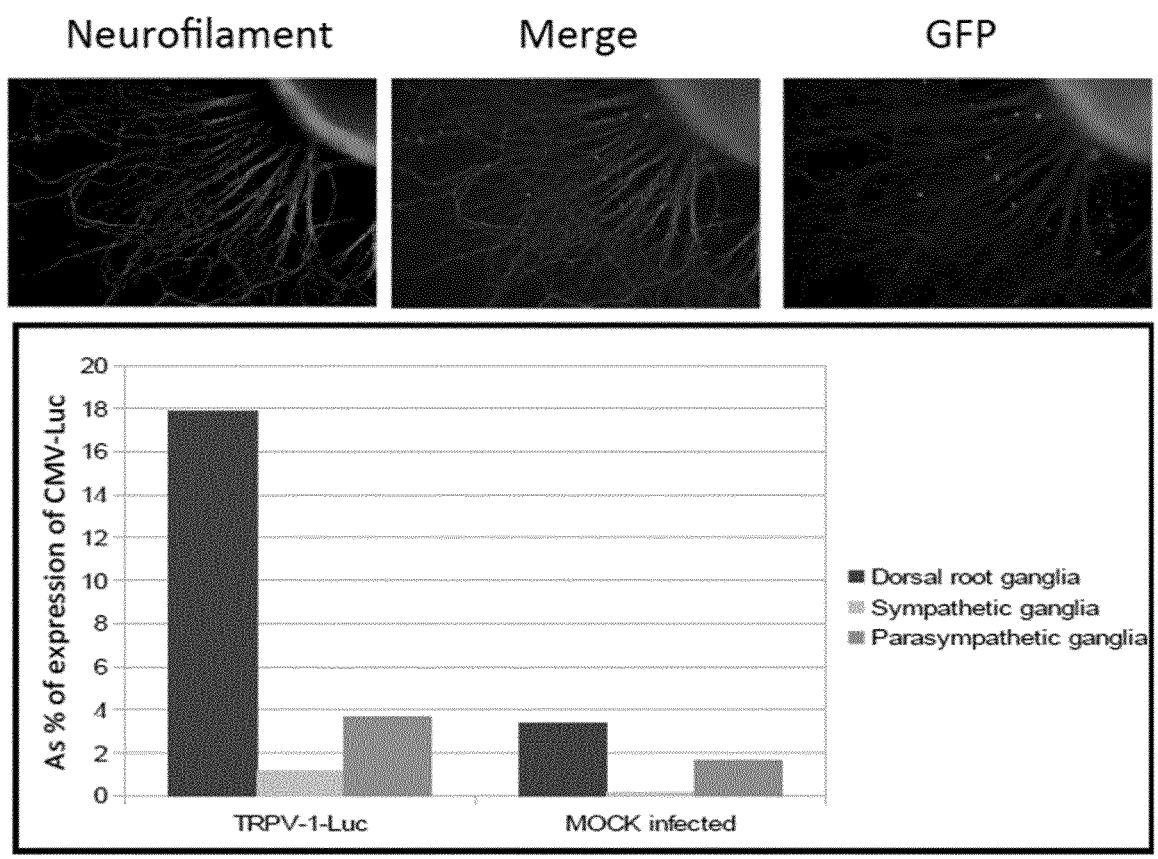

FIG. 16 shows the high cell selectivity of expression of the viral vector in the dorsal root ganglia (DRG) when Luciferase is driven by the DRG-selective TRPV1 promoter. Luciferase is significantly expressed only in the afferent neurons, and not in the autonomic neurons (sympathetic or parasympathetic). Results were normalized as percentage of luciferase expression relative to that from the vector expressing Luciferase under the control of the strong but not specific HCMV promoter (both vectors are shown in FIG. 3B).

EXAMPLES

Example 1

Construction of Defective Recombinant and Amplicon HSV-1 Vectors

Materials and Methods

Figure 1:
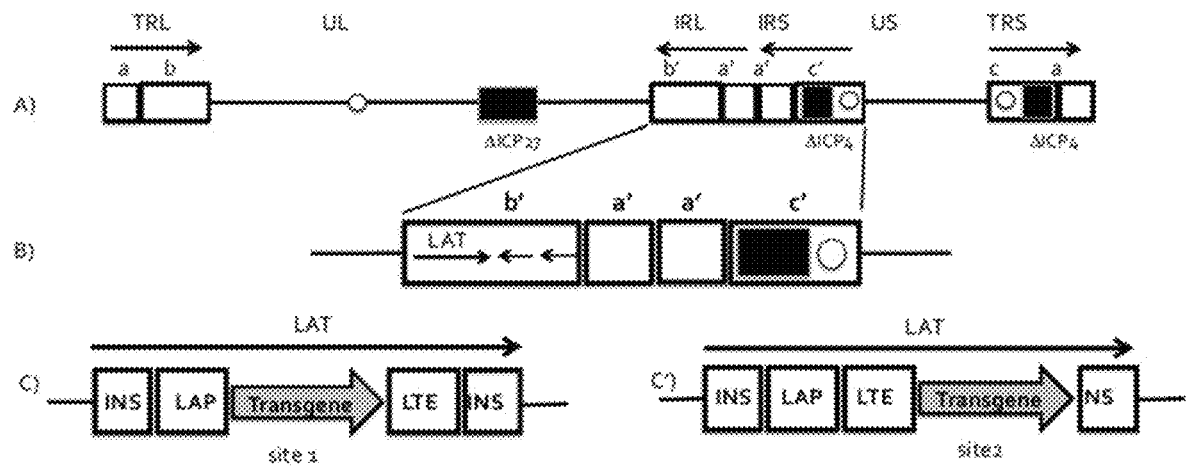
FIG. 1. Genome of recombinant defective HSV-1 vectors.
(A): The upper part of the figure describes the backbone of the HSV-1 genome used in this invention. The HSV-1 genome contains two unique regions, known as Unique Long (UL) and Unique Short (US), each bordered by repeated inverted sequences, known as Terminal Repeat L/Inverted Repeat L (TRL/IRL) and Inverted Repeat S/Terminal Repeat S (IRS/TRS). TRL/IRL are also denominated ab/b'a', whereas IRS/TRS are also denominated a'c'/ca. The genome therefore starts and ends by the direct repeat sequence 'a'. The black square in UL indicates that the gene coding for the essential ICP27 protein is deleted in the vector used in this invention. Similarly, the two black squares in the IRS/TRS repeats, indicate that the two genes coding for the essential ICP4 protein are also deleted. The white circle in UL, as well as the two white circles in the IRS and TRS regions, indicate the origins of DNA replication of HSV-1 (respectively OriL and two copies of OriS). Other genes, coding for non-essential proteins, such as UL41, UL55 and UL56, can be also deleted. In addition, both copies of the IE4/5 promoters localized in the IRS and TRS are modified in such a way (deletion of one TAATGARAT sequence) that these promoters express with early kinetics (instead of immediate-early kinetics as in the wild-type virus genome).
(B): The middle part of the figure shows a detail of the b'a'a'c' region of the virus genome, indicating in particular the localization of LAT locus in the IRL region, which contains the gene expressing the latency associated transcripts (LAT).
(C and C'): The bottom part of the figure shows the detailed structure of the 5' part of the LAT locus that carries the therapeutic DRG-specific transcription cassettes (indicated in the figure as the arrow labeled Transgene). This locus includes an upstream DNA insulator (INS) sequence, the Latency Associated Promoter (LAP), a region conferring Long-Term Expression (LTE) and a downstream DNA insulator (INS). The therapeutic DRG-specific transcription cassette is introduced either between the LAP and the LTE (site 1, in C) or between the LTE and the second DNA insulator (site 2 in C'). Other genes in the vicinity of LAT are also indicated in B (arrows). The different DRG-specific transcription cassettes that are introduced in the LAT region to generate the recombinant vectors are shown in FIG. 3. It should be stressed that the region b'a'a'c' is identical to the inverted caab region, which forms when the virus genome becomes circularized in the cell nucleus at the beginning of infection. This means that both copies of ICP4 are deleted and that the transgenic transcription cassette can be introduced in both copies of the LAT locus.

The invention provides set of defective recombinant HSV-1 vectors comprising complete deletions of ICP27 and ICP4 (both copies), and which carries, in addition, the therapeutic transcription cassettes embedded into the LAT locus, either between the LAP and LTE sequences (site 1) or between the LTE and INS sequences (site 2), as shown in FIG. 1 and FIG. 2, to provide long-term expression to said cassette. Some of the transcription cassettes used to generate these vectors are shown in FIG. 3.

Said transcription cassettes express the light chains (LC) of the Clostridium toxins TeNT (LC), BoNT-A (LC), BoNT B (LC), BoNT-C (LC), BoNT E (LC), BoNT-F (LC), or an antisense RNA (asRNA) directed to the SNARE proteins, VAMP2, SNAP25 and Syntaxin, or fusion SNARE/light-chain toxins, or the human GAD67 protein or a RIP protein such as Saporin S6, or the *E. coli* NTR nfnB, to inhibit/silence neurotransmission specifically in afferent neurons when, placed under the control of an afferent neuron-specific promoter.

To generate the vectors, we used a full-length HSV-1 genome of strain F cloned into a bacterial artificial chromosome (BAC) such as that described by Tanaka et al, 2003. Gene deletions and gene insertions were introduced by homologous recombination in bacteria and the vectors were then reconstituted by transfection of permissive cell lines as already described (Tanaka et al. 2003). The general structure of these vectors is illustrated in FIG. 1A.

Genome of HSV-1 Amplicon Vectors. FIG. 2.

The invention also provides a set of defective amplicon vectors, which express the same transgenic therapeutic transcriptions cassettes as the recombinant vectors, and listed in FIG. 7. Sequences conferring long-term expression (LTE and INS) surround the transcription cassettes (FIG. 2). FIG. 2 also shows that in addition to the therapeutic transcription cassettes, amplicon vectors carry a second transcription cassette, expressing a reporter protein (either GFP or the fusion protein GFP/renilla luciferase) driven in all cases by the HSV-1 IE4/5 promoter.

Amplicon vectors are produced using as helper the defective LaLdeltaJ virus and the complementing cell lines already described by Epstein and collaborators (Zaupa, Revol-Guyot and Epstein, 2003), which expresses the set of proteins required for amplification and packaging of the vector genome.

Transcription Cassettes Carried by Recombinant and Amplicon Vector Genomes. FIG. 7.

The recombinant and amplicon vectors described in this invention carry and express transgenic transcription cassettes embedded into HSV-1 sequences that confer long-term expression (LAP, LTE, INS), in both types of vectors, as shown in FIGS. 1 and 2. Some examples of the transcription cassettes used in this invention are listed in FIG. 7.

Example 2

HSV-1 Amplicon Vectors

The invention also provides a set of defective amplicon vectors, some of these vectors express either reporter proteins (luciferase) or the light chains (LC) of the Clostridium toxins (TeNT (LC), BoNT-A (LC), BoNT B (LC), BoNT-C (LC), BoNT E (LC), BoNT-F (LC)), or an antisense RNA (asRNA) directed to the SNARE proteins, VAMP2, SNAP25 and Syntaxin, or chimeric SNARE/light-chain toxins, or the human GAD67 protein or a RIP protein such as Saporin S6 or a nitroreductase (NTR) protein such as nfnB. The promoters (prom) that drive the expression of these transgenes are either non-specific promoters (HCMV, EF1A), or afferent neuron-specific of promoters (TRPV1, TRPM8, ASIC3, GCRP, ADV1). Additional sequences conferring long-term expression (LTE and DNA insulator sequences) are added to some of these promoters (FIG. 3A). The promoter that governs the expression of the reporter GFP, or the GFP-rLuc fusion protein, present in amplicon vectors, is the viral immediate-early promoter known as HSV-1 IE4/5 promoter. The general structure of some of the amplicon vectors used herein is shown in FIG. 3B.

Example 3

Expression of BoNT-A, BoNT-C and TeNT. FIG. 4

The expression of BoNT-A (LC), BoNT-C (LC) and TeNT (LC) is performed in Gli36 (a cell line derived from a human glioblastoma) and BHK21 (hamster fibroblast cells) cell lines. Gli36 and BHK21 cells are infected with the amplicon vectors expressing HCMV-Luc, HCMV-BoNT-A (LC), HCMV-BoNT-C (LC), or HCMV-TeNT (LC). The cells were then fixed and the expression of the toxin was demonstrated by Western blot using anti-TeNT antibodies to reveal TeNT (LC) and anti-HIS antibodies to reveal BoNT-A (LC) and BoNT-C (LC). Indeed, there is no efficient anti-BoNT antibodies available, therefore BoNT-A (LC) and BoNT-C (LC) are expressed as a fusion protein with a C-terminal HIS-tag. FIG. 4 shows that the viral vector carrying the genes coding for HCMV-BoNT-A (LC), HCMV-BoNT-C (LC), and HCMV-TeNT (LC) express respectively BoNT-A (LC), BoNT-C (LC) and TeNT (LC) in both Gli36 and BHK21 cells.

Example 4

In Vitro Proteolytic Activity of the Recombinant Toxin TeNT. FIG. 5

Proteolytic activity of the toxin TeNT (LC) with respect to VAMP2 was evaluated by Westerns blots using anti-VAMP2 antibody. The toxin TeNT (LC) was expressed in Gli36 cells after infection with the viral expression vector expressing HCMV-TeNT (LC). The infection was terminated 2 days later and protein extracts were prepared. These extracts were incubated in a suitable buffer (containing 50 mM Hepes, 400 mM NaCl, 5 mM dithiothreitol and 2 μM ZnSO4) containing the target protein of TeNT, i.e VAMP2. Westerns blots (FIG. 5) were performed using 2.5, 5, and 10 μL of cell extracts. Untreated sample, a sample from cells infected with a vector expressing no transgene (pA-1), and a sample from cells infected with a vector expressing HCMV-Luc (10 μL) were used as a negative control. Varying amounts of recombinant TeNT (recTeNT) were used as a positive control. Results show that the quantity of VAMP2 decreases when the protein extract expressing TeNT (LC) is increased, which demonstrate that the toxin present in the protein extract exhibits a proteolytic activity toward VAMP2.

Example 5

Figure 6B:
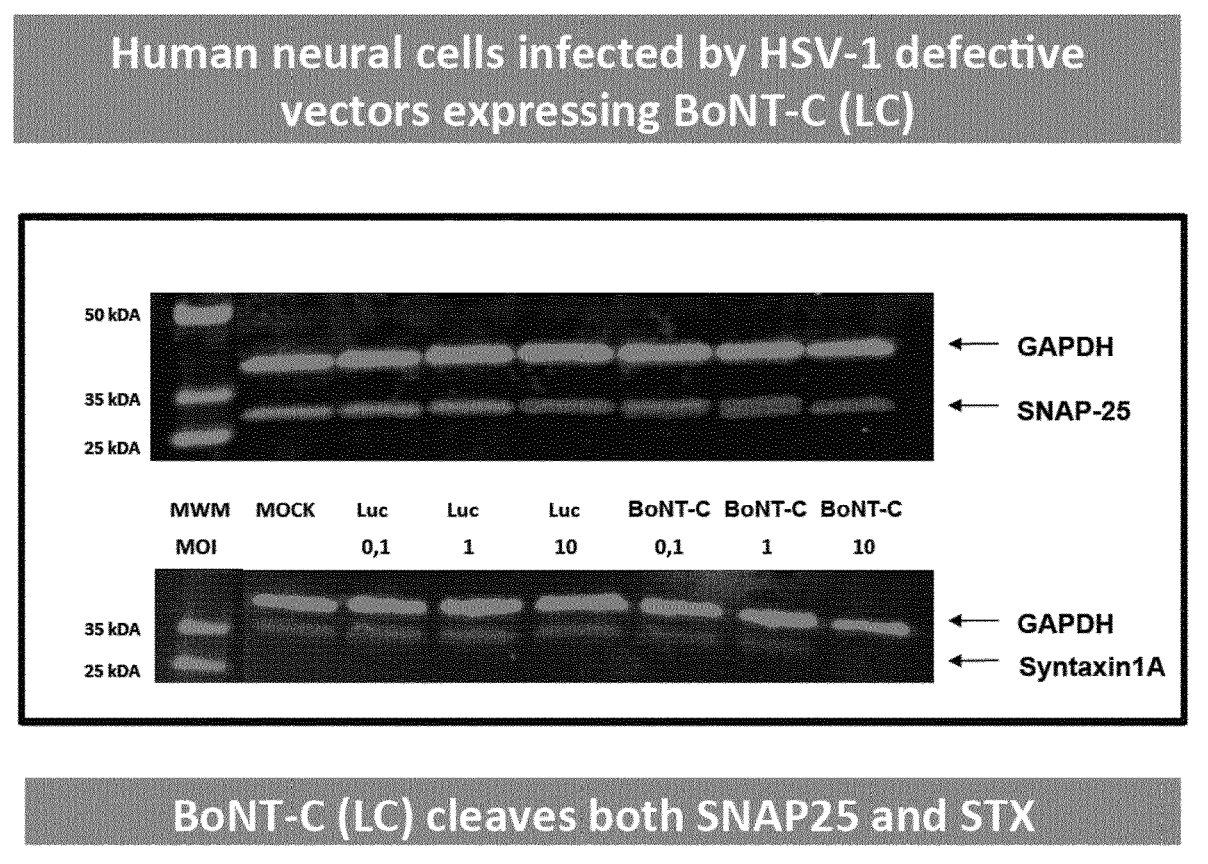

In Cellulo Proteolytic Activity of the Recombinant Toxins BoNT-A (LC) and BoNT-C (LC). FIG. 6

The SH-S5Y5 human neuroblastoma cell line was used for their property to spontaneously express SNARE proteins, in order to follow in cellulo SNAP25 and Syntaxin 1a (STX) cleavage following infection by amplicon vectors expressing BoNT-A (LC) or BoNT-C (LC). SNAP25 and STX levels were detected by Western blot assay using anti-SNAP25 or anti-STX antibodies respectively. As negative controls, cells were not infected (Mock) or were infected with the vector expressing HCMV-Luc. Results (FIGS. 6a and 6b) show that at 48 hours post-infection (hpi) of SH-S5Y5 cells with vectors expressing the light chains of BoNT-A or BoNT-C, there is respectively cleavage and significant decrease of in cellulo SNAP25 (FIG. 6a) or SNAP25 and STX (FIG. 6b) protein levels relative to cells infected with the control vector expressing Luciferase.

Example 6

FIG. 8

BoNT-A Expressed From Amplicon Vectors Cleaves the SNARE Protein SNAP25 in SH-SYS5 Cells This experiment was designed to assess whether vectors expressing the light chain of BoNT-A do express this protein, and to study whether this toxin has the same biological activity that the complete neurotoxin (light chain+heavy chain), i.e., the ability to cleave its target SNARE protein (SNAP25). As shown in FIG. 8, cells infected at increasing multiplicities with amplicon expressing A2-CMV-BoNT-A do express increasing amounts of the toxin. Moreover, when cells are infected at high MOI virtually all SNAP25 is cleaved, clearly demonstrating the functional activity of the light chain of BoNT-A.

Example 7

FIG. 9

Light Chains of Botulin Neurotoxins Cleave SNARE Proteins in Infected Neurons.

This experiment was designed to confirm that all BoNT light chains synthesized in vector-infected neurons are able to cleave their natural SNARE target protein in sensory neurons. To this end, primary cultures of rat embryonic DRG neurons were infected at an MOI of 10 with amplicon vectors expressing A2-CMV-BoNT-A, -B, -C, -D, -E and -F, or A2-CMV-Luc as negative control. Infections were stopped the following day and cell extracts were analyzed by Western blots. As shown in FIG. 9, each of the botulinum neurotoxin expressed by the vectors cleaved its natural target SNARE protein. Thus, BoNT-A and -E cleaved SNAP25, BoNT-B, -D and -F cleaved VAMP2, while BoNT-C cleaved both SNAP25 and Syntaxine. This clearly demonstrates that the light chains of all neurotoxins display the same biological activity as the complete neurotoxins (light chain+heavy chain).

Example 8

FIG. 10

Light Chains of Botulin Toxins Inhibit Release of Neuropeptides in Sensory Neurons.

This experiment was designed to assess whether the light chains of botulinum neurotoxins induced inhibition of release of neurotransmitters and to evaluate their comparative efficacy in this respect. Primary cultures of rat embryonic DRG neurons were infected at increasing MOI with the vectors as described in FIG. 10. The following day, infected neurons were treated with KCl to stimulated release of neuropeptide CGRP and the extracellular concentrations of CGRP were evaluated by ELISA. As shown in FIG. 10, all neurotoxins induced inhibition of release of CGRP. Moreover, FIG. 6 shows that BoNT-F was the most effective in this respect, followed by BoNT-A and -C.

Example 9

FIG. 11

GAD67 Expressed From Amplicon Vectors Induces Synthesis and Extracellular Release of GABA.

The goal of this experiment is to assess whether vectors expressing GAD67 induce synthesis and release of the inhibitory neutransmitter GABA. To this end, glioblastoma cells (Gli36) were infected at increasing MOI with amplicon vectors as described in FIG. 11 and the following day infected cell extracts were analyzed by Western blots, using antibodies specific for GAD67 and GAPDH. FIG. 11 shows that expression of GAD67 increases with the MOI, demonstrating that vector A2-CMV-GAD67 does express this protein. In addition, primary cultures of rat embryonic DRG neurons were infected at different MOIs with the same vectors. The following day infections were stopped and both, intracellular and extracellular, concentrations of GABA were evaluated using Resazurine assay (as indicated in the legend to FIG. 11). The upper panel of this figure shows that the amount of intracellular GABA increases with the MOI, while the lower panel shows the increase of extracellular GABA, clearly demonstrating that expression of GAD67 from the A2-CMV-GAD67 vector increases synthesis of intracellular GABA and its release to the extracellular medium.

Example 10

FIG. 12

Nitroreductase (NTR) Activates the Nitro Compound 7'Nitrocoumarin and Induces Cell Death in the Presence of Mitronidazole (MTZ).

This experiment was designed to assess whether nitroreductase expressed from amplicon vectors induced cell death in the presence, but not in the absence of metronidazole. There are no available antibodies specific for nitroreductase (NTR). Therefore, to assess that this protein is expressed in A2-CMV-NTR infected cells, we used a functional in vitro test based on the evaluation of reduction of 7'nitrocoumarin (Muller et al., 2015). FIG. 12 shows that amplicon vectors expressing A2-CMV-NTR do activates the nitro compound. Furthermore, FIG. 12 shows that expression of NTR induced significant cell death in the presence of metronidazole (MTZ). This is explained by the fact that NTR can activate MTZ thus transforming this molecule into a cytotoxic drug.

Example 11

FIG. 13

Analysis of the Selectivity of Expression of DRG-Selective Promoter Candidates in Autonomic and Sensory Ganglia From Adult Rats.

Figure 13:
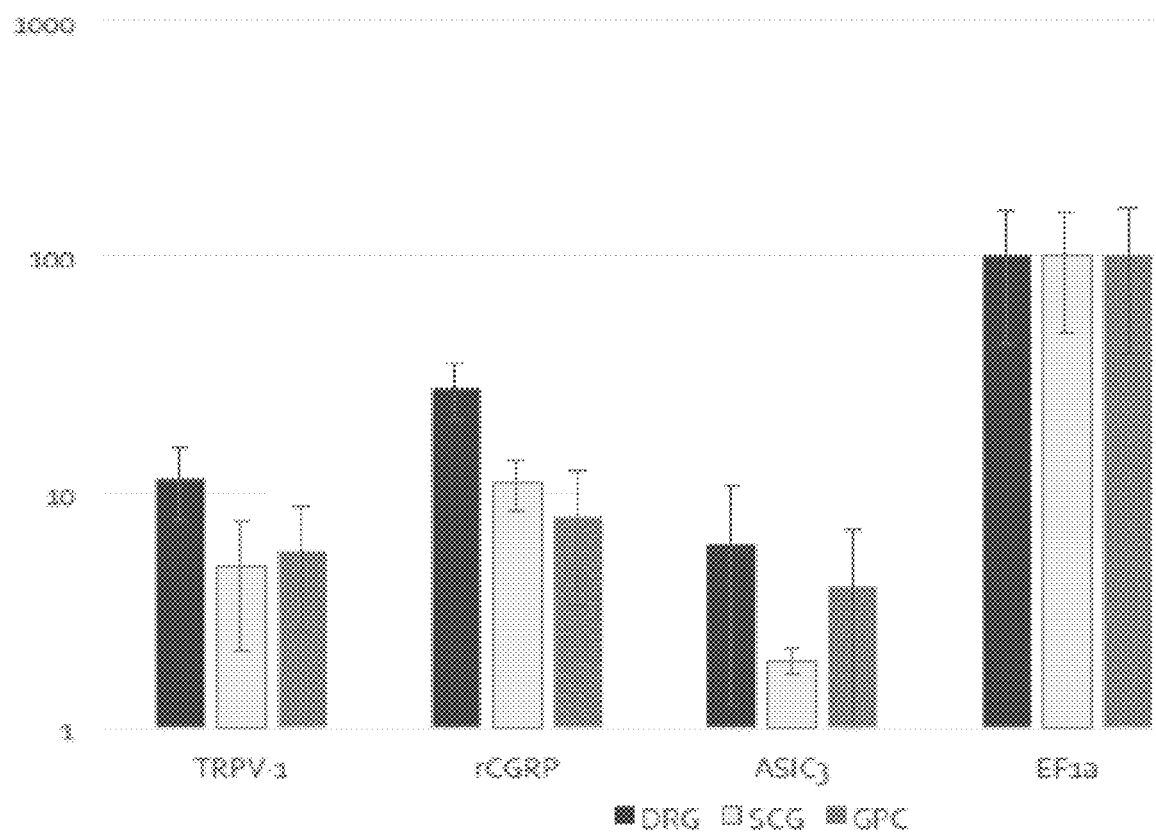

This test was designed to investigate whether afferent neuron-specific promoter candidates, which normally are active only or mainly in afferent neurons, preserve their afferent neurons-specific activity also when they are expressed from the non-replicative HSV-1 vector genome. Rat adult afferent ganglia (DRG), autonomic sympathetic ganglia (SCG), and autonomic parasympathetic ganglia (GPC) were explanted and kept as organotypic cultures. After 3 days, a time required for neurite outgrowth, the ganglia were individually infected with $3\times10^6$ vector particles as described in the legend to FIG. 13. These vectors express firefly luciferase (fLuc) driven by the following promoters: rat TRPV1 (rTRPV1), rat CGRP (rCGRP), rat ASIC3 (rASIC3), all of which are considered as afferent-neuron specific promoters, and EF1a, a non-selective promoter serving as general control. In addition to fLuc, these vectors also express renilla luciferase (rLuc) driven by a viral promoter (HSV-1 IE4/5). The following day infections were stopped and cells extracts were prepared for luciferase tests. Results are expressed as the ratio of fLuc/rLuc and as percentage of luciferase activity driven by EF1a. FIG. 13 shows that rTRPV1 and rCGRP express firefly luciferase activity preferentially in DRG and can thus be considered as DRG-specific even when they express from the vector genome. In contrast, rASIC3 does not display such preferential expression in the DRG demonstrating that this promoter does not preserve its selectivity when expressed from the vector genome. Therefore, this example shows that some DRG-specific promoter candidates, such as the rTRPV1 and rCGRP promoters, do preserve their selectivity for DRG while other promoter candidates, such as rASIC3, although considered a DRG-specific promoter when it expresses from the cellular chromosomes, does not preserve this specificity when expressed from the vector genome. Therefore, the behavior of any particular DRG-specific promoter candidate cannot be predicted and should be experimentally assessed.

Example 12

Infection and Expression of the Recombinant Protein in Cell Cultures

Primary rat neuronal cultures from embryonic DRG and organotypic cultures of adult rat DRG explants were infected with and amplicon vector expressing GFP driven by the HSV-1 immediate early IE4/5 promoter. Results show that the viral expression vector infected and expressed the transgene (GFP) both in primary rat sensory neuronal cultures and in adult rat ganglion (DRG) explants (FIG. 14).

Example 13

In Vivo Expression of Recombinant Proteins in Neurons

Figure 15:
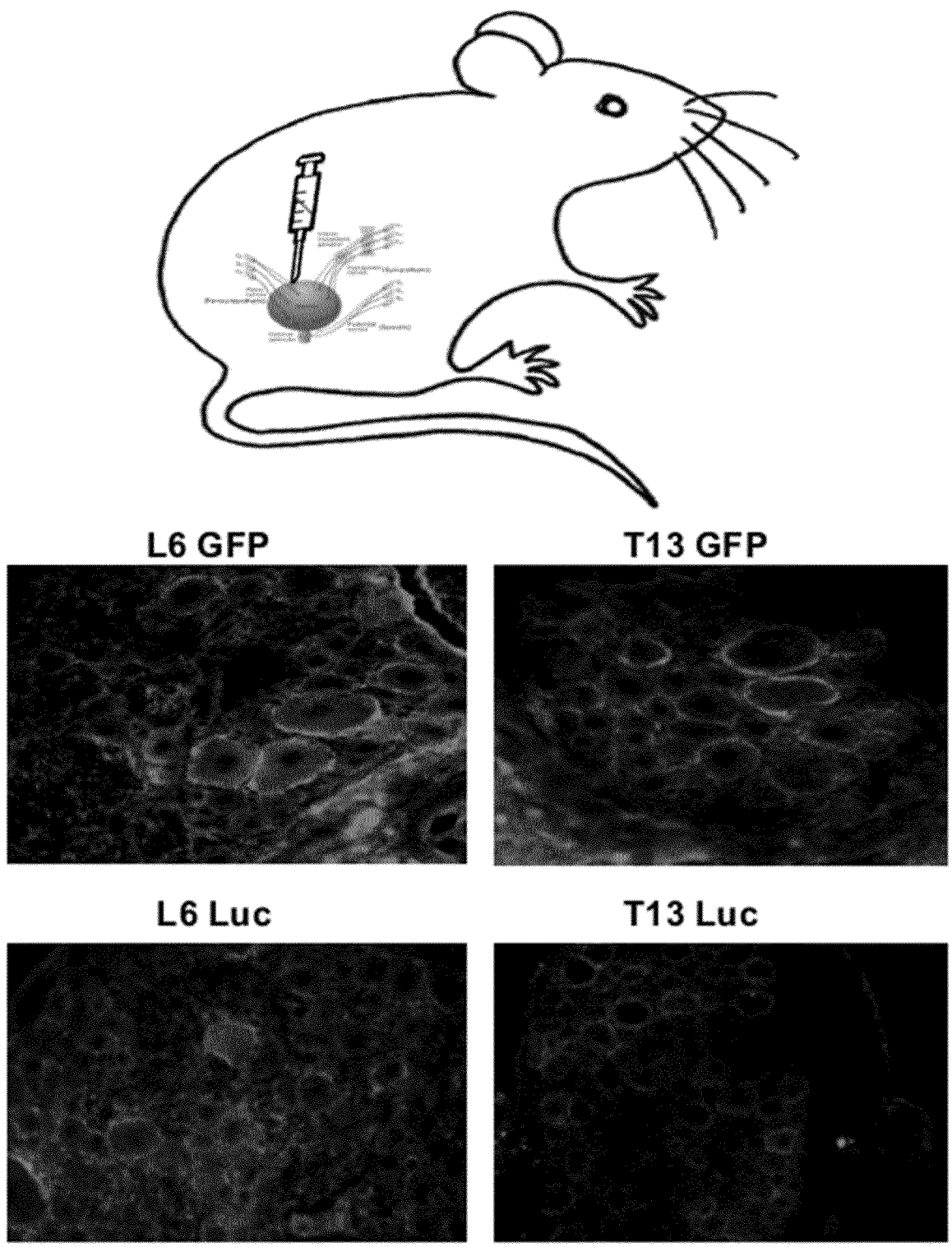

Spinal cord injured (SCI) rats were infected by the amplicon vector HCMV-Luc, which simultaneously expresses GFP and Luc reporter proteins. One week post-infection, the animals were sacrificed and transgenic proteins expressions were revealed by IHC. As indicated by the IHC, when inoculated into the bladder the amplicon vector is entering the afferent neurons innervating the bladder, and is then retrogradely transported through the axons to the cell bodies of the neurons, which lie in the dorsal ganglia (DRG), and where the viral genome express both transgenic protein. Results indicate that amplicon vectors HCMV-Luc are thus capable to penetrate and specifically express transgenic proteins into the bladder afferent neurons following their inoculation into the bladder wall (FIG. 15). Moreover, neurons expressing GFP and Luc are observed only in the ganglion from which neurons that innervate the bladder extend (the L6 ganglion). In contrast, in the ganglion T13, which does not innervate the bladder, no transgene expression could be observed (data not show).

Example 14

Cell Specificity Expression of the Viral Expression Vector

The amplicon vectors TRPV1-Luc, expressing luciferase under control of the promoter TRPV1 (promoter active selectively in afferent neurons) and HCMV-Luc, expressing luciferase under the control of the non-selective HCMV promoter, were used to infect sensory or autonomic ganglia (both sympathetic and parasympathetic ganglia). Results show that expression of the luciferase under TRPV1 promoter is specifically expressed in the afferent neurons of the sensory ganglia (Dorsal Root Ganglia, DRG), and not in the autonomic neurons (sympathetic or parasympathetic) (FIG. 16). Results are expressed as percentage of expression driven by the non-selective HCMV promoter, which is equally high in all types of ganglia.

BIBLIOGRAPHIC REFERENCES

Amelio A L, McAnany P K and Bloom D C. A chromatin insulator-like element in the herpes simplex virus type 1 latency-associated transcription region binds CCCTC-binding factor and displays enhancer-blocking and silencing activities. Journal of Virology 80: 2358-2368 (2006).

Berthommé H, Lokensgard J, Yang L, Margolis T, and Feldman L T. Evidence for bidirectional element located downstream from the herpes virus simplex type 1 latency-associated promoter that increases its activity during latency Journal of Virology 74:3613-3622 (2000).

Berthommé H, Thomas J, Texier P, Epstein A and Feldman L T. Enhancer and long-term expression functions of herpes simplex virus type 1 latency-associated promoter are both located in the same region. Journal of Virology 75: 4386-4393 (2001).

Brindley G S, Polkey C E, Rushton D N, and Cardozo L. Sacral anterior root stimulators for bladder control in paraplegia: the first 50 cases. J Neurol Neurosurg Psychiatry 49: 1104-1114 (1986).

De Groat W C. Spinal cord projections and neuropeptides in visceral afferent neurons. Prog Brain Res 67:165-187 (1986).

De Groat W C and Yoshimura N. Mechanisms underlying the recovery of lower urinary tract function following spinal cord injury. Prog Brain Res 152: 59-84 (2006).

Epstein A L. HSV-1-derived amplicon vectors: recent technological improvements and remaining difficulties—A review. Mem Inst Oswaldo Cruz 104: 339-410 (2009).

Fowler C J, Griffiths D and de Groat W C. The neural control of micturition. Nat Rev Neurosci 9: 453-466 (2008).

Furuta Y, Takasu T, Fukuda S, Inuyama Y, Sato K C, Nagashima K. Latent herpes simplex virus type 1 in human vestibular ganglia. Acta Otolaryngol Suppl. 1993; 503:85-9.

Habermann E, and Dreyer F. Clostridial neurotoxins: handling and action at the cellular and molecular level. Curr. Top. Microbiol. Immunol. 129: 93-179 (1986).

Lokensgard J R, Berthommé H and Feldman L T. The latency-associated promoter of herpes simplex virus type 1 requires a region downstream of the transcription start site for long-term expression during latency. Journal of Virology 71: 6714-6719 (1997).

Marconi P, Manservigi R and Epstein A L. HSV-1-derived helper-independent defective vectors, replicating vectors and amplicon vectors, for the treatment of brain diseases. Current opinion in drug discovery and development 13: 169-183 (2010).

McCart J A 1, Wang Z H, Xu H, Hu Y, Park B, Alexander H R, Bartlett D L. Development of a melanoma-specific adenovirus. Mol Ther. 2002 October; 6(4):471-80.

Morrison J F, Birder L, Craggs M, de Groat W C, Downie J W, Drake M, Fowler C J, Thor K B. Neural control. In: Abrams P, Cardozo L, Khoury S, Wein A, editors. Incontinence. Plymouth: Health, 363-422 (2005).

Perng G, Ghiasi H, Slavina S M, Nesburn A B, and Wechsler S. The spontaneous reactivation function of the herpes simplex virus type 1 LAT gene resides completely within the first 1.5 kilobases of the 8.3-kilobase primary transcript. Journal of Virology 70: 976-984 (1996).

Ren J, Chew D J, Biers S, Thiruchelvam N. Electrical nerve stimulation to promote micturition in spinal cord injury patients: A review of current attempts. Neurourol Urodyn. doi: 10.1002/nau.22730. [Epub ahead of print] (2105).

Sugiyama H. *Clostridium botulinum* neurotoxin. Microbiol. Rev. 44, pp. 419-448 (1980).

Tanaka M, Kagawa H, Yamanashi Y, Sata T, and Kawaguchi Y. Construction of an excisable bacterial artificial chromosome containing a full-length infectious clone of herpes simplex virus type 1: viruses reconstituted from the clone exhibit wild-type properties in vitro and in vivo. Journal of Virology 77: 1382-1391 (2003).

Warren K G, Brown S M, Wroblewska Z, Gilden D, Koprowski H, Subak-Sharpe J. Isolation of latent herpes simplex virus from the superior cervical and vagus ganglions of human beings. N Engl J Med. 1978 May 11; 298 (19):1068-9.

Zaupa C, Revol-Guyot V and Epstein A L. Improved packaging system for generation of high-level noncytotoxic HSV-1 amplicon vectors using Cre-loxP site-specific recombination to delete the packaging signals of defective helper genomes. Human Gene Therapy 14: 1049-1063 (2003).

The invention claimed is:

1. A herpes simplex virus (HSV) viral expression vector comprising at least:
    a) one promoter active selectively in afferent neurons of the bladder, wherein the promoter is a promoter of Calcitonin Gene Related Peptide (CGRP),
    b) at least one transcription cassette comprising a nucleotide sequence operably linked to said promoter, wherein said nucleotide sequence codes for a fusion protein comprising a modified bacterial neurotoxin and a signal peptide domain, wherein the fusion protein is chosen from the group consisting of SEQ ID NO: 28, SEQ ID NO: 30, and SEQ ID NO: 32, wherein said nucleotide sequence inhibits the transduction of the neurotransmitter signal in a postsynaptic cell when transcribed, and
    c) a long-term expression (LTE) sequence and a DNA insulator from the HSV-1 genome, wherein said transcription cassette is placed between the LTE sequence and the DNA insulator.

2. The viral expression vector according to claim 1, wherein said nucleotide sequence inhibits neurotransmission or synaptic transmission of afferent neurons when transcribed by disrupting at least the soluble N-ethylmaleimide-sensitive factor attachment protein receptor (SNARE) complex.

3. The viral expression vector according to claim 1, wherein said viral expression vector codes for a fusion protein comprising a modified bacterial neurotoxin and a signal peptide domain, wherein the fusion protein is chosen from the group consisting of SEQ ID NO: 30 and SEQ ID NO: 32.

4. A pharmaceutical composition comprising at least one viral expression vector according to claim 1.

5. A Kit comprising at least one viral expression vector according to claim 1, and an electrical stimulation system comprising electrodes to be implanted on the sacral anterior roots, to apply intermittent stimulation pulse trains in order to achieve a sustained detrusor muscle contraction with intervals of urethral sphincter relaxation allowing urine to flow.

6. The viral expression vector according to claim 1, wherein said promoter is a promoter of CGRP of SEQ ID NO: 3 or SEQ ID NO: 4.

7. The viral expression vector according to claim 1, wherein said HSV vector is a HSV-1 vector.

8. A method for the treatment of neurogenic detrusor overactivity comprising administering the pharmaceutical composition of claim 4 to a patient in need thereof.

9. The viral expression vector according to claim 1, wherein the HSV vector is a defective viral vector derived from HSV.

* * * * *